United States Patent [19]

Nakajima et al.

[11] Patent Number: 5,741,814
[45] Date of Patent: *Apr. 21, 1998

[54] CYCLOOCTADIENE DERIVATIVES

[75] Inventors: Yasuyuki Nakajima; Hisayuki Watanabe; Michiaki Adachi, all of Funabashi; Michito Tagawa, Minamisaitama-gun; Mitsugu Futagawa, Minamisaitama-gun; Takashi Furusato, Minamisaitama-gun; Hiroshi Ohya, Minamisaitama-gun; Masanori Nishioka, Minamisaitama-gun, all of Japan

[73] Assignee: Nissan Chemical Industries, Ltd., Tokyo, Japan

[ * ] Notice: The term of this patent shall not extend beyond the expiration date of Pat. No. 5,346,919.

[21] Appl. No.: 682,782

[22] PCT Filed: Feb. 1, 1995

[86] PCT No.: PCT/JP95/00128

§ 371 Date: Sep. 3, 1996

§ 102(e) Date: Sep. 3, 1996

[87] PCT Pub. No.: WO95/21149

PCT Pub. Date: Aug. 10, 1995

[30] Foreign Application Priority Data

Feb. 1, 1994 [JP] Japan .................. 6-010440

[51] Int. Cl.$^6$ .................. A61K 31/34; C07D 307/93
[52] U.S. Cl. .................. 514/468; 514/411; 514/529; 514/574; 548/429; 549/239; 549/268; 549/299; 549/354; 560/106; 560/127; 562/509; 564/153; 568/326; 568/633
[58] Field of Search .................. 549/239, 268, 549/299, 354; 568/633, 326; 548/429; 560/106, 127; 562/509; 564/153; 514/411, 468, 529, 574

[56] References Cited

U.S. PATENT DOCUMENTS 5,346,919  9/1994  Watanabe et al. .................. 514/468
5,460,814  10/1995  Watanabe et al. .................. 424/122

*Primary Examiner*—Bernard Dentz
*Attorney, Agent, or Firm*—Oliff & Berridge, PLC

[57] ABSTRACT

Cyclooctadiene derivative of the following formula (1):

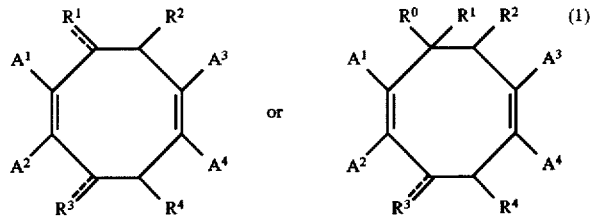

wherein
$A^1$, $A^2$, $A^3$ and $A^4$ each independently represent $COOR^5$ (where $R^5$ represents a hydrogen atom, a $C_1$–$C_{10}$ alkyl group, a phenyl group, a $C_7$–$C_{12}$ aralkyl group or $CONR^6R^7$ (where $R^6$ and $R^7$ each independently represent a hydrogen atom, a $C_1$–$C_{10}$ alkyl group or a phenyl group), or $A^1$ and $A^2$, and/or $A^3$ and $A^4$ may be combined together to represent group(s) of:

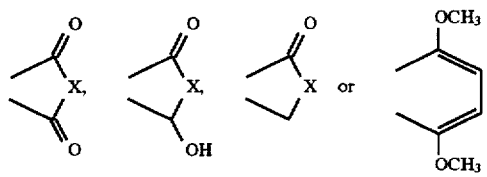

in which
X represents an oxygen atom or $NR^8$ {where $R^8$ represents a hydrogen atom, a $C_1$–$C_{10}$ alkyl group or a phenyl group),
$R^0$, $R^1$, $R^2$, $R^3$ and $R^4$ each independently represent a hydrogen atom, a halogen atom, a hydroxyl group and an $C_1$–$C_{10}$ alkyl group,
the symbol ——— represents a single or double bond, and when it is a double bond, then $R^1$ and $R^3$ each independently may represent an oxygen atom;
provided that the case where all of $R^0$, $R^1$, $R^2$, $R^3$ and $R^4$ represent hydrogen atoms at the same time is excluded, and agrohorticultural fungicides, antimold agents and antithrombocytic agents containing said derivatives.

The compounds have superior fungicidal activity, antimold activity and activity for preventing platelet aggregation, and are useful as an agrohorticultural fungicide, an antimold agent and an antithrombocytic agent.

11 Claims, No Drawings

CYCLOOCTADIENE DERIVATIVES

This application is a 371 of PCT/JP95/00128 filed Feb. 1, 1995.

1. Technical Field

The present invention relates to a novel cyclooctadiene derivative, and to an agrohorticultural (agricultural and horticultural) fungicide, an antimold and an antithrombocytic agent each containing the derivative as the active ingredient.

2. Background Art

Some cyclooctadiene derivatives have been reported in Journal of Polymer Science: Polymer Chemistry Edition, Vol. 13, p. 171 (1975), and Journal of Organic Chemistry, Vol. 42, p. 2601 (1977). However, these are used in the field of electronic materials and as organic synthetic compounds. Nothing is referred to therein about their physiological activities such as fungicidal activity, antimold activity and antithrombocytic activity.

Various antimolds and fungicides have heretofore been developed but are problematic in that their effects are unsatisfactory and that some fungi which are resistant to them have appeared. Therefore, novel antimolds and fungicides are desired.

In addition, since many of the fungicides that have heretofore been developed are artificially-synthesized compounds, their use has become considered problematic in these days in that they have been found to have some negative influences on the environment. For these reasons, an increasing interest is being taken in compounds to be derived from natural substances, which will have few influences on the environment, and the development of fungicides comprising such compounds is therefore desired.

On the other hand, the development of novel antithrombotic agents is also desired for the reasons mentioned below.

It has been clarified that thrombocytoagglutination is one important factor in thrombogenesis in relation to its pathomorphism. Thrombogenesis is known to cause various thrombotic disorders, of which some typical ones include, for example, cerebral thrombosis, pulmonary thrombosis, myocardial infarction, stenocardia and peripheroarterial obstruction. It is desired to develop medicines efficacious against such disorders. As medicines for preventing and curing such thrombotic disorders, antithrombotic agents having an anti-thrombocytoagglutinative activity are specifically noted. The effect of aspirin has heretofore been widely studied, and recently, ticlopidine and cilostazol have been put into clinical demonstrations. At present, however, it is still desired to obtain more efficacious medicines.

Apart from the above-mentioned thrombotic disorders, some other disorders are said to have relation to thrombocytes. Such disorders include, for example, nephritis and metastasis of cancer cells. Recently, a wide variety of studies are being made on the effects of various antithrombotic agents having the ability to retard the functions of thrombocytes, essentially for preventing and curing these disorders (see Journal of Royal College of Physicians, Vol. 7, No. 1, pp. 5–18, 1972; Nippon Rinsyo, Vol. 4, No. 6, pp. 130–136, 1988; Anticancer Research, Vol. 6, pp. 543–548, 1986).

DISCLOSURE OF THE INVENTION

Given the situation, the present inventors have variously studied in order to develop excellent compounds and, as a result, have found that cyclooctadiene derivatives to be obtained through various chemical modifications of Compound A that is produced by microorganisms belonging to the genus Zopfiella and also their analogs as obtained through chemical synthesis have excellent fungicidal activity and antimold activity. On the basis of these findings, the inventors have completed the present invention.

The present inventors also have found that the compounds of the present invention additionally have antithrombocytic activity.

Specifically, the present invention relates to a cyclooctadiene derivative of the following formula (1) and also to an agrohorticultural fungicide, an antimold and an antithrombocytic agent each comprising the derivative as the active ingredient.

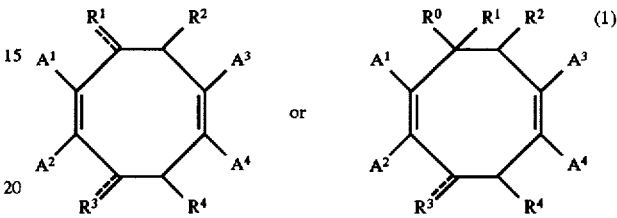

wherein
$A^1$, $A^2$, $A^3$ and $A^4$ each independently represent $COOR^5$ (where $R^5$ represents a hydrogen atom, a $C_1$–$C_{10}$ alkyl group, a $C_2$–$C_{10}$ alkenyl group, a $C_2$–$C_{10}$ alkynyl group, a phenyl group (the phenyl group may be optionally substituted by a halogen atom, a $C_1$–$C_6$ alkyl group, a $C_1$–$C_6$ haloalkyl group, a $C_1$–$C_6$ alkoxy group, a cyano group and/or a nitro group), or a $C_7$–$C_{12}$ aralkyl group (the aralkyl group may be optionally substituted by a halogen atom, a $C_1$–$C_6$ alkyl group, a $C_1$–$C_6$ haloalkyl group, a $C_1$–$C_6$ alkoxy group, a cyano group and/or a nitro group)), or $CONR^6R^7$ (where $R^6$ and $R^7$ each independently represent a hydrogen atom, a $C_1$–$C_{10}$ alkyl group or a phenyl group (the phenyl group may be optionally substituted by a halogen atom, a $C_1$–$C_6$ alkyl group, a $C_1$–$C_6$ haloalkyl group, a $C_1$–$C_6$ alkoxy group, a cyano group and/or a nitro group)), or $A^1$ and $A^2$, and/or $A^3$ and $A^4$ may be combined together to represent group(s) of:

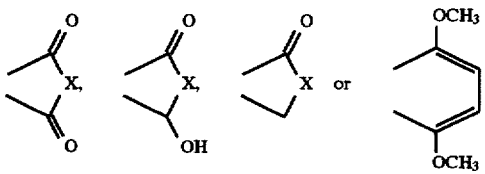

in which
X represents an oxygen atom or $NR^8$ {where $R^8$ represents a hydrogen atom, a $C_1$–$C_{10}$ alkyl group, a phenyl group (the phenyl group may be optionally substituted by a halogen atom, a $C_1$–$C_6$ alkyl group, a $C_1$–$C_6$ haloalkyl group, a $C_1$–$C_6$ alkoxy group, a cyano group and/or a nitro group), or a $C_7$–$C_{12}$ aralkyl group (the aralkyl group may be optionally substituted by a halogen atom, a $C_1$–$C_6$ alkyl group, a $C_1$–$C_6$ haloalkyl group, a $C_1$–$C_6$ alkoxy group, a cyano group and/or a nitro group)};

$R^0$, $R^1$, $R^2$, $R^3$ and $R^4$ each independently represent a hydrogen atom, a halogen atom, a hydroxyl group, an optionally-substituted $C_1$–$C_{10}$ alkyl group, an optionally-substituted $C_2$–$C_{10}$ alkenyl group, or an optionally-substituted $C_2$–$C_{10}$ alkynyl group;
the substituent for the optionally-substituted groups can be any one or more selected from the group consisting of a halogen atom, a $C_1$–$C_6$ alkyl group, a $C_2$–$C_6$ alkenyl group, a $C_2$–$C_6$ alkynyl group, a $C_1$–$C_6$ haloalkyl group, $OR^9$ {where $R^9$ represents a hydrogen atom, a $C_1$–$C_6$ alkyl group, a $C_2$–$C_6$ alkenyl group, a $C_2$–$C_6$ alkynyl group, a $C_1$–$C_6$ haloalkyl group, a silyl group, a $C_1$–$C_4$ alkylsulfonyl group, a $C_7$–$C_{12}$ aralkyl group (the aralkyl group may be optionally substituted by a halogen atom, a $C_1$–$C_6$ alkyl group, a $C_1$–$C_6$ haloalkyl group, a $C_1$–$C_6$ alkoxy group, a cyano group and/or a nitro group), a phosphoryl group, a $C_2$–$C_{10}$ alkoxyalkyl group, or $COR^{14}$ where $R^{14}$ represents a $C_1$–$C_6$ alkyl group, a phenyl group (the phenyl group may be optionally substituted by a halogen atom, a $C_1$–$C_6$ alkyl group, a $C_1$–$C_6$ haloalkyl group, a $C_1$–$C_6$ alkoxy group, a cyano group and/or a nitro group), a $C_1$–$C_6$ alkoxy group, or $NR^{15}R^{16}$ (where $R^{15}$ and $R^{16}$ each independently represent a hydrogen atom, a $C_1$–$C_6$ alkyl group or a phenyl group (the phenyl group may be optionally substituted by a halogen atom, a $C_1$–$C_6$ alkyl group, a $C_1$–$C_6$ haloalkyl group, a $C_1$–$C_6$ alkoxy group, a cyano group and/or a nitro group)))}, $SR^{10}$ (where $R^{10}$ represents a hydrogen atom, a $C_1$–$C_6$ alkyl group, a $C_2$–$C_6$ alkenyl group, a $C_2$–$C_6$ alkynyl group, a $C_7$–$C_{12}$ aralkyl group (the aralkyl group may be optionally substituted by a halogen atom, a $C_1$–$C_6$ alkyl group, a $C_1$–$C_6$ haloalkyl group, a $C_1$–$C_6$ alkoxy group, a cyano group and/or a nitro group), $NR^{11}R^{12}$ {where $R^{11}$ and $R^{12}$ each independently represent a hydrogen atom, a $C_1$–$C_6$ alkyl group, a phenyl group (the phenyl group may be optionally substituted by a halogen atom, a $C_1$–$C_6$ alkyl group, a $C_1$–$C_6$ haloalkyl group, a $C_1$–$C_6$ alkoxy group, a cyano group and/or a nitro group) or $COR^{17}$ (where $R^{17}$ represents a $C_1$–$C_6$ alkyl group, a phenyl group (the phenyl group may be optionally substituted by a halogen atom, a $C_1$–$C_6$ alkyl group, a $C_1$–$C_6$ haloalkyl group, a $C_1$–$C_6$ alkoxy group, a cyano group and/or a nitro group) or $C_1$–$C_6$ alkoxy group)}, =O, =$NR^{13}$ {where $R^{13}$ represents a $C_1$–$C_6$ alkyl group, a phenyl group (the phenyl group may be optionally substituted by a halogen atom, a $C_1$–$C_6$ alkyl group, a $C_1$–$C_6$ haloalkyl group, a $C_1$–$C_6$ alkoxy group, a cyano group and/or a nitro group) or $OR^{18}$ (where $R^{18}$ represents a hydrogen atom, a $C_1$–$C_6$ alkyl group or $COR^{19}$ (where $R^{19}$ represents a $C_1$–$C_6$ alkyl group, a phenyl group (the phenyl group may be optionally substituted by a halogen atom, a $C_1$–$C_6$ alkyl group, a $C_1$–$C_6$ haloalkyl group, a $C_1$–$C_6$ alkoxy group, a cyano group and/or a nitro group) or $NR^{20}R^{21}$ (where $R^{20}$ and $R^{21}$ each independently represent a hydrogen atom, a $C_1$–$C_6$ alkyl group, a phenyl group (the phenyl group may be optionally substituted by a halogen atom, a $C_1$–$C_6$ alkyl group, a $C_1$–$C_6$ haloalkyl group, a $C_1$–$C_6$ alkoxy group, a cyano group and/or a nitro group))))}, and

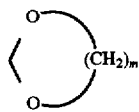

(where m is an integer of from 2 to 4);

the symbol ══ represents a single or double bond, and when it is a double bond, then $R^1$ and $R^3$ each independently may represent an oxygen atom;

provided that the case where all of $R^0$, $R^1$, $R^2$, $R^3$ and $R^4$ represent hydrogen atoms at the same time is excluded.

The details of the substituents as referred to herein are mentioned below.

The halogen atom includes fluorine, chlorine, bromine and iodine atoms, but preferably fluorine, chlorine and bromine atoms.

Examples of the $C_1$–$C_{10}$ alkyl group include methyl, ethyl, propyl, i-propyl, butyl, i-butyl, s-butyl, t-butyl, pentyl, hexyl, heptyl, octyl, nonyl and decyl groups.

Examples of the $C_2$–$C_{10}$ alkenyl group include ethenyl, allyl, 1-butenyl, 2-butenyl, 3-butenyl, 1-pentenyl, 2-pentenyl, 3-pentenyl, 4-pentenyl, 2,4-pentadienyl, 1-hexenyl, 2-hexenyl, 3-hexenyl, 4-hexenyl, 5-hexenyl, 2,4-hexadienyl, 1-heptenyl, 1-octenyl, 1-nonenyl and 1-decenyl groups.

Examples of the $C_2$–$C_{10}$ alkynyl group include ethynyl, propargyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 1-octynyl, 1-nonynyl and 1-decynyl groups.

Examples of the $C_1$–$C_6$ alkyl group include methyl, ethyl, propyl, i-propyl, butyl, i-butyl, s-butyl, t-butyl, pentyl and hexyl groups.

Examples of the $C_2$–$C_6$ alkenyl group include ethenyl, allyl, 1-butenyl, 2-butenyl, 3-butenyl, 1-pentenyl, 2-pentenyl, 3-pentenyl, 4-pentenyl, 2,4-pentadienyl, 1-hexenyl, 2-hexenyl, 3-hexenyl, 4-hexenyl, 5-hexenyl and 2,4-hexadienyl groups.

Examples of the $C_2$–$C_6$ alkynyl group include ethynyl, propargyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl groups.

Examples of the $C_1$–$C_6$ haloalkyl group include fluoromethyl, difluoromethyl, trifluoromethyl, chloromethyl, bromomethyl, trifluoroethyl, trichloroethyl, trifluoropropyl, trifluorobutyl, trifluoropentyl and trifluorohexyl groups.

Examples of the $C_1$–$C_6$ alkoxy group include methoxy, ethoxy, propoxy, i-propoxy, butoxy, i-butoxy, s-butoxy, t-butoxy, pentyloxy and hexyloxy groups.

Examples of the $C_2$–$C_{10}$ alkoxyalkyl group include methoxymethyl, ethoxymethyl, propoxymethyl, butoxymethyl, hexyloxymethyl, octyloxymethyl, methoxyethyl, ethoxyethyl, propoxyethyl, methoxypropyl, ethoxypropyl, propoxypropyl, methoxyethoxyethyl, ethoxyethoxymethyl, propoxyethoxymethyl, butoxyethoxymethyl, hexyloxyethoxymethyl, ethoxyethoxyethyl, butoxyethoxyethyl, hexyloxyethoxyethyl, ethoxyethoxypropyl, ethoxyethoxybutyl and tetrahydropyranyl groups.

Examples of the silyl group include trimethylsilyl and t-butyldimethylsilyl groups.

Examples of the $C_1$–$C_4$ alkylsulfonyl group include methanesulfonyl, ethanesulfonyl, propanesulfonyl and butanesulfonyl groups.

Examples of the phosphoryl group include dimethylphosphoryl, diethylphosphoryl and diphenylphosphoryl groups.

Examples of the $C_7$–$C_{12}$ aralkyl group include benzyl, 1-phenylethyl, 2-phenylethyl, 1-phenylpropyl and 3-phenylpropyl groups.

In the formula (1), several stereoisomers and optical isomers, which shall naturally be within the scope of the present invention, are included.

Preferably, $R^1$ represents an optionally-substituted alkyl group or an optionally-substituted alkenyl group. The substituent, if any, in the group is preferably selected from a halogen atom, a $C_1$–$C_6$ alkyl group, —$OR^{27}$ (where $R^{27}$ represents a hydrogen atom, a $C_1$–$C_6$ alkyl group, a $C_1$–$C_6$ haloalkyl group, a silyl group, a $C_1$–$C_4$ alkylsulfonyl group, an aralkyl group (the aralkyl group may be optionally substituted by a halogen atom, a $C_1$–$C_6$ alkyl group, a $C_1$–$C_6$ haloalkyl group, a $C_1$–$C_6$ alkoxy group, a cyano group and/or a nitro group), a $C_2$–$C_{10}$ alkoxyalkyl group or $COR^{28}$ (where $R^{28}$ represents a $C_1$–$C_6$ alkyl group, a phenyl group (the phenyl group may be optionally substituted by a halogen atom, a $C_1$–$C_6$ alkyl group, a $C_1$–$C_6$ haloalkyl group, a $C_1$–$C_6$ alkoxy group, a cyano group and/or a nitro group), $C_1$–$C_6$ alkoxy group or $NR^{29}R^{30}$ (where $R^{29}$ and $R^{30}$ each independently represent a hydrogen atom, a $C_1$–$C_6$ alkyl group or a phenyl group (the phenyl group may be optionally substituted by a halogen atom, a $C_1$–$C_6$ alkyl group, a $C_1$–$C_6$ haloalkyl group, a $C_1$–$C_6$ alkoxy group, a cyano group and/or a nitro group)))}, =O and a group of:

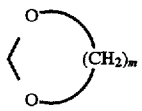

(where m is an integer of from 2 to 4).

Preferably, $R^0$, $R^2$ and $R^4$ each independently represent a hydrogen atom, a halogen atom, a hydroxyl group or a $C_1$–$C_{10}$ alkyl group.

Preferably, $R^4$ represents a hydrogen atom, a halogen atom or a $C_1$–$C_{10}$ alkyl group.

Preferably, $A^1$, $A^2$, $A^3$ and $A^4$ each independently represent —$COOR^{22}$ (where $R^{22}$ represents a hydrogen atom or a $C_1$–$C_{10}$ alkyl group), or $A^1$ and $A^2$, and $A^3$ and $A^4$ are combined together to represent a group of:

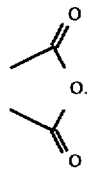

Preferably, the symbol ══ represents a single bond.

Preferred examples of the compounds of the present invention are mentioned below.

(1) Cyclooctadiene derivatives of formula (1) wherein $R^0$, $R^2$ and $R^3$ each independently represent a hydrogen atom, a halogen atom, a hydroxyl group or a $C_1$–$C_{10}$ alkyl group, or $R^3$ represents =O.

(2) Cyclooctadiene derivatives of the above-mentioned wherein $R^4$ represents a hydrogen atom, a halogen atom or a $C_1$–$C_{10}$ alkyl group.

(3) Cyclooctadiene derivatives of the above-mentioned (2) wherein $A^1$, $A^2$, $A^3$ and $A^4$ each independently represent $COOR^{22}$ (where $R^{22}$ represents a hydrogen atom or a $C_1$–$C_{10}$ alkyl group), or $A^1$ and $A^2$, and $A^3$ and $A^4$ are combined together to represent a group of:

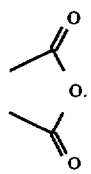

(4) Cyclooctadiene derivatives of the above-mentioned (3), wherein $R^0$, $R^2$ and $R^3$ represent hydrogen atoms; $R^4$ represents —$CH_2CH_2CH_2CH_3$;

$R^1$ represents a group of:

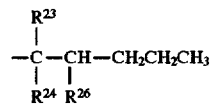

or a group of:

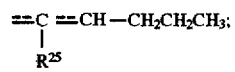

$R^{23}$ represents a hydrogen atom, a halogen atom, a $C_1$–$C_6$ alkyl group or a $C_1$–$C_6$ alkoxy group;

$R^{24}$ represents a hydrogen atom, a halogen atom, a $C_1$–$C_6$ alkyl group, —$OR^{27}$ {where $R^{27}$ represents a hydrogen atom, $C_1$–$C_6$ alkyl group, a $C_1$–$C_6$ haloalkyl group, a $C_7$–$C_{12}$ aralkyl group (the aralkyl group may be optionally substituted by a halogen atom, a $C_1$–$C_6$ alkyl group, a $C_1$–$C_6$ haloalkyl group, a $C_1$–$C_6$ alkoxy group, a cyano group and/or a nitro group), a $C_2$–$C_6$ alkoxyalkyl group or —$COR^{28}$ (where $R^{28}$ represents a $C_1$–$C_6$ alkyl group, a phenyl group (the phenyl group may be optionally substituted by a halogen atom, a $C_1$–$C_6$ alkyl group, a $C_1$–$C_6$ haloalkyl group, a $C_1$–$C_6$ alkoxy group, a cyano group and/or a nitro group), a $C_1$–$C_6$ alkoxy group or $NR^{29}R^{30}$ (where $R^{29}$ and $R^{30}$ each independently represent a hydrogen atom, a $C_1$–$C_6$ alkyl group or a phenyl group (the phenyl group may be optionally substituted by a halogen atom, a $C_1$–$C_6$ alkyl group, a $C_1$–$C_6$ haloalkyl group, a $C_1$–$C_6$ alkoxy group, a cyano group and/or a nitro group)))}, or $R^{23}$ and $R^{24}$ are combined together to represent =O or a group of:

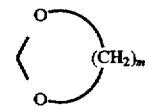

(where m is an integer of from 2 to 4);

$R^{25}$ represents a hydrogen atom, a halogen atom or a $C_1$–$C_6$ alkyl group;

$R^{26}$ represents a hydrogen atom, a halogen atom or a $C_1$–$C_6$ alkyl group; and the symbol ══ represents a single or double bond.

(5) Compound of formula (2):

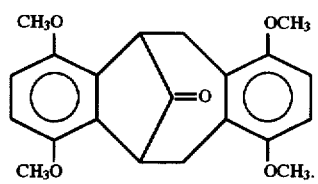

(6) Compound of formula (3):

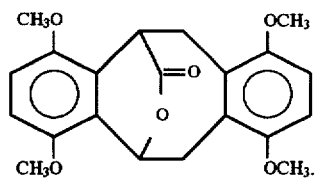

(7) Compounds of formula (4):

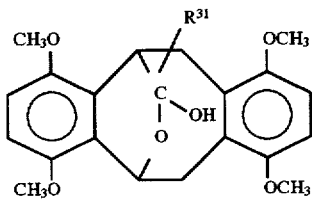
(4)

wherein $R^{31}$ represents a $C_1$–$C_{10}$ alkyl group or a $C_2$–$C_{10}$ alkenyl group.

In the present specification, "i" means "iso"; "s" means "secondary"; "Me" means "methyl group"; "Et" means "ethyl group"; "Pr" means "propyl group"; "Bu" means "butyl group", "Pen" means "pentyl group"; "Hex" means "hexyl group"; "Ph" means "phenyl group", and "Hal" means "halogen atom".

Typical examples of the compounds of formula (1) of the present invention are mentioned below, which, however, are not intended to restrict the scope of the present invention.

TABLE 1

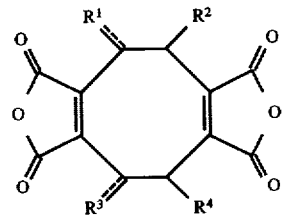

| $R^1$ | $R^2$ | $R^3$ | $R^4$ |
|---|---|---|---|
| Me | H | H | H |
| Et | H | H | H |
| Pr | H | H | H |
| i-Pr | H | H | H |
| Bu | H | H | H |
| i-Bu | H | H | H |
| s-Bu | H | H | H |
| Pen | H | H | H |
| Hex | H | H | H |
| $(CH_2)_6CH_3$ | H | H | H |
| $(CH_2)_7CH_3$ | H | H | H |
| $(CH_2)_8CH_3$ | H | H | H |
| $(CH_2)_9CH_3$ | H | H | H |
| Me | H | H | Me |
| Et | H | H | Me |
| Pr | H | H | Me |
| i-Pr | H | H | Me |
| Bu | H | H | Me |
| i-Bu | H | H | Me |
| s-Bu | H | H | Me |
| Pen | H | H | Me |
| Hex | H | H | Me |
| $(CH_2)_6CH_3$ | H | H | Me |
| $(CH_2)_7CH_3$ | H | H | Me |
| $(CH_2)_8CH_3$ | H | H | Me |
| $(CH_2)_9CH_3$ | H | H | Me |
| Et | H | H | Et |
| Pr | H | H | Et |
| i-Pr | H | H | Et |
| Bu | H | H | Et |
| i-Bu | H | H | Et |
| s-Bu | H | H | Et |
| Pen | H | H | Et |
| Hex | H | H | Et |
| $(CH_2)_6CH_3$ | H | H | Et |
| $(CH_2)_7CH_3$ | H | H | Et |
| $(CH_2)_8CH_3$ | H | H | Et |
| $(CH_2)_9CH_3$ | H | H | Et |
| Pr | H | H | Pr |
| i-Pr | H | H | Pr |
| Bu | H | H | Pr |
| i-Bu | H | H | Pr |
| s-Bu | H | H | Pr |
| Pen | H | H | Pr |
| Hex | H | H | Pr |
| $(CH_2)_6CH_3$ | H | H | Pr |
| $(CH_2)_7CH_3$ | H | H | Pr |
| $(CH_2)_8CH_3$ | H | H | Pr |
| $(CH_2)_9CH_3$ | H | H | Pr |
| Bu | H | H | Bu |
| Pen | H | H | Bu |
| Hex | H | H | Bu |

TABLE 1-continued

| R¹ | R² | R³ | R⁴ |
|---|---|---|---|
| (CH₂)₆CH₃ | H | H | Bu |
| (CH₂)₇CH₃ | H | H | Bu |
| (CH₂)₈CH₃ | H | H | Bu |
| (CH₂)₉CH₃ | H | H | Bu |
| Pen | H | H | Pen |
| Hex | H | H | Pen |
| (CH₂)₆CH₃ | H | H | Pen |
| (CH₂)₇CH₃ | H | H | Pen |
| (CH₂)₈CH₃ | H | H | Pen |
| (CH₂)₉CH₃ | H | H | Pen |
| Hex | H | H | Hex |
| (CH₂)₆CH₃ | H | H | Hex |
| (CH₂)₇CH₃ | H | H | Hex |
| (CH₂)₈CH₃ | H | H | Hex |
| (CH₂)₉CH₃ | H | H | Hex |
| (CH₂)₆CH₃ | H | H | (CH₂)₆CH₃ |
| (CH₂)₇CH₃ | H | H | (CH₂)₆CH₃ |
| (CH₂)₈CH₃ | H | H | (CH₂)₆CH₃ |
| (CH₂)₉CH₃ | H | H | (CH₂)₆CH₃ |
| (CH₂)₇CH₃ | H | H | (CH₂)₇CH₃ |
| (CH₂)₈CH₃ | H | H | (CH₂)₇CH₃ |
| (CH₂)₉CH₃ | H | H | (CH₂)₇CH₃ |
| (CH₂)₈CH₃ | H | H | (CH₂)₈CH₃ |
| (CH₂)₉CH₃ | H | H | (CH₂)₈CH₃ |
| (CH₂)₉CH₃ | H | H | (CH₂)₉CH₃ |
| Me | Me | H | H |
| Et | Me | H | H |
| Pr | Me | H | H |
| i-Pr | Me | H | H |
| Bu | Me | H | H |
| i-Bu | Me | H | H |
| s-Bu | Me | H | H |
| Pen | Me | H | H |
| Hex | Me | H | H |
| (CH₂)₆CH₃ | Me | H | H |
| (CH₂)₇CH₃ | Me | H | H |
| (CH₂)₈CH₃ | Me | H | H |
| (CH₂)₉CH₃ | Me | H | H |
| Et | Et | H | H |
| Pr | Et | H | H |
| i-Pr | Et | H | H |
| Bu | Et | H | H |
| i-Bu | Et | H | H |
| s-Bu | Et | H | H |
| Pen | Et | H | H |
| Hex | Et | H | H |
| (CH₂)₆CH₃ | Et | H | H |
| (CH₂)₇CH₃ | Et | H | H |
| (CH₂)₈CH₃ | Et | H | H |
| (CH₂)₉CH₃ | Et | H | H |
| Pr | Pr | H | H |
| i-Pr | Pr | H | H |
| Bu | Pr | H | H |
| i-Bu | Pr | H | H |
| s-Bu | Pr | H | H |
| Pen | Pr | H | H |
| Hex | Pr | H | H |
| (CH₂)₆CH₃ | Pr | H | H |
| (CH₂)₇CH₃ | Pr | H | H |
| (CH₂)₈CH₃ | Pr | H | H |
| (CH₂)₉CH₃ | Pr | H | H |
| i-Pr | Bu | H | H |
| Bu | Bu | H | H |
| i-Bu | Bu | H | H |
| s-Bu | Bu | H | H |
| Pen | Bu | H | H |

TABLE 1-continued

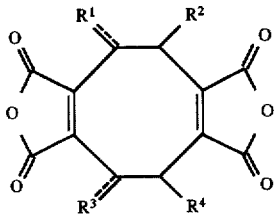

| R¹ | R² | R³ | R⁴ |
|---|---|---|---|
| Hex | Bu | H | H |
| (CH₂)₆CH₃ | Bu | H | H |
| (CH₂)₇CH₃ | Bu | H | H |
| (CH₂)₈CH₃ | Bu | H | H |
| (CH₂)₉CH₃ | Bu | H | H |
| i-Bu | Pen | H | H |
| s-Bu | Pen | H | H |
| Pen | Pen | H | H |
| Hex | Pen | H | H |
| (CH₂)₆CH₃ | Pen | H | H |
| (CH₂)₇CH₃ | Pen | H | H |
| (CH₂)₈CH₃ | Pen | H | H |
| (CH₂)₉CH₃ | Pen | H | H |
| Hex | Hex | H | H |
| (CH₂)₆CH₃ | Hex | H | H |
| (CH₂)₇CH₃ | Hex | H | H |
| (CH₂)₈CH₃ | Hex | H | H |
| (CH₂)₉CH₃ | Hex | H | H |
| (CH₂)₆CH₃ | (CH₂)₆CH₃ | H | H |
| (CH₂)₇CH₃ | (CH₂)₆CH₃ | H | H |
| (CH₂)₈CH₃ | (CH₂)₆CH₃ | H | H |
| (CH₂)₉CH₃ | (CH₂)₆CH₃ | H | H |
| (CH₂)₇CH₃ | (CH₂)₇CH₃ | H | H |
| (CH₂)₈CH₃ | (CH₂)₇CH₃ | H | H |
| (CH₂)₉CH₃ | (CH₂)₇CH₃ | H | H |
| (CH₂)₈CH₃ | (CH₂)₈CH₃ | H | H |
| (CH₂)₉CH₃ | (CH₂)₈CH₃ | H | H |
| (CH₂)₉CH₃ | (CH₂)₉CH₃ | H | H |
| Me | H | Me | H |
| Et | H | Me | H |
| Pr | H | Me | H |
| i-Pr | H | Me | H |
| Bu | H | Me | H |
| i-Bu | H | Me | H |
| s-Bu | H | Me | H |
| Pen | H | Me | H |
| Hex | H | Me | H |
| (CH₂)₆CH₃ | H | Me | H |
| (CH₂)₇CH₃ | H | Me | H |
| (CH₂)₈CH₃ | H | Me | H |
| (CH₂)₉CH₃ | H | Me | H |
| Et | H | Et | H |
| Pr | H | Et | H |
| i-Pr | H | Et | H |
| Bu | H | Et | H |
| i-Bu | H | Et | H |
| s-Bu | H | Et | H |
| Pen | H | Et | H |
| Hex | H | Et | H |
| (CH₂)₆CH₃ | H | Et | H |
| (CH₂)₇CH₃ | H | Et | H |
| (CH₂)₈CH₃ | H | Et | H |
| (CH₂)₉CH₃ | H | Et | H |
| Pr | H | Pr | H |
| i-Pr | H | Pr | H |
| Bu | H | Pr | H |
| i-Bu | H | Pr | H |
| s-Bu | H | Pr | H |
| Pen | H | Pr | H |
| Hex | H | Pr | H |
| (CH₂)₆CH₃ | H | Pr | H |
| (CH₂)₇CH₃ | H | Pr | H |
| (CH₂)₈CH₃ | H | Pr | H |
| (CH₂)₉CH₃ | H | Pr | H |
| i-Pr | H | Bu | H |
| Bu | H | Bu | H |

TABLE 1-continued

[Structure: cyclooctatetraene-based bis(anhydride) with substituents R¹, R², R³, R⁴]

| R¹ | R² | R³ | R⁴ |
|---|---|---|---|
| i-Bu | H | Bu | H |
| s-Bu | H | Bu | H |
| Pen | H | Bu | H |
| Hex | H | Bu | H |
| (CH$_2$)$_6$CH$_3$ | H | Bu | H |
| (CH$_2$)$_7$CH$_3$ | H | Bu | H |
| (CH$_2$)$_8$CH$_3$ | H | Bu | H |
| (CH$_2$)$_9$CH$_3$ | H | Bu | H |
| i-Bu | H | Pen | H |
| s-Bu | H | Pen | H |
| Pen | H | Pen | H |
| Hex | H | Pen | H |
| (CH$_2$)$_6$CH$_3$ | H | Pen | H |
| (CH$_2$)$_7$CH$_3$ | H | Pen | H |
| (CH$_2$)$_8$CH$_3$ | H | Pen | H |
| (CH$_2$)$_9$CH$_3$ | H | Pen | H |
| Hex | H | Hex | H |
| (CH$_2$)$_6$CH$_3$ | H | Hex | H |
| (CH$_2$)$_7$CH$_3$ | H | Hex | H |
| (CH$_2$)$_8$CH$_3$ | H | Hex | H |
| (CH$_2$)$_9$CH$_3$ | H | Hex | H |
| (CH$_2$)$_6$CH$_3$ | H | (CH$_2$)$_6$CH$_3$ | H |
| (CH$_2$)$_7$CH$_3$ | H | (CH$_2$)$_6$CH$_3$ | H |
| (CH$_2$)$_8$CH$_3$ | H | (CH$_2$)$_6$CH$_3$ | H |
| (CH$_2$)$_9$CH$_3$ | H | (CH$_2$)$_6$CH$_3$ | H |
| (CH$_2$)$_7$CH$_3$ | H | (CH$_2$)$_7$CH$_3$ | H |
| (CH$_2$)$_8$CH$_3$ | H | (CH$_2$)$_7$CH$_3$ | H |
| (CH$_2$)$_9$CH$_3$ | H | (CH$_2$)$_7$CH$_3$ | H |
| (CH$_2$)$_8$CH$_3$ | H | (CH$_2$)$_8$CH$_3$ | H |
| (CH$_2$)$_9$CH$_3$ | H | (CH$_2$)$_8$CH$_3$ | H |
| (CH$_2$)$_9$CH$_3$ | H | (CH$_2$)$_9$CH$_3$ | H |
| Me | Me | Me | H |
| Et | Me | Me | H |
| Pr | Me | Me | H |
| i-Pr | Me | Me | H |
| Bu | Me | Me | H |
| i-Bu | Me | Me | H |
| s-Bu | Me | Me | H |
| Pen | Me | Me | H |
| Hex | Me | Me | H |
| (CH$_2$)$_6$CH$_3$ | Me | Me | H |
| (CH$_2$)$_7$CH$_3$ | Me | Me | H |
| (CH$_2$)$_8$CH$_3$ | Me | Me | H |
| (CH$_2$)$_9$CH$_3$ | Me | Me | H |
| Me | Et | Me | H |
| Et | Et | Me | H |
| Pr | Et | Me | H |
| i-Pr | Et | Me | H |
| Bu | Et | Me | H |
| i-Bu | Et | Me | H |
| s-Bu | Et | Me | H |
| Pen | Et | Me | H |
| Hex | Et | Me | H |
| (CH$_2$)$_6$CH$_3$ | Et | Me | H |
| (CH$_2$)$_7$CH$_3$ | Et | Me | H |
| (CH$_2$)$_8$CH$_3$ | Et | Me | H |
| (CH$_2$)$_9$CH$_3$ | Et | Me | H |
| Me | Pr | Me | H |
| Et | Pr | Me | H |
| Pr | Pr | Me | H |
| i-Pr | Pr | Me | H |
| Bu | Pr | Me | H |
| i-Bu | Pr | Me | H |
| s-Bu | Pr | Me | H |
| Pen | Pr | Me | H |
| Hex | Pr | Me | H |

TABLE 1-continued

| R¹ | R² | R³ | R⁴ |
|---|---|---|---|
| (CH₂)₆CH₃ | Pr | Me | H |
| (CH₂)₇CH₃ | Pr | Me | H |
| (CH₂)₈CH₃ | Pr | Me | H |
| (CH₂)₉CH₃ | Pr | Me | H |
| Me | Bu | Me | H |
| Et | Bu | Me | H |
| Pr | Bu | Me | H |
| i-Pr | Bu | Me | H |
| Bu | Bu | Me | H |
| i-Bu | Bu | Me | H |
| s-Bu | Bu | Me | H |
| Pen | Bu | Me | H |
| Hex | Bu | Me | H |
| (CH₂)₆CH₃ | Bu | Me | H |
| (CH₂)₇CH₃ | Bu | Me | H |
| (CH₂)₈CH₃ | Bu | Me | H |
| (CH₂)₉CH₃ | Bu | Me | H |
| Me | Pen | Me | H |
| Et | Pen | Me | H |
| Pr | Pen | Me | H |
| i-Pr | Pen | Me | H |
| Bu | Pen | Me | H |
| i-Bu | Pen | Me | H |
| s-Bu | Pen | Me | H |
| Pen | Pen | Me | H |
| Hex | Pen | Me | H |
| (CH₂)₆CH₃ | Pen | Me | H |
| (CH₂)₇CH₃ | Pen | Me | H |
| (CH₂)₈CH₃ | Pen | Me | H |
| (CH₂)₉CH₃ | Pen | Me | H |
| Me | Hex | Me | H |
| Et | Hex | Me | H |
| Pr | Hex | Me | H |
| i-Pr | Hex | Me | H |
| Bu | Hex | Me | H |
| i-Bu | Hex | Me | H |
| s-Bu | Hex | Me | H |
| Pen | Hex | Me | H |
| Hex | Hex | Me | H |
| (CH₂)₆CH₃ | Hex | Me | H |
| (CH₂)₇CH₃ | Hex | Me | H |
| (CH₂)₈CH₃ | Hex | Me | H |
| (CH₂)₉CH₃ | Hex | Me | H |
| Me | (CH₂)₇CH₃ | Me | H |
| Et | (CH₂)₇CH₃ | Me | H |
| Pr | (CH₂)₇CH₃ | Me | H |
| i-Pr | (CH₂)₇CH₃ | Me | H |
| Bu | (CH₂)₇CH₃ | Me | H |
| i-Bu | (CH₂)₇CH₃ | Me | H |
| s-Bu | (CH₂)₇CH₃ | Me | H |
| Pen | (CH₂)₇CH₃ | Me | H |
| Hex | (CH₂)₇CH₃ | Me | H |
| (CH₂)₆CH₃ | (CH₂)₇CH₃ | Me | H |
| (CH₂)₇CH₃ | (CH₂)₇CH₃ | Me | H |
| (CH₂)₈CH₃ | (CH₂)₇CH₃ | Me | H |
| (CH₂)₉CH₃ | (CH₂)₇CH₃ | Me | H |
| Me | (CH₂)₉CH₃ | Me | H |
| Et | (CH₂)₉CH₃ | Me | H |
| Pr | (CH₂)₉CH₃ | Me | H |
| i-Pr | (CH₂)₉CH₃ | Me | H |
| Bu | (CH₂)₉CH₃ | Me | H |
| i-Bu | (CH₂)₉CH₃ | Me | H |
| s-Bu | (CH₂)₉CH₃ | Me | H |
| Pen | (CH₂)₉CH₃ | Me | H |
| Hex | (CH₂)₉CH₃ | Me | H |
| (CH₂)₆CH₃ | (CH₂)₉CH₃ | Me | H |

TABLE 1-continued

| R¹ | R² | R³ | R⁴ |
|---|---|---|---|
| (CH₂)₇CH₃ | (CH₂)₉CH₃ | Me | H |
| (CH₂)₈CH₃ | (CH₂)₉CH₃ | Me | H |
| (CH₂)₉CH₃ | (CH₂)₉CH₃ | Me | H |
| Me | Me | Et | H |
| Et | Me | Et | H |
| Pr | Me | Et | H |
| Bu | Me | Et | H |
| Pen | Me | Et | H |
| Hex | Me | Et | H |
| (CH₂)₇CH₃ | Me | Et | H |
| (CH₂)₉CH₃ | Me | Et | H |
| Me | Et | Et | H |
| Et | Et | Et | H |
| Pr | Et | Et | H |
| Bu | Et | Et | H |
| Pen | Et | Et | H |
| Hex | Et | Et | H |
| (CH₂)₇CH₃ | Et | Et | H |
| (CH₂)₉CH₃ | Et | Et | H |
| Me | Pr | Et | H |
| Et | Pr | Et | H |
| Pr | Pr | Et | H |
| Bu | Pr | Et | H |
| Pen | Pr | Et | H |
| Hex | Pr | Et | H |
| (CH₂)₇CH₃ | Pr | Et | H |
| (CH₂)₉CH₃ | Pr | Et | H |
| Me | Bu | Et | H |
| Et | Bu | Et | H |
| Pr | Bu | Et | H |
| Bu | Bu | Et | H |
| Pen | Bu | Et | H |
| Hex | Bu | Et | H |
| (CH₂)₇CH₃ | Bu | Et | H |
| (CH₂)₉CH₃ | Bu | Et | H |
| Me | Pen | Et | H |
| Et | Pen | Et | H |
| Pr | Pen | Et | H |
| Bu | Pen | Et | H |
| Pen | Pen | Et | H |
| Hex | Pen | Et | H |
| (CH₂)₇CH₃ | Pen | Et | H |
| (CH₂)₉CH₃ | Pen | Et | H |
| Me | Hex | Et | H |
| Et | Hex | Et | H |
| Pr | Hex | Et | H |
| Bu | Hex | Et | H |
| Pen | Hex | Et | H |
| Hex | Hex | Et | H |
| (CH₂)₇CH₃ | Hex | Et | H |
| (CH₂)₉CH₃ | Hex | Et | H |
| Me | Me | Pr | H |
| Et | Me | Pr | H |
| Pr | Me | Pr | H |
| Bu | Me | Pr | H |
| Pen | Me | Pr | H |
| Hex | Me | Pr | H |
| (CH₂)₇CH₃ | Me | Pr | H |
| (CH₂)₉CH₃ | Me | Pr | H |
| Me | Et | Pr | H |
| Et | Et | Pr | H |
| Pr | Et | Pr | H |
| Bu | Et | Pr | H |
| Pen | Et | Pr | H |
| Hex | Et | Pr | H |
| (CH₂)₇CH₃ | Et | Pr | H |

TABLE 1-continued

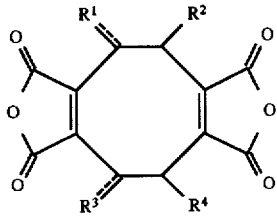

| R¹ | R² | R³ | R⁴ |
|---|---|---|---|
| (CH₂)₉CH₃ | Et | Pr | H |
| Me | Pr | Pr | H |
| Et | Pr | Pr | H |
| Pr | Pr | Pr | H |
| Bu | Pr | Pr | H |
| Pen | Pr | Pr | H |
| Hex | Pr | Pr | H |
| (CH₂)₇CH₃ | Pr | Pr | H |
| (CH₂)₉CH₃ | Pr | Pr | H |
| Me | Bu | Pr | H |
| Et | Bu | Pr | H |
| Pr | Bu | Pr | H |
| Bu | Bu | Pr | H |
| Pen | Bu | Pr | H |
| Hex | Bu | Pr | H |
| (CH₂)₇CH₃ | Bu | Pr | H |
| (CH₂)₉CH₃ | Bu | Pr | H |
| Me | Pen | Pr | H |
| Et | Pen | Pr | H |
| Pr | Pen | Pr | H |
| Bu | Pen | Pr | H |
| Pen | Pen | Pr | H |
| Hex | Pen | Pr | H |
| (CH₂)₇CH₃ | Pen | Pr | H |
| (CH₂)₉CH₃ | Pen | Pr | H |
| Me | Hex | Pr | H |
| Et | Hex | Pr | H |
| Pr | Hex | Pr | H |
| Bu | Hex | Pr | H |
| Pen | Hex | Pr | H |
| Hex | Hex | Pr | H |
| (CH₂)₇CH₃ | Hex | Pr | H |
| (CH₂)₉CH₃ | Hex | Pr | H |
| Me | Me | Bu | H |
| Et | Me | Bu | H |
| Pr | Me | Bu | H |
| Bu | Me | Bu | H |
| Pen | Me | Bu | H |
| Hex | Me | Bu | H |
| (CH₂)₇CH₃ | Me | Bu | H |
| (CH₂)₉CH₃ | Me | Bu | H |
| Me | Et | Bu | H |
| Et | Et | Bu | H |
| Pr | Et | Bu | H |
| Bu | Et | Bu | H |
| Pen | Et | Bu | H |
| Hex | Et | Bu | H |
| (CH₂)₇CH₃ | Et | Bu | H |
| (CH₂)₉CH₃ | Et | Bu | H |
| Me | Pr | Bu | H |
| Et | Pr | Bu | H |
| Pr | Pr | Bu | H |
| Bu | Pr | Bu | H |
| Pen | Pr | Bu | H |
| Hex | Pr | Bu | H |
| (CH₂)₇CH₃ | Pr | Bu | H |
| (CH₂)₉CH₃ | Pr | Bu | H |
| Me | Bu | Bu | H |
| Et | Bu | Bu | H |
| Pr | Bu | Bu | H |
| Bu | Bu | Bu | H |
| Pen | Bu | Bu | H |
| Hex | Bu | Bu | H |
| (CH₂)₇CH₃ | Bu | Bu | H |
| (CH₂)₉CH₃ | Bu | Bu | H |
| Me | Pen | Bu | H |

TABLE 1-continued

| R¹ | R² | R³ | R⁴ |
|---|---|---|---|
| Et | Pen | Bu | H |
| Pr | Pen | Bu | H |
| Bu | Pen | Bu | H |
| Pen | Pen | Bu | H |
| Hex | Pen | Bu | H |
| (CH$_2$)$_7$CH$_3$ | Pen | Bu | H |
| (CH$_2$)$_9$CH$_3$ | Pen | Bu | H |
| Me | Hex | Bu | H |
| Et | Hex | Bu | H |
| Pr | Hex | Bu | H |
| Bu | Hex | Bu | H |
| Pen | Hex | Bu | H |
| Hex | Hex | Bu | H |
| (CH$_2$)$_7$CH$_3$ | Hex | Bu | H |
| (CH$_2$)$_9$CH$_3$ | Hex | Bu | H |
| Me | Me | Pen | H |
| Et | Me | Pen | H |
| Pr | Me | Pen | H |
| Bu | Me | Pen | H |
| Pen | Me | Pen | H |
| Hex | Me | Pen | H |
| (CH$_2$)$_7$CH$_3$ | Me | Pen | H |
| (CH$_2$)$_9$CH$_3$ | Me | Pen | H |
| Me | Et | Pen | H |
| Et | Et | Pen | H |
| Pr | Et | Pen | H |
| Bu | Et | Pen | H |
| Pen | Et | Pen | H |
| Hex | Et | Pen | H |
| (CH$_2$)$_7$CH$_3$ | Et | Pen | H |
| (CH$_2$)$_9$CH$_3$ | Et | Pen | H |
| Me | Pr | Pen | H |
| Et | Pr | Pen | H |
| Pr | Pr | Pen | H |
| Bu | Pr | Pen | H |
| Pen | Pr | Pen | H |
| Hex | Pr | Pen | H |
| (CH$_2$)$_7$CH$_3$ | Pr | Pen | H |
| (CH$_2$)$_9$CH$_3$ | Pr | Pen | H |
| Me | Bu | Pen | H |
| Et | Bu | Pen | H |
| Pr | Bu | Pen | H |
| Bu | Bu | Pen | H |
| Pen | Bu | Pen | H |
| Hex | Bu | Pen | H |
| (CH$_2$)$_7$CH$_3$ | Bu | Pen | H |
| (CH$_2$)$_9$CH$_3$ | Bu | Pen | H |
| Me | Pen | Pen | H |
| Et | Pen | Pen | H |
| Pr | Pen | Pen | H |
| Bu | Pen | Pen | H |
| Pen | Pen | Pen | H |
| Hex | Pen | Pen | H |
| (CH$_2$)$_7$CH$_3$ | Pen | Pen | H |
| (CH$_2$)$_9$CH$_3$ | Pen | Pen | H |
| Me | Hex | Pen | H |
| Et | Hex | Pen | H |
| Pr | Hex | Pen | H |
| Bu | Hex | Pen | H |
| Pen | Hex | Pen | H |
| Hex | Hex | Pen | H |
| (CH$_2$)$_7$CH$_3$ | Hex | Pen | H |
| (CH$_2$)$_9$CH$_3$ | Hex | Pen | H |
| Me | Me | Hex | H |
| Et | Me | Hex | H |
| Pr | Me | Hex | H |

TABLE 1-continued

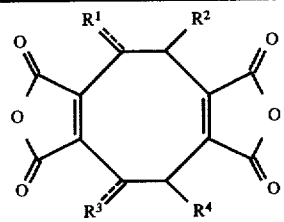

| R¹ | R² | R³ | R⁴ |
|---|---|---|---|
| Bu | Me | Hex | H |
| Pen | Me | Hex | H |
| Hex | Me | Hex | H |
| (CH₂)₇CH₃ | Me | Hex | H |
| (CH₂)₉CH₃ | Me | Hex | H |
| Me | Et | Hex | H |
| Et | Et | Hex | H |
| Pr | Et | Hex | H |
| Bu | Et | Hex | H |
| Pen | Et | Hex | H |
| Hex | Et | Hex | H |
| (CH₂)₇CH₃ | Et | Hex | H |
| (CH₂)₉CH₃ | Et | Hex | H |
| Me | Pr | Hex | H |
| Et | Pr | Hex | H |
| Pr | Pr | Hex | H |
| Bu | Pr | Hex | H |
| Pen | Pr | Hex | H |
| Hex | Pr | Hex | H |
| (CH₂)₇CH₃ | Pr | Hex | H |
| (CH₂)₉CH₃ | Pr | Hex | H |
| Me | Bu | Hex | H |
| Et | Bu | Hex | H |
| Pr | Bu | Hex | H |
| Bu | Bu | Hex | H |
| Pen | Bu | Hex | H |
| Hex | Bu | Hex | H |
| (CH₂)₇CH₃ | Bu | Hex | H |
| (CH₂)₉CH₃ | Bu | Hex | H |
| Me | Pen | Hex | H |
| Et | Pen | Hex | H |
| Pr | Pen | Hex | H |
| Bu | Pen | Hex | H |
| Pen | Pen | Hex | H |
| Hex | Pen | Hex | H |
| (CH₂)₇CH₃ | Pen | Hex | H |
| (CH₂)₉CH₃ | Pen | Hex | H |
| Me | Hex | Hex | H |
| Et | Hex | Hex | H |
| Pr | Hex | Hex | H |
| Bu | Hex | Hex | H |
| Pen | Hex | Hex | H |
| Hex | Hex | Hex | H |
| (CH₂)₇CH₃ | Hex | Hex | H |
| (CH₂)₉CH₃ | Hex | Hex | H |
| (CH₂)₇CH₃ | (CH₂)₇CH₃ | (CH₂)₇CH₃ | H |
| (CH₂)₉CH₃ | (CH₂)₉CH₃ | (CH₂)₉CH₃ | H |
| Me | Me | Me | Me |
| Et | Me | Me | Me |
| Pr | Me | Me | Me |
| Bu | Me | Me | Me |
| Pen | Me | Me | Me |
| Hex | Me | Me | Me |
| (CH₂)₇CH₃ | Me | Me | Me |
| (CH₂)₉CH₃ | Me | Me | Me |
| Et | Me | Me | Et |
| Pr | Me | Me | Et |
| Bu | Me | Me | Et |
| Pen | Me | Me | Et |
| Hex | Me | Me | Et |
| (CH₂)₇CH₃ | Me | Me | Et |
| (CH₂)₉CH₃ | Me | Me | Et |
| Pr | Me | Me | Pr |
| Bu | Me | Me | Pr |
| Pen | Me | Me | Pr |
| Hex | Me | Me | Pr |

TABLE 1-continued

| R¹ | R² | R³ | R⁴ |
|---|---|---|---|
| (CH₂)₇CH₃ | Me | Me | Pr |
| (CH₂)₉CH₃ | Me | Me | Pr |
| Bu | Me | Me | Bu |
| Pen | Me | Me | Bu |
| Hex | Me | Me | Bu |
| (CH₂)₇CH₃ | Me | Me | Bu |
| (CH₂)₉CH₃ | Me | Me | Bu |
| Pen | Me | Me | Pen |
| Hex | Me | Me | Pen |
| (CH₂)₇CH₃ | Me | Me | Pen |
| (CH₂)₉CH₃ | Me | Me | Pen |
| Hex | Me | Me | Hex |
| (CH₂)₇CH₃ | Me | Me | Hex |
| (CH₂)₉CH₃ | Me | Me | Hex |
| (CH₂)₇CH₃ | Me | Me | (CH₂)₇CH₃ |
| (CH₂)₉CH₃ | Me | Me | (CH₂)₇CH₃ |
| (CH₂)₉CH₃ | Me | Me | (CH₂)₉CH₃ |
| Bu | Bu | Me | Bu |
| Pen | Bu | Me | Bu |
| Hex | Bu | Me | Bu |
| Bu | Hex | Me | Bu |
| Pen | Hex | Me | Bu |
| Hex | Hex | Me | Bu |
| Bu | Bu | Bu | Bu |
| Pen | Bu | Bu | Bu |
| Hex | Bu | Bu | Bu |
| Bu | Hex | Hex | Bu |
| Pen | Hex | Hex | Bu |
| Hex | Hex | Hex | Bu |
| Bu | (CH₂)₇CH₃ | (CH₂)₇CH₃ | Bu |
| Pen | (CH₂)₇CH₃ | (CH₂)₇CH₃ | Bu |
| Hex | (CH₂)₇CH₃ | (CH₂)₇CH₃ | Bu |
| Bu | (CH₂)₉CH₃ | (CH₂)₉CH₃ | Bu |
| Pen | (CH₂)₉CH₃ | (CH₂)₉CH₃ | Bu |
| Hex | (CH₂)₉CH₃ | (CH₂)₉CH₃ | Bu |
| Pr | Cl | Cl | Pr |
| Bu | Cl | Cl | Bu |
| Pen | Cl | Cl | Pen |
| Hex | Cl | Cl | Hex |
| Pr | Br | Br | Pr |
| Bu | Br | Br | Bu |
| Pen | Br | Br | Pen |
| Hex | Br | Br | Hex |
| Pr | Cl | Pr | Cl |
| Bu | Cl | Bu | Cl |
| Pen | Cl | Pen | Cl |
| Hex | Cl | Hex | Cl |
| Pr | Br | Pr | Br |
| Bu | Br | Bu | Br |
| Pen | Br | Pen | Br |
| Hex | Br | Hex | Br |
| =CH₂ | H | H | H |
| =CHCH₃ | H | H | H |
| =CHCH₂CH₃ | H | H | H |
| =CH(CH₂)₂CH₃ | H | H | H |
| =CH(CH₂)₃CH₃ | H | H | H |
| =CH(CH₂)₄CH₃ | H | H | H |
| =CH(CH₂)₅CH₃ | H | H | H |
| =CH(CH₂)₆CH₃ | H | H | H |
| =CH(CH₂)₇CH₃ | H | H | H |
| =CH(CH₂)₈CH₃ | H | H | H |
| CH=CH₂ | H | H | H |
| CH=CHCH₃ | H | H | H |
| CH=CHCH₂CH₃ | H | H | H |
| CH=CH(CH₂)₂CH₃ | H | H | H |
| CH=CH(CH₂)₃CH₃ | H | H | H |

TABLE 1-continued

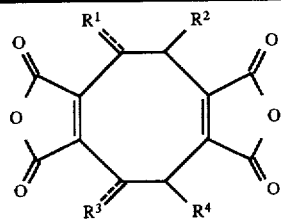

| R¹ | R² | R³ | R⁴ |
|---|---|---|---|
| CH=CH(CH₂)₄CH₃ | H | H | H |
| CH=CH(CH₂)₅CH₃ | H | H | H |
| CH=CH(CH₂)₆CH₃ | H | H | H |
| CH=CH(CH₂)₇CH₃ | H | H | H |
| CH=CClCH₂CH₃ | H | H | H |
| CH=CClCH₂CH₂CH₃ | H | H | H |
| CH=CMeCH₂CH₃ | H | H | H |
| CH=CMeCH₂CH₂CH₃ | H | H | H |
| CH=CMe(CH₂)₃CH₃ | H | H | H |
| CH₂CH=CH₂ | H | H | H |
| CH₂CH=CHCH₃ | H | H | H |
| CH₂CH=CHCH₂CH₃ | H | H | H |
| CH₂CH=CHCH=CH₂ | H | H | H |
| CH₂CH=CH(CH₂)₂CH₃ | H | H | H |
| CH₂CH=CH(CH₂)₃CH₃ | H | H | H |
| CH₂CH=CH(CH₂)₄CH₃ | H | H | H |
| CH₂CH=CH(CH₂)₅CH₃ | H | H | H |
| CH₂CH=CH(CH₂)₆CH₃ | H | H | H |
| =CHCH₂CH₃ | H | H | Bu |
| =CH(CH₂)₂CH₃ | H | H | Bu |
| =CH(CH₂)₃CH₃ | H | H | Bu |
| =CH(CH₂)₄CH₃ | H | H | Bu |
| =CH(CH₂)₅CH₃ | H | H | Bu |
| =CH(CH₂)₆CH₃ | H | H | Bu |
| =CH(CH₂)₇CH₃ | H | H | Bu |
| =CH(CH₂)₈CH₃ | H | H | Bu |
| CH=CH₂ | H | H | Bu |
| CH=CHCH₃ | H | H | Bu |
| CH=CHCH₂CH₃ | H | H | Bu |
| CH=CH(CH₂)₂CH₃ | H | H | Bu |
| CH=CH(CH₂)₃CH₃ | H | H | Bu |
| CH=CH(CH₂)₄CH₃ | H | H | Bu |
| CH=CH(CH₂)₅CH₃ | H | H | Bu |
| CH=CH(CH₂)₆CH₃ | H | H | Bu |
| CH=CH(CH₂)₇CH₃ | H | H | Bu |
| CH₂CH=CH₂ | H | H | Bu |
| CH₂CH=CHCH₃ | H | H | Bu |
| CH₂CH=CHCH₂CH₃ | H | H | Bu |
| CH₂CH=CHCH=CH₂ | H | H | Bu |
| CH₂CH=CH(CH₂)₂CH₃ | H | H | Bu |
| CH=CClCH₂CH₃ | H | H | Bu |
| CH=CClCH₂CH₂CH₃ | H | H | Bu |
| CH=CMeCH₂CH₃ | H | H | Bu |
| CH=CMe(CH₂CH₂CH₃) | H | H | Bu |
| CH=CMe(CH₂)₃CH₃ | H | H | Bu |
| =CHCH₃ | Bu | H | H |
| =CHCH₂CH₃ | Bu | H | H |
| =CH(CH₂)₂CH₃ | Bu | H | H |
| =CH(CH₂)₃CH₃ | Bu | H | H |
| =CH(CH₂)₄CH₃ | Bu | H | H |
| CH=CH₂ | Bu | H | H |
| CH=CHCH₃ | Bu | H | H |
| CH=CHCH₂CH₃ | Bu | H | H |
| CH=CH(CH₂)₂CH₃ | Bu | H | H |
| CH=CH(CH₂)₃CH₃ | Bu | H | H |
| CH₂CH=CH₂ | Bu | H | H |
| CH₂CH=CHCH₃ | Bu | H | H |
| CH₂CH=CHCH₂CH₃ | Bu | H | H |
| CH₂CH=CHCH=CH₂ | Bu | H | H |
| CH₂CH=CH(CH₂)₂CH₃ | Bu | H | H |
| =CHCH₃ | H | Buⁱ | H |
| =CHCH₂CH₃ | H | Bu | H |
| =CH(CH₂)₂CH₃ | H | Bu | H |
| =CH(CH₂)₃CH₃ | H | Bu | H |
| =CH(CH₂)₄CH₃ | H | Bu | H |
| CH=CH₂ | H | Bu | H |

TABLE 1-continued

| R¹ | R² | R³ | R⁴ |
|---|---|---|---|
| CH=CHCH₃ | H | Bu | H |
| CH=CHCH₂CH₃ | H | Bu | H |
| CH=CH(CH₂)₂CH₃ | H | Bu | H |
| CH=CH(CH₂)₃CH₃ | H | Bu | H |
| CH₂CH=CH₂ | H | Bu | H |
| CH₂CH=CHCH₃ | H | Bu | H |
| CH₂CH=CHCH₂CH₃ | H | Bu | H |
| CH₂CH=CHCH=CH₂ | H | Bu | H |
| CH₂CH=CH(CH₂)₂CH₃ | H | Bu | H |
| CH=CH₂ | H | H | CH=CH₂ |
| CH=CH₂ | H | CH=CH₂ | H |
| CH=CHCH₃ | H | H | CH=CHCH₃ |
| CH=CHCH₃ | H | CH=CHCH₃ | H |
| CH=CHCH₂CH₃ | H | H | CH=CHCH₂CH₃ |
| CH=CHCH₂CH₃ | H | CH=CHCH₂CH₃ | H |
| CH=CH(CH₂)₂CH₃ | H | H | CH=CH(CH₂)₂CH₃ |
| CH=CH(CH₂)₂CH₃ | H | CH=CH(CH₂)₂CH₃ | H |
| CH₂CH=CH₂ | H | H | CH₂CH=CH₂ |
| CH₂CH=CH₂ | H | CH₂CH=CH₂ | H |
| CH₂CH=CHCH₃ | H | H | CH₂CH=CHCH₃ |
| CH₂CH=CHCH₃ | H | CH₂CH=CHCH₃ | H |
| CH₂CH=CHCH₂CH₃ | H | H | CH₂CH=CHCH₂CH₃ |
| CH₂CH=CHCH₂CH₃ | H | CH₂CH=CHCH₂CH₃ | H |
| CH₂CH=CH(CH₂)₂CH₃ | H | H | CH₂CH=CH(CH₂)₂CH₃ |
| CH₂CH=CH(CH₂)₂CH₃ | H | CH₂CH=CH(CH₂)₂CH₃ | H |
| CH₂CH=CHCH=CH₂ | H | H | CH₂CH=CHCH=CH₂ |
| CH₂CH=CHCH=CH₂ | H | CH₂CH=CHCH=CH₂ | H |
| CH=CH₂ | CH=CH₂ | CH=CH₂ | CH=CH₂ |
| CH=CHCH₃ | CH=CHCH₃ | CH=CHCH₃ | CH=CHCH₃ |
| CH=CHCH₂CH₃ | CH=CHCH₂CH₃ | CH=CHCH₂CH₃ | CH=CHCH₂CH₃ |
| CH₂CH=CH₂ | CH₂CH=CH₂ | CH₂CH=CH₂ | CH₂CH=CH₂ |
| CH₂CH=CHCH₃ | CH₂CH=CHCH₃ | CH₂CH=CHCH₃ | CH₂CH=CHCH₃ |
| CH₂CH=CHCH₂CH₃ | CH₂CH=CHCH₂CH₃ | CH₂CH=CHCH₂CH₃ | CH₂CH=CHCH₂CH₃ |
| CH₂CH=CHCH=CH₂ | CH₂CH=CHCH=CH₂ | CH₂CH=CHCH=CH₂ | CH₂CH=CHCH=CH₂ |
| C≡CH | H | H | H |
| C≡CCH₃ | H | H | H |
| C≡CCH₂CH₃ | H | H | H |
| C≡CCH₂CH₂CH₃ | H | H | H |
| C≡C(CH₂)₃CH₃ | H | H | H |
| C≡C(CH₂)₄CH₃ | H | H | H |
| C≡C(CH₂)₅CH₃ | H | H | H |
| C≡C(CH₂)₆CH₃ | H | H | H |
| C≡C(CH₂)₇CH₃ | H | H | H |
| CH₂C≡CH | H | H | H |
| CH₂C≡CCH₃ | H | H | H |
| CH₂C≡CCH₂CH₃ | H | H | H |
| CH₂C≡C(CH₂)₂CH₃ | H | H | H |
| C≡CH | H | H | Bu |
| C≡CCH₃ | H | H | Bu |
| C≡CCH₂CH₃ | H | H | Bu |
| C≡CCH₂CH₂CH₃ | H | H | Bu |

TABLE 1-continued

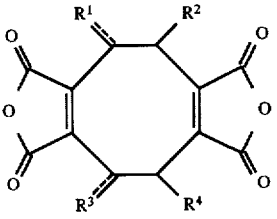

| R¹ | R² | R³ | R⁴ |
|---|---|---|---|
| C≡C(CH₂)₃CH₃ | H | H | Bu |
| C≡C(CH₂)₄CH₃ | H | H | Bu |
| C≡C(CH₂)₅CH₃ | H | H | Bu |
| C≡C(CH₂)₆CH₃ | H | H | Bu |
| C≡C(CH₂)₇CH₃ | H | H | Bu |
| CH₂C≡CH | H | H | Bu |
| CH₂C≡CCH₃ | H | H | Bu |
| CH₂C≡CCH₂CH₃ | H | H | Bu |
| CH₂C≡C(CH₂)₂CH₃ | H | H | Bu |
| C≡CH | Bu | H | H |
| C≡CCH₃ | Bu | H | H |
| C≡CCH₂CH₃ | Bu | H | H |
| C≡CCH₂CH₂CH₃ | Bu | H | H |
| C≡C(CH₂)₃CH₃ | Bu | H | H |
| C≡C(CH₂)₄CH₃ | Bu | H | H |
| C≡C(CH₂)₅CH₃ | Bu | H | H |
| C≡C(CH₂)₆CH₃ | Bu | H | H |
| C≡C(CH₂)₇CH₃ | Bu | H | H |
| CH₂C≡CH | Bu | H | H |
| CH₂C≡CCH₃ | Bu | H | H |
| CH₂C≡CCH₂CH₃ | Bu | H | H |
| CH₂C≡C(CH₂)₂CH₃ | Bu | H | H |
| C≡CH | H | Bu | H |
| C≡CCH₃ | H | Bu | H |
| C≡CCH₂CH₃ | H | Bu | H |
| C≡CCH₂CH₂CH₃ | H | Bu | H |
| C≡C(CH₂)₃CH₃ | H | Bu | H |
| C≡C(CH₂)₄CH₃ | H | Bu | H |
| C≡C(CH₂)₅CH₃ | H | Bu | H |
| C≡C(CH₂)₆CH₃ | H | Bu | H |
| C≡C(CH₂)₇CH₃ | H | Bu | H |
| CH₂C≡CH | H | Bu | H |
| CH₂C≡CCH₃ | H | Bu | H |
| CH₂C≡CCH₂CH₃ | H | Bu | H |
| CH₂C≡C(CH₂)₂CH₃ | H | Bu | H |

TABLE 1-continued

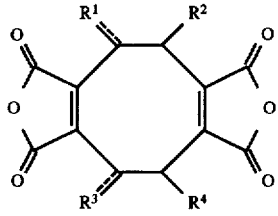

| R¹ | R² | R³ | R⁴ |
|---|---|---|---|
| C≡CH | H | H | C≡CH |
| C≡CH | H | C≡CH | H |
| CH₂C≡CH | H | H | CH₂C≡CH |
| CH₂C≡CH | H | CH₂C≡CH | CH₂C≡CH |
| C≡CH | C≡CH | C≡CH | C≡CH |
| CH₂C≡CH | CH₂C≡CH | CH₂C≡CH | CH₂C≡CH |
| CH=CHCH₃ | Cl | Cl | CH=CHCH₃ |
| CH=CHCH₃ | Cl | CH=CHCH₃ | Cl |
| CH=CHCH₂CH₃ | Cl | Cl | CH=CHCH₂CH₃ |
| CH=CHCH₂CH₃ | Cl | CH=CHCH₂CH₃ | Cl |
| CH=CH(CH₂)₂CH₃ | Cl | Cl | CH=CH(CH₂)₂CH₃ |
| CH=CH(CH₂)₂CH₃ | Cl | CH=CH(CH₂)₂CH₃ | Cl |
| CH₂CH=CH₂ | Cl | Cl | CH₂CH=CH₂ |
| CH₂CH=CH₂ | Cl | CH₂CH=CH₂ | Cl |
| CH₂CH=CHCH₃ | Cl | Cl | CH₂CH=CHCH₃ |
| CH₂CH=CHCH₃ | Cl | CH₂CH=CHCH₃ | Cl |
| CH₂CH=CHCH₂CH₃ | Cl | Cl | CH₂CH=CHCH₂CH₃ |
| CH₂CH=CHCH₂CH₃ | Cl | CH₂CH=CHCH₂CH₃ | Cl |
| CH₂CH=CH(CH₂)₂CH₃ | Cl | Cl | CH₂CH=CH(CH₂)₂CH₃ |
| CH₂CH=CH(CH₂)₂CH₃ | Cl | CH₂CH=CHCH₂CH₃ | Cl |
| CH₂CH=CHCH=CH₂ | Cl | Cl | CH₂CH=CHCH=CH₂ |
| CH₂CH=CHCH=CH₂ | Cl | CH₂CH=CHCH=CH₂ | Cl |
| C≡CH | Cl | Cl | C≡CH |
| C≡CH | Cl | C≡CH | Cl |
| CH₂C≡CH | Cl | Cl | CH₂C≡CH |
| CH₂C≡CH | Cl | CH₂C≡CH | Cl |
| CH=CHCH₃ | Br | Br | CH=CHCH₃ |
| CH=CHCH₂CH₃ | Br | Br | CH=CHCH₂CH₃ |
| CH=CH(CH₂)₂CH₃ | Br | Br | CH=CH(CH₂)₂CH₃ |
| CH₂CH=CH₂ | Br | Br | CH₂CH=CH₂ |
| CH₂CH=CHCH₂CH₃ | Br | Br | CH₂CH=CHCH₂CH₃ |
| CH₂Br | H | H | H |
| CHBr(CH₂)₃CH₃ | H | H | H |
| CH₂Br | H | H | Bu |
| CHBr(CH₂)₃CH₃ | H | H | Bu |
| CH₂Cl | H | H | H |
| CHCl(CH₂)₃CH₃ | H | H | H |
| CH₂Cl | H | H | Bu |
| CHCl(CH₂)₃CH₃ | H | H | Bu |
| CH₂F | H | H | H |
| CHF(CH₂)₃CH₃ | H | H | H |
| CH₂F | H | H | Bu |
| CHF(CH₂)₃CH₃ | H | H | Bu |
| CHO | H | H | H |
| COCH₃ | H | H | H |
| CO(CH₂)₃CH₃ | H | H | H |
| CHO | H | H | Bu |
| COCH₃ | H | H | Bu |
| CO(CH₂)₃CH₃ | H | H | Bu |
| C(=NPh)CH₃ | H | H | H |
| C(=NPh)(CH₂)₃CH₃ | H | H | H |
| C(=NPh)CH₃ | H | H | Bu |
| C(=NPh)(CH₂)₃CH₃ | H | H | Bu |
| C(=NOH)CH₃ | H | H | H |
| C(=NOH)(CH₂)₃CH₃ | H | H | H |
| C(=NOH)CH₃ | H | H | Bu |
| C(=NOH)(CH₂)₃CH₃ | H | H | Bu |

TABLE 1-continued

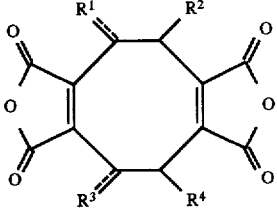

| R¹ | R² | R³ | R⁴ |
|---|---|---|---|
| C(=NOMe)CH₃ | H | H | H |
| C(=NOMe)(CH₂)₃CH₃ | H | H | H |
| C(=NOMe)CH₃ | H | H | Bu |
| C(=NOMe)(CH₂)₃CH₃ | H | H | Bu |
| C(=NOMe)(CH₂)₈CH₃ | H | H | Bu |
| CH(OH)CH₃ | H | H | H |
| CH(OH)(CH₂)₃CH₃ | H | H | H |
| CH(OH)CH₃ | H | H | Bu |
| CH(OH)CH₂CH₃ | H | H | Bu |
| CH(OH)(CH₂)₂CH₃ | H | H | Bu |
| CH(OH)(CH₂)₃CH₃ | H | H | Bu |
| CH(OH)(CH₂)₄CH₃ | H | H | Bu |
| CH(OH)(CH₂)₅CH₃ | H | H | Bu |
| CH(OH)(CH₂)₆CH₃ | H | H | Bu |
| CH(OH)(CH₂)₇CH₃ | H | H | Bu |
| CH(OH)(CH₂)₈CH₃ | H | H | Bu |
| C(OCH₃)₂CH₃ | H | H | H |
| C(OCH₃)₂(CH₂)₃CH₃ | H | H | H |
| C(OCH₃)₂CH₃ | H | H | Bu |
| C(OCH₃)₂(CH₂)₃CH₃ | H | H | Bu |
| C(OCH₂CH₂O)CH₃ | H | H | H |
| C(OCH₂CH₂O)(CH₂)₃CH₃ | H | H | H |
| C(OCH₂CH₂O)CH₃ | H | H | Bu |
| C(OCH₂CH₂O)(CH₂)₃CH₃ | H | H | Bu |
| CH(OMe)CH₃ | H | H | H |
| CH(OMe)(CH₂)₃CH₃ | H | H | H |
| CH(OMe)CH₃ | H | H | Bu |
| CH(OMe)(CH₂)₃CH₃ | H | H | Bu |
| CH(OCH₂CH=CH₂)CH₃ | H | H | H |
| CH(OCH₂CH=CH₂)(CH₂)₃CH₃ | H | H | H |
| CH(OCH₂CH=CH₂)CH₃ | H | H | Bu |
| CH(OCH₂CH=CH₂)(CH₂)₃CH₃ | H | H | Bu |
| CH(OCH₂C≡CH)CH₃ | H | H | H |
| CH(OCH₂C≡CH)(CH₂)₃CH₃ | H | H | H |
| CH(OCH₂C≡CH)CH₃ | H | H | Bu |
| CH(OCH₂C≡CH)(CH₂)₃CH₃ | H | H | Bu |
| CH(OSiMe₃)CH₃ | H | H | H |
| CH(OSiMe₃)(CH₂)₃CH₃ | H | H | H |
| CH(OSiMe₃)CH₃ | H | H | Bu |
| CH(OSiMe₃)(CH₂)₃CH₃ | H | H | Bu |
| CH(OSiMe₃)(CH₂)₆CH₃ | H | H | Bu |
| CH(OSO₂CH₃)CH₃ | H | H | H |
| CH(OSO₂CH₃)(CH₂)₃CH₃ | H | H | H |
| CH(OSO₂CH₃)CH₃ | H | H | Bu |
| CH(OSO₂CH₃)(CH₂)₃CH₃ | H | H | Bu |
| CH(OCH₂Ph)CH₃ | H | H | H |
| CH(OCH₂Ph)(CH₂)₃CH₃ | H | H | H |
| CH(OCH₂Ph)CH₃ | H | H | Bu |
| CH(OCH₂Ph)(CH₂)₃CH₃ | H | H | Bu |
| CH(OPO(OMe)₂)CH₃ | H | H | H |
| CH(OPO(OMe)₂)(CH₂)₃CH₃ | H | H | H |
| CH(OPO(OMe)₂)CH₃ | H | H | Bu |
| CH(OPO(OMe)₂)(CH₂)₃CH₃ | H | H | Bu |
| CH(OPO(OEt)₂)CH₃ | H | H | Bu |
| CH(OPO(OEt)₂)(CH₂)₃CH₃ | H | H | Bu |
| CH(OPO(OPh)₂)CH₃ | H | H | Bu |
| CH(OPO(OPh)₂)(CH₂)₃CH₃ | H | H | Bu |
| CH(OCH₂OCH₃)CH₃ | H | H | H |
| CH(OCH₂OCH₃)(CH₂)₃CH₃ | H | H | H |
| CH(OCH₂OCH₃)CH₃ | H | H | Bu |
| CH(OCH₂OCH₃)(CH₂)₃CH₃ | H | H | Bu |
| CH(OTHP)CH₃ | H | H | H |

TABLE 1-continued

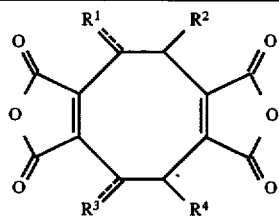

| R[1] | R[2] | R[3] | R[4] |
| --- | --- | --- | --- |
| CH(OTHP)(CH$_2$)$_3$CH$_3$ | H | H | H |
| CH(OTHP)CH$_3$ | H | H | Bu |
| CH(OTHP)(CH$_2$)$_3$CH$_3$ | H | H | Bu |
| CH(OCOCH$_3$)CH$_3$ | H | H | H |
| CH(OCOCH$_3$)(CH$_2$)$_3$CH$_3$ | H | H | H |
| CH(OCOCH$_3$)CH$_3$ | H | H | Bu |
| CH(OCOCH$_3$)(CH$_2$)$_3$CH$_3$ | H | H | Bu |
| CH(OCOPh)CH$_3$ | H | H | Bu |
| CH(OCOPh)(CH$_2$)$_3$CH$_3$ | H | H | Bu |
| CH(OCOPh-4-Cl)CH$_3$ | H | H | Bu |
| CH(OCOPh-2-Cl)(CH$_2$)$_3$CH$_3$ | H | H | Bu |
| CH(OCOPh-3-Cl)(CH$_2$)$_3$CH$_3$ | H | H | Bu |
| CH(OCOPh-4-Cl)(CH$_2$)$_3$CH$_3$ | H | H | Bu |
| CH(OCOPh-2-Br)(CH$_2$)$_3$CH$_3$ | H | H | Bu |
| CH(OCOPh-3-Br)(CH$_2$)$_3$CH$_3$ | H | H | Bu |
| CH(OCOPh-4-Br)(CH$_2$)$_3$CH$_3$ | H | H | Bu |
| CH(OCOPh-4-Me)(CH$_2$)$_3$CH$_3$ | H | H | Bu |
| CH(OCOPh-4-OMe)(CH$_2$)$_3$CH$_3$ | H | H | Bu |
| CH(OCOPh-4-CF$_3$)(CH$_2$)$_3$CH$_3$ | H | H | Bu |
| CH(OCOPh-4-CN)(CH$_2$)$_3$CH$_3$ | H | H | Bu |
| CH(OCOPh-4-NO$_2$)(CH$_2$)$_3$CH$_3$ | H | H | Bu |
| CH(OCOPh-2,4-Cl$_2$)(CH$_2$)$_3$CH$_3$ | H | H | Bu |
| CH(OCOPh-3,4-Cl$_2$)(CH$_2$)$_3$CH$_3$ | H | H | Bu |
| CH(OCOPh-2,4-Br$_2$)(CH$_2$)$_3$CH$_3$ | H | H | Bu |
| CH(OCOOMe)CH$_3$ | H | H | H |
| CH(OCOOMe)(CH$_2$)$_3$CH$_3$ | H | H | H |
| CH(OCOOMe)CH$_3$ | H | H | Bu |
| CH(OCOOMe)(CH$_2$)$_3$CH$_3$ | H | H | Bu |
| CH(OCONH$_2$)CH$_3$ | H | H | Bu |
| CH(OCONH$_2$)(CH$_2$)$_3$CH$_3$ | H | H | Bu |
| CH(OCONMe$_2$)CH$_3$ | H | H | H |
| CH(OCONMe$_2$)(CH$_2$)$_3$CH$_3$ | H | H | H |
| CH(OCONMe$_2$)CH$_3$ | H | H | Bu |
| CH(OCONMe$_2$)(CH$_2$)$_3$CH$_3$ | H | H | Bu |
| CH(OCONHPh)CH$_3$ | H | H | H |
| CH(OCONHPh)(CH$_2$)$_3$CH$_3$ | H | H | H |
| CH(OCONHPh)CH$_3$ | H | H | Bu |
| CH(OCONHPh)(CH$_2$)$_3$CH$_3$ | H | H | Bu |
| CH(OCONHPh-4-Cl)CH$_3$ | H | H | Bu |
| CH(OCONHPh-4-Cl)(CH$_2$)$_3$CH$_3$ | H | H | Bu |
| CH(OCONHPh-4-Br)(CH$_2$)$_3$CH$_3$ | H | H | Bu |
| CH(OCONHPh-4-Me)(CH$_2$)$_3$CH$_3$ | H | H | Bu |
| CH(OCONHPh-4-OMe)(CH$_2$)$_3$CH$_3$ | H | H | Bu |
| CH(OCONHPh-4-NO$_2$)(CH$_2$)$_3$CH$_3$ | H | H | Bu |
| CH(SH)CH$_3$ | H | H | H |
| CH(SH)(CH$_2$)$_3$CH$_3$ | H | H | H |
| CH(SH)CH$_3$ | H | H | Bu |
| CH(SH)(CH$_2$)$_3$CH$_3$ | H | H | Bu |
| CH(SMe)CH$_3$ | H | H | Bu |
| CH(SMe)(CH$_2$)$_3$CH$_3$ | H | H | Bu |
| CH(SCH$_2$Ph)CH$_3$ | H | H | Bu |
| CH(SCH$_2$Ph)(CH$_2$)$_3$CH$_3$ | H | H | Bu |
| CH(NH$_2$)CH$_3$ | H | H | H |
| CH(NH$_2$)(CH$_2$)$_3$CH$_3$ | H | H | H |
| CH(NH$_2$)CH$_3$ | H | H | Bu |
| CH(NH$_2$)(CH$_2$)$_3$CH$_3$ | H | H | Bu |
| CH(NHMe)CH$_3$ | H | H | H |
| CH(NHMe)(CH$_2$)$_3$CH$_3$ | H | H | H |
| CH(NHMe)CH$_3$ | H | H | Bu |
| CH(NHMe)(CH$_2$)$_3$CH$_3$ | H | H | Bu |
| CH(NMe$_2$)CH$_3$ | H | H | Bu |
| CH(NMe$_2$)(CH$_2$)$_3$CH$_3$ | H | H | Bu |
| CH(NHCOCH$_3$)CH$_3$ | H | H | Bu |
| CH(NHCOCH$_3$)(CH$_2$)$_3$CH$_3$ | H | H | Bu |
| CH(NHCOPh)CH$_3$ | H | H | Bu |
| CH(NHCOPh)(CH$_2$)$_3$CH$_3$ | H | H | Bu |

TABLE 1-continued

| R¹ | R² | R³ | R⁴ |
|---|---|---|---|
| CH(NHCOPh-4-Cl)CH₃ | H | H | Bu |
| CH(NHCOPh-4-Cl)(CH₂)₃CH₃ | H | H | Bu |
| CH(NHCOPh-4-Br)CH₃ | H | H | Bu |
| CH(NHCOPh-4-Br)(CH₂)₃CH₃ | H | H | Bu |
| CH(NHCOPh-4-Me)CH₃ | H | H | Bu |
| CH(NHCOPh-4-Me)(CH₂)₃CH₃ | H | H | Bu |
| CH(NHCOPh-4-OMe)CH₃ | H | H | Bu |
| CH(NHCOPh-4-OMe)(CH₂)₃CH₃ | H | H | Bu |
| CH(NHCOPh-4-CN)CH₃ | H | H | Bu |
| CH(NHCOPh-4-CN)(CH₂)₃CH₃ | H | H | Bu |
| CH(NHCOPh-4-NO₂)CH₃ | H | H | Bu |
| CH(NHCOPh-4-NO₂)(CH₂)₃CH₃ | H | H | Bu |
| CH(N(COPh)₂)CH₃ | H | H | Bu |
| CH(N(COPh)₂)(CH₂)₃CH₃ | H | H | Bu |
| CH(NHCOOMe)CH₃ | H | H | Bu |
| CH(NHCOOMe)(CH₂)₃CH₃ | H | H | Bu |
| CH(NHCOOEt)CH₃ | H | H | Bu |
| CH(NHCOOEt)(CH₂)₃CH₃ | H | H | Bu |
| CH(NHCOOPr)CH₃ | H | H | Bu |
| CH(NHCOOPr)(CH₂)₃CH₃ | H | H | Bu |
| COCH₂Cl | H | H | Bu |
| COCHCl(CH₂)₂CH₃ | H | H | Bu |
| COCH₂Br | H | H | Bu |
| COCHBr(CH₂)₂CH₃ | H | H | Bu |
| COCH₂F | H | H | Bu |
| COCHF(CH₂)₂CH₃ | H | H | Bu |
| COCH₂CH₃ | H | H | Bu |
| COCHMe(CH₂)₂CH₃ | H | H | Bu |
| COCH₂CH₂CH₃ | H | H | Bu |
| COCHEt(CH₂)₂CH₃ | H | H | Bu |
| COCMe₂(CH₂)₂CH₃ | H | H | Bu |
| CMe(OH)CH₃ | H | H | Bu |
| CMe(OH)(CH₂)₃CH₃ | H | H | Bu |
| CEt(OH)CH₃ | H | H | Bu |
| CEt(OH)(CH₂)₃CH₃ | H | H | Bu |
| CH(OH)-i-Pr | H | H | Bu |
| CH(OH)-i-Bu | H | H | Bu |
| CH(OH)-s-Bu | H | H | Bu |
| CHCl-i-Pr | H | H | Bu |
| CHCl-i-Bu | H | H | Bu |
| CHCl-s-Bu | H | H | Bu |
| CHBr-i-Pr | H | H | Bu |
| CHBr-i-Bu | H | H | Bu |
| CHBr-s-Bu | H | H | Bu |
| CHF-i-Pr | H | H | Bu |
| CHF-i-Bu | H | H | Bu |
| CHF-s-Bu | H | H | Bu |
| CF₂CH₃ | H | H | Bu |
| CF₂(CH₂)₃CH₃ | H | H | Bu |
| CHFCH₃ | H | H | CHFCH₃ |
| CH₂CF₃ | H | H | CH₂CF₃ |
| CH₂CF₂CF₃ | H | H | CH₂CF₂CF₃ |
| CH₂CF₂CF₂CF₃ | H | H | CH₂CF₂CF₂CF₃ |
| CH(OH)(CH₂)₃CH₃ | H | H | CH(OH)(CH₂)₃CH₃ |
| CH(OH)(CH₂)₃CH₃ | CH(OH)(CH₂)₃CH₃ | H | H |
| CH(OH)(CH₂)₃CH₃ | H | CH(OH)(CH₂)₃CH₃ | H |
| CH(OH)(CH₂)₃CH₃ | Br | H | Bu |
| CH(OH)(CH₂)₃CH₃ | Cl | H | Bu |
| CH(OH)(CH₂)₃CH₃ | Br | Br | Bu |
| CH(OH)(CH₂)₃CH₃ | Cl | Cl | Bu |
| CH(OH)(CH₂)₃CH₃ | Me | H | Bu |
| CH(OH)(CH₂)₃CH₃ | Et | H | Bu |
| CH(OH)(CH₂)₃CH₃ | Pr | H | Bu |
| CH(OH)(CH₂)₃CH₃ | Bu | H | Bu |
| CH(OH)(CH₂)₃CH₃ | Pen | H | Bu |
| CH(OH)(CH₂)₃CH₃ | Hex | H | Bu |

TABLE 1-continued

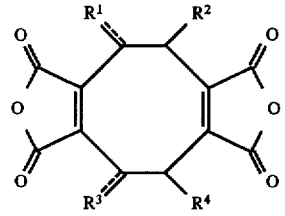

| R¹ | R² | R³ | R⁴ |
|---|---|---|---|
| CHCl(CH₂)₃CH₃ | Cl | H | Bu |
| CHCl(CH₂)₃CH₃ | Br | H | Bu |
| CHCl(CH₂)₃CH₃ | Me | H | Bu |
| CHCl(CH₂)₃CH₃ | Cl | Cl | Bu |
| CHCF(CH₂)₃CH₃ | Cl | H | Bu |
| CHCF(CH₂)₃CH₃ | Br | H | Bu |
| CHCF(CH₂)₃CH₃ | Me | H | Bu |
| CHCF(CH₂)₃CH₃ | Cl | Cl | Bu |
| CHMe(CH₂)₃CH₃ | Cl | H | Bu |
| CHMe(CH₂)₃CH₃ | Br | H | Bu |
| CHMe(CH₂)₃CH₃ | Me | H | Bu |
| Cl | H | H | H |
| Cl | Cl | H | H |
| Cl | H | Cl | H |
| Cl | Cl | Cl | H |
| Cl | Cl | Cl | Cl |
| Br | H | H | H |
| Br | Br | H | H |
| Br | H | Br | H |
| Br | Br | Br | H |
| Br | Br | Br | Br |
| I | H | H | H |
| I | I | H | H |
| I | H | I | H |
| I | I | I | H |
| I | I | I | I |
| Br | H | H | Me |
| Br | H | H | Et |
| Br | H | H | Pr |
| Br | H | H | Bu |
| Br | H | H | Pen |
| Br | H | H | Hex |
| Br | H | Me | H |
| Br | H | Et | H |
| Br | H | Pr | H |
| Br | H | Bu | H |
| Br | H | Pen | H |
| Br | H | Hex | H |
| CH(OH)(CH₂)₃CH₃ | H | OH | H |
| CH(OH)(CH₂)₃CH₃ | H | Cl | H |
| CH(OH)(CH₂)₃CH₃ | H | Br | H |
| CH(OH)(CH₂)₃CH₃ | H | OH | Me |
| CH(OH)(CH₂)₃CH₃ | H | OH | Et |
| CH(OH)(CH₂)₃CH₃ | H | OH | Pr |
| CH(OH)(CH₂)₃CH₃ | H | OH | Bu |
| CH(OH)(CH₂)₃CH₃ | H | OH | Pen |
| CH(OH)(CH₂)₃CH₃ | H | OH | Hex |
| CH(OH)(CH₂)₃CH₃ | H | =O | H |
| CH(OH)(CH₂)₃CH₃ | H | =O | Me |
| CH(OH)(CH₂)₃CH₃ | H | =O | Et |
| CH(OH)(CH₂)₃CH₃ | H | =O | Pr |
| CH(OH)(CH₂)₃CH₃ | H | =O | Bu |
| CH(OH)(CH₂)₃CH₃ | H | =O | Pen |
| CH(OH)(CH₂)₃CH₃ | H | =O | Hex |
| CH(OH)(CH₂)₃CH₃ | H | =O | H |
| Pen | H | =O | Me |
| Pen | H | =O | Et |
| Pen | H | =O | Pr |
| Pen | H | =O | Bu |
| Pen | H | =O | Pen |
| Pen | H | =O | Hex |
| CHF(CH₂)₃CH₃ | H | =O | H |
| CHF(CH₂)₃CH₃ | H | =O | Me |
| CHF(CH₂)₃CH₃ | H | =O | Et |
| CHF(CH₂)₃CH₃ | H | =O | Pr |
| CHF(CH₂)₃CH₃ | H | =O | Bu |

TABLE 1-continued

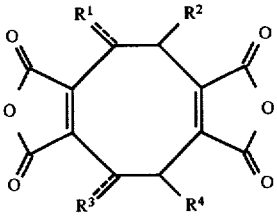

| R¹ | R² | R³ | R⁴ |
|---|---|---|---|
| CHF(CH₂)₃CH₃ | H | =O | Pen |
| CHF(CH₂)₃CH₃ | H | =O | Hex |

TABLE 2

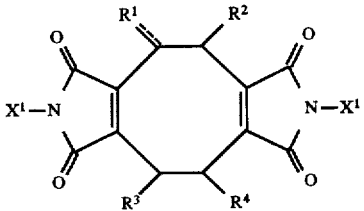

| R¹ | R² | R³ | R⁴ | X¹ |
|---|---|---|---|---|
| Me | H | H | H | H |
| Et | H | H | H | H |
| Pr | H | H | H | H |
| Bu | H | H | H | H |
| Pen | H | H | H | H |
| Hex | H | H | H | H |
| (CH₂)₆CH₃ | H | H | H | H |
| (CH₂)₇CH₃ | H | H | H | H |
| (CH₂)₈CH₃ | H | H | H | H |
| (CH₂)₉CH₃ | H | H | H | H |
| Me | H | H | H | Me |
| Et | H | H | H | Me |
| Pr | H | H | H | Me |
| Bu | H | H | H | Me |
| Pen | H | H | H | Me |
| Hex | H | H | H | Me |
| (CH₂)₆CH₃ | H | H | H | Me |
| (CH₂)₇CH₃ | H | H | H | Me |
| (CH₂)₈CH₃ | H | H | H | Me |
| (CH₂)₉CH₃ | H | H | H | Me |
| Me | H | H | H | Ph |
| Et | H | H | H | Ph |
| Pr | H | H | H | Ph |
| Bu | H | H | H | Ph |
| Pen | H | H | H | Ph |
| Hex | H | H | H | Ph |
| (CH₂)₆CH₃ | H | H | H | Ph |
| (CH₂)₇CH₃ | H | H | H | Ph |
| (CH₂)₈CH₃ | H | H | H | Ph |
| (CH₂)₉CH₃ | H | H | H | Ph |
| Me | H | H | H | Ph-4-Cl |
| Et | H | H | H | Ph-4-Cl |
| Pr | H | H | H | Ph-4-Cl |
| Bu | H | H | H | Ph-4-Cl |
| Pen | H | H | H | Ph-4-Cl |
| Hex | H | H | H | Ph-4-Cl |
| (CH₂)₆CH₃ | H | H | H | Ph-4-Cl |
| (CH₂)₇CH₃ | H | H | H | Ph-4-Cl |
| (CH₂)₈CH₃ | H | H | H | Ph-4-Cl |
| (CH₂)₉CH₃ | H | H | H | Ph-4-Cl |
| Me | H | H | H | Ph-4-Br |
| Et | H | H | H | Ph-4-Br |
| Pr | H | H | H | Ph-4-Br |
| Bu | H | H | H | Ph-4-Br |
| Pen | H | H | H | Ph-4-Br |
| Hex | H | H | H | Ph-4-Br |

TABLE 2-continued

| R¹ | R² | R³ | R⁴ | X¹ |
|---|---|---|---|---|
| (CH₂)₆CH₃ | H | H | H | Ph-4-Br |
| (CH₂)₇CH₃ | H | H | H | Ph-4-Br |
| (CH₂)₈CH₃ | H | H | H | Ph-4-Br |
| (CH₂)₉CH₃ | H | H | H | Ph-4-Br |
| Me | H | H | H | Ph-4-Me |
| Et | H | H | H | Ph-4-Me |
| Pr | H | H | H | Ph-4-Me |
| Bu | H | H | H | Ph-4-Cl |
| Pen | H | H | H | Ph-4-Me |
| Hex | H | H | H | Ph-4-Me |
| (CH₂)₆CH₃ | H | H | H | Ph-4-Me |
| (CH₂)₇CH₃ | H | H | H | Ph-4-Me |
| (CH₂)₈CH₃ | H | H | H | Ph-4-Me |
| (CH₂)₉CH₃ | H | H | H | Ph-4-Me |
| Me | H | H | H | CH₂Ph |
| Et | H | H | H | CH₂Ph |
| Pr | H | H | H | CH₂Ph |
| Bu | H | H | H | CH₂Ph |
| Pen | H | H | H | CH₂Ph |
| Hex | H | H | H | CH₂Ph |
| (CH₂)₆CH₃ | H | H | H | CH₂Ph |
| (CH₂)₇CH₃ | H | H | H | CH₂Ph |
| (CH₂)₈CH₃ | H | H | H | CH₂Ph |
| (CH₂)₉CH₃ | H | H | H | CH₂Ph |
| Me | H | H | Me | H |
| Et | H | H | Me | H |
| Pr | H | H | Me | H |
| Bu | H | H | Me | H |
| Pen | H | H | Me | H |
| Hex | H | H | Me | H |
| Et | H | H | Et | H |
| Pr | H | H | Et | H |
| Bu | H | H | Et | H |
| Pen | H | H | Et | H |
| Hex | H | H | Et | H |
| Pr | H | H | Pr | H |
| Bu | H | H | Pr | H |
| Pen | H | H | Pr | H |
| Hex | H | H | Pr | H |
| Bu | H | H | Bu | H |
| Pen | H | H | Bu | H |
| Hex | H | H | Bu | H |
| Pen | H | H | Pen | H |
| Hex | H | H | Pen | H |
| Hex | H | H | Hex | H |
| Pr | Pr | H | H | H |
| Bu | Bu | H | H | H |
| Pen | Pen | H | H | H |
| Hex | Hex | H | H | H |
| Pr | Pr | H | H | Me |
| Bu | Bu | H | H | Me |
| Pen | Pen | H | H | Me |
| Hex | Hex | H | H | Me |
| Pr | H | Pr | H | H |
| Bu | H | Bu | H | H |
| Pen | H | Pen | H | H |
| Hex | H | Hex | H | H |
| Pr | H | Pr | H | Me |
| Bu | H | Bu | H | Me |
| Pen | H | Pen | H | Me |
| Hex | H | Hex | H | Me |
| Pr | H | Pr | H | Ph |
| Bu | H | Bu | H | Ph |
| Pen | H | Pen | H | Ph |
| Hex | H | Hex | H | Ph |
| CH=CH₂ | H | H | H | H |

TABLE 2-continued

| R¹ | R² | R³ | R⁴ | X¹ |
|---|---|---|---|---|
| CH=CHCH₃ | H | H | H | H |
| CH=CHCH₂CH₃ | H | H | H | H |
| CH=CH(CH₂)₂CH₃ | H | H | H | H |
| CH=CH(CH₂)₃CH₃ | H | H | H | H |
| CH₂CH=CH₂ | H | H | H | H |
| CH₂CH=CHCH₃ | H | H | H | H |
| CH₂CH=CHCH₂CH₃ | H | H | H | H |
| CH₂CH=CH(CH₂)₂CH₃ | H | H | H | H |
| CH=CH₂ | H | H | H | Me |
| CH=CHCH₃ | H | H | H | Me |
| CH=CHCH₂CH₃ | H | H | H | Me |
| CH=CH(CH₂)₂CH₃ | H | H | H | Me |
| CH=CH(CH₂)₃CH₃ | H | H | H | Me |
| CH₂CH=CH₂ | H | H | H | Me |
| CH₂CH=CHCH₃ | H | H | H | Me |
| CH₂CH=CHCH₂CH₃ | H | H | H | Me |
| CH₂CH=CH(CH₂)₂CH₃ | H | H | H | Me |
| CH=CH₂ | H | H | H | Ph |
| CH=CHCH₃ | H | H | H | Ph |
| CH=CHCH₂CH₃ | H | H | H | Ph |
| CH=CH(CH₂)₂CH₃ | H | H | H | Ph |
| CH=CH(CH₂)₃CH₃ | H | H | H | Ph |
| CH₂CH=CH₂ | H | H | H | Ph |
| CH₂CH=CHCH₃ | H | H | H | Ph |
| CH₂CH=CHCH₂CH₃ | H | H | H | Ph |
| CH₂CH=CH(CH₂)₂CH₃ | H | H | H | Ph |
| CH=CH₂ | H | H | H | Ph-4-Br |
| CH=CHCH₃ | H | H | H | Ph-4-Br |
| CH=CHCH₂CH₃ | H | H | H | Ph-4-Br |
| CH=CH(CH₂)₂CH₃ | H | H | H | Ph-4-Br |
| CH=CH(CH₂)₃CH₃ | H | H | H | Ph-4-Br |
| CH₂CH=CH₂ | H | H | H | Ph-4-Br |
| CH₂CH=CHCH₃ | H | H | H | Ph-4-Br |
| CH₂CH=CHCH₂CH₃ | H | H | H | Ph-4-Br |
| CH₂CH=CH(CH₂)₂CH₃ | H | H | H | Ph-4-Br |
| CH₂CH=CH₂ | H | H | CH₂CH=CH₂ | H |
| CH₂CH=CHCH₃ | H | H | CH₂CH=CHCH₃ | H |
| CH₂CH=CHCH₂CH₃ | H | H | CH₂CH=CHCH₂CH₃ | H |
| CH₂CH=CH₂ | H | H | CH₂CH=CH₂ | Me |
| CH₂CH=CHCH₃ | H | H | CH₂CH=CHCH₃ | Me |
| CH₂CH=CHCH₂CH₃ | H | H | CH₂CH=CHCH₂CH₃ | Me |
| CH₂CH=CH₂ | H | H | CH₂CH=CH₂ | Ph |
| CH₂CH=CHCH₃ | H | H | CH₂CH=CHCH₃ | Ph |
| CH₂CH=CHCH₂CH₃ | H | H | CH₂CH=CHCH₂CH₃ | Ph |
| CH₂CH=CH₂ | CH₂CH=CH₂ | H | H | H |
| CH₂CH=CH₂ | H | CH₂CH=CH₂ | H | H |
| CH₂CH=CH₂ | CH₂CH=CH₂ | CH₂CH=CH₂ | CH₂CH=CH₂ | H |
| CH₂C≡CH | H | H | H | H |
| CH₂C≡CH | H | H | CH₂C≡CH | H |
| CH₂C≡CH | CH₂C≡CH | H | H | H |
| CH₂C≡CH | H | CH₂C≡CH | H | H |
| CH₂C≡CH | CH₂C≡CH | CH₂C≡CH | CH₂C≡CH | H |
| CH₂C≡CCH₃ | H | H | H | H |
| CH₂C≡CCH₃ | H | H | CH₂C≡CCH₃ | H |
| CH₂C≡CCH₃ | CH₂C≡CCH₃ | H | H | H |
| CH₂C≡CCH₃ | H | CH₂C≡CCH₃ | H | H |
| CH₂C≡CCH₃ | CH₂C≡CCH₃ | CH₂C≡CCH₃ | CH₂C≡CCH₃ | H |

TABLE 2-continued

| R¹ | R² | R³ | R⁴ | X¹ |
|---|---|---|---|---|
| CH(OH)CH₃ | H | H | H | H |
| CH(OH)CH₂CH₃ | H | H | H | H |
| CH(OH)(CH₂)₂CH₃ | H | H | H | H |
| CH(OH)(CH₂)₃CH₃ | H | H | H | H |
| CH(OH)(CH₂)₄CH₃ | H | H | H | H |
| CH(OH)CH₃ | H | H | Bu | H |
| CH(OH)CH₂CH₃ | H | H | Bu | H |
| CH(OH)(CH₂)₂CH₃ | H | H | Bu | H |
| CH(OH)(CH₂)₃CH₃ | H | H | Bu | H |
| CH(OH)(CH₂)₄CH₃ | H | H | Bu | H |
| CH(OH)CH₃ | H | H | Bu | Me |
| CH(OH)CH₂CH₃ | H | H | Bu | Me |
| CH(OH)(CH₂)₂CH₃ | H | H | Bu | Me |
| CH(OH)(CH₂)₃CH₃ | H | H | Bu | Me |
| CH(OH)(CH₂)₄CH₃ | H | H | Bu | Me |
| CH(OH)CH₃ | H | H | Bu | CH₂Ph |
| CH(OH)CH₂CH₃ | H | H | Bu | CH₂Ph |
| CH(OH)(CH₂)₂CH₃ | H | H | Bu | CH₂Ph |
| CH(OH)(CH₂)₃CH₃ | H | H | Bu | CH₂Ph |
| CH(OH)(CH₂)₄CH₃ | H | H | Bu | CH₂Ph |
| CHBr(CH₂)₃CH₃ | H | H | Bu | H |
| CHBr(CH₂)₃CH₃ | H | H | Bu | Me |
| CHBr(CH₂)₃CH₃ | H | H | Bu | Ph |
| CHCl(CH₂)₃CH₃ | H | H | Bu | H |
| CHCl(CH₂)₃CH₃ | H | H | Bu | Me |
| CHCl(CH₂)₃CH₃ | H | H | Bu | Ph |
| CHF(CH₂)₃CH₃ | H | H | Bu | H |
| CHF(CH₂)₃CH₃ | H | H | Bu | Me |
| CHF(CH₂)₃CH₃ | H | H | Bu | Ph |
| CO(CH₂)₃CH₃ | H | H | Bu | H |
| CO(CH₂)₃CH₃ | H | H | Bu | Me |
| CO(CH₂)₃CH₃ | H | H | Bu | Ph |
| C(=NOH)(CH₂)₃CH₃ | H | H | Bu | H |
| C(=NOH)(CH₂)₃CH₃ | H | H | Bu | Me |
| C(=NOH)(CH₂)₃CH₃ | H | H | Bu | Ph |
| C(OCH₂CH₂O)(CH₂)₃CH₃ | H | H | Bu | H |
| C(OCH₂CH₂O)(CH₂)₃CH₃ | H | H | Bu | Me |
| C(OCH₂CH₂O)(CH₂)₃CH₃ | H | H | Bu | Ph |
| =CH(CH₂)₃CH₃ | H | H | Bu | H |
| =CH(CH₂)₃CH₃ | H | H | Bu | Me |
| =CH(CH₂)₃CH₃ | H | H | Bu | Ph |
| CF₂(CH₂)₃CH₃ | H | H | Bu | H |
| CF₂(CH₂)₃CH₃ | H | H | Bu | Me |
| CF₂(CH₂)₃CH₃ | H | H | Bu | Ph |
| CH(OCOMe)(CH₂)₃CH₃ | H | H | Bu | H |
| CH(OCOMe)(CH₂)₃CH₃ | H | H | Bu | Me |
| CH(OCOMe)(CH₂)₃CH₃ | H | H | Bu | Ph |
| CMe(OH)(CH₂)₃CH₃ | H | H | Bu | H |
| CMe(OH)(CH₂)₃CH₃ | H | H | Bu | Me |
| CMe(OH)(CH₂)₃CH₃ | H | H | Bu | Ph |
| CH(OH)-i-Pr | H | H | Bu | H |
| CH(OH)-i-Bu | H | H | Bu | H |
| CH(OH)-s-Bu | H | H | Bu | H |
| CH(OH)-i-Pr | H | H | Bu | Me |
| CH(OH)-i-Bu | H | H | Bu | Me |
| CH(OH)-s-Bu | H | H | Bu | Me |
| CH(OH)-s-Bu | H | H | Bu | Ph |

TABLE 3

| R¹ | R² | R³ | R⁴ | X² | Y |
|---|---|---|---|---|---|
| Me | H | H | H | O | H |
| Et | H | H | H | O | H |
| Pr | H | H | H | O | H |
| Bu | H | H | H | O | H |
| Pen | H | H | H | O | H |
| Hex | H | H | H | O | H |
| $(CH_2)_6CH_3$ | H | H | H | O | H |
| $(CH_2)_7CH_3$ | H | H | H | O | H |
| $(CH_2)_8CH_3$ | H | H | H | O | H |
| $(CH_2)_9CH_3$ | H | H | H | O | H |
| Me | H | H | H | O | OH |
| Et | H | H | H | O | OH |
| Pr | H | H | H | O | OH |
| Bu | H | H | H | O | OH |
| Pen | H | H | H | O | OH |
| Hex | H | H | H | O | OH |
| $(CH_2)_6CH_3$ | H | H | H | O | OH |
| $(CH_2)_7CH_3$ | H | H | H | O | OH |
| $(CH_2)_8CH_3$ | H | H | H | O | OH |
| $(CH_2)_9CH_3$ | H | H | H | O | OH |
| Me | H | H | Me | O | H |
| Et | H | H | Me | O | H |
| Pr | H | H | Me | O | H |
| Bu | H | H | Me | O | H |
| Pen | H | H | Me | O | H |
| Hex | H | H | Me | O | H |
| Et | H | H | Et | O | H |
| Pr | H | H | Et | O | H |
| Bu | H | H | Et | O | H |
| Pen | H | H | Et | O | H |
| Hex | H | H | Et | O | H |
| Pr | H | H | Pr | O | H |
| Bu | H | H | Pr | O | H |
| Pen | H | H | Pr | O | H |
| $CH_2CH=CHCH_3$ | H | H | $CH_2CH=CHCH_3$ | O | H |
| $CH_2CH=CHCH_2CH_3$ | H | H | $CH_2CH=CHCH_2CH_3$ | O | H |
| $CH_2CH=CH_2$ | H | H | $CH_2CH=CH_2$ | O | OH |
| $CH_2CH=CHCH_3$ | H | H | $CH_2CH=CHCH_3$ | O | OH |
| $CH_2CH=CHCH_2CH_3$ | H | H | $CH_2CH=CHCH_2CH_3$ | O | OH |
| $CH_2CH=CH_2$ | $CH_2CH=CH_2$ | H | H | O | H |
| $CH_2CH=CH_2$ | H | $CH_2CH=CH_2$ | H | O | H |
| $CH_2CH=CH_2$ | $CH_2CH=CH_2$ | $CH_2CH=CH_2$ | $CH_2CH=CH_2$ | O | H |
| $CH_2C\equiv CH$ | H | H | H | O | H |
| $CH_2C\equiv CH$ | H | H | $CH_2C\equiv CH$ | O | H |
| $CH_2C\equiv CH$ | $CH_2C\equiv CH$ | H | H | O | H |
| $CH_2C\equiv CH$ | H | $CH_2C\equiv CH$ | H | O | H |
| $CH_2C\equiv CH$ | $CH_2C\equiv CH$ | $CH_2C\equiv CH$ | $CH_2C\equiv CH$ | O | H |
| $CH_2C\equiv CCH_3$ | H | H | H | O | OH |
| $CH_2C\equiv CCH_3$ | H | H | $CH_2C\equiv CCH_3$ | O | OH |
| $CH_2C\equiv CCH_3$ | $CH_2C\equiv CCH_3$ | H | H | O | OH |
| $CH_2C\equiv CCH_3$ | H | $CH_2C\equiv CCH_3$ | H | O | OH |
| $CH_2C\equiv CCH_3$ | $CH_2C\equiv CCH_3$ | $CH_2C\equiv CCH_3$ | $CH_2C\equiv CCH_3$ | O | OH |
| $CH(OH)CH_3$ | H | H | H | O | H |
| $CH(OH)CH_2CH_3$ | H | H | H | O | H |
| $CH(OH)(CH_2)_2CH_3$ | H | H | H | O | H |
| $CH(OH)(CH_2)_3CH_3$ | H | H | H | O | H |
| $CH(OH)(CH_2)_4CH_3$ | H | H | H | O | H |

TABLE 3-continued

| R$^1$ | R$^2$ | R$^3$ | R$^4$ | X$^2$ | Y |
|---|---|---|---|---|---|
| CH(OH)CH$_3$ | H | H | Bu | O | H |
| CH(OH)CH$_2$CH$_3$ | H | H | Bu | O | H |
| CH(OH)(CH$_2$)$_2$CH$_3$ | H | H | Bu | O | H |
| CH(OH)(CH$_2$)$_3$CH$_3$ | H | H | Bu | O | H |
| CH(OH)(CH$_2$)$_4$CH$_3$ | H | H | Bu | O | H |
| CH(OH)CH$_3$ | H | H | Bu | O | OH |
| CH(OH)CH$_2$CH$_3$ | H | H | Bu | O | OH |
| CH(OH)(CH$_2$)$_2$CH$_3$ | H | H | Bu | O | OH |
| CH(OH)(CH$_2$)$_3$CH$_3$ | H | H | Bu | O | OH |
| CH(OH)(CH$_2$)$_4$CH$_3$ | H | H | Bu | O | OH |
| CHBr(CH$_2$)$_3$CH$_3$ | H | H | Bu | O | H |
| CHBr(CH$_2$)$_3$CH$_3$ | H | H | Bu | O | OH |
| CHCl(CH$_2$)$_3$CH$_3$ | H | H | Bu | O | H |
| CHCl(CH$_2$)$_3$CH$_3$ | H | H | Bu | O | OH |
| CHF(CH$_2$)$_3$CH$_3$ | H | H | Bu | O | H |
| CHF(CH$_2$)$_3$CH$_3$ | H | H | Bu | O | OH |
| CO(CH$_2$)$_3$CH$_3$ | H | H | Bu | O | H |
| CO(CH$_2$)$_3$CH$_3$ | H | H | Bu | O | OH |
| Hex | H | H | Pr | O | H |
| Bu | H | H | Bu | O | H |
| Pen | H | H | Bu | O | H |
| Hex | H | H | Bu | O | H |
| Pen | H | H | Pen | O | H |
| Hex | H | H | Pen | O | H |
| Hex | H | H | Hex | O | H |
| Pr | Pr | H | H | O | H |
| Bu | Bu | H | H | O | H |
| Pen | Pen | H | H | O | H |
| Hex | Hex | H | H | O | H |
| Pr | Pr | H | H | O | OH |
| Bu | Bu | H | H | O | OH |
| Pen | Pen | H | H | O | OH |
| Hex | Hex | H | H | O | OH |
| Pr | H | Pr | H | O | H |
| Bu | H | Bu | H | O | H |
| Pen | H | Pen | H | O | H |
| Hex | H | Hex | H | O | H |
| Pr | H | Pr | H | O | OH |
| Bu | H | Bu | H | O | OH |
| Pen | H | Pen | H | O | OH |
| Hex | H | Hex | H | O | OH |
| CH=CH$_2$ | H | H | H | O | H |
| CH=CHCH$_3$ | H | H | H | O | H |
| CH=CHCH$_2$CH$_3$ | H | H | H | O | H |
| CH=CH(CH$_2$)$_2$CH$_3$ | H | H | H | O | H |
| CH=CH(CH$_2$)$_3$CH$_3$ | H | H | H | O | H |
| CH$_2$CH=CH$_2$ | H | H | H | O | H |
| CH$_2$CH=CHCH$_3$ | H | H | H | O | H |
| CH$_2$CH=CHCH$_2$CH$_3$ | H | H | H | O | H |
| CH$_2$CH=CH(CH$_2$)$_2$CH$_3$ | H | H | H | O | H |
| CH=CH$_2$ | H | H | H | O | OH |
| CH=CHCH$_3$ | H | H | H | O | OH |
| CH=CHCH$_2$CH$_3$ | H | H | H | O | OH |
| CH=CH(CH$_2$)$_2$CH$_3$ | H | H | H | O | OH |
| CH=CH(CH$_2$)$_3$CH$_3$ | H | H | H | O | OH |
| CH$_2$CH=CH$_2$ | H | H | H | O | OH |
| CH$_2$CH=CHCH$_3$ | H | H | H | O | OH |
| CH$_2$CH=CHCH$_2$CH$_3$ | H | H | H | O | OH |
| CH$_2$CH=CH(CH$_2$)$_2$CH$_3$ | H | H | H | O | OH |
| CH$_2$CH=CH$_2$ | H | H | CH$_2$CH=CH$_2$ | O | H |
| C(=NOH)(CH$_2$)$_3$CH$_3$ | H | H | Bu | O | H |
| C(=NOH)(CH$_2$)$_3$CH$_3$ | H | H | Bu | O | OH |
| C(OCH$_2$CH$_2$O)(CH$_2$)$_3$CH$_3$ | H | H | Bu | O | H |
| C(OCH$_2$CH$_2$O)(CH$_2$)$_3$CH$_3$ | H | H | Bu | O | OH |
| =CH(CH$_2$)$_3$CH$_3$ | H | H | Bu | O | H |
| =CH(CH$_2$)$_3$CH$_3$ | H | H | Bu | O | OH |

TABLE 3-continued

| R¹ | R² | R³ | R⁴ | X² | Y |
|---|---|---|---|---|---|
| CF₂(CH₂)₃CH₃ | H | H | Bu | O | H |
| CF₂(CH₂)₃CH₃ | H | H | Bu | O | OH |
| CH(OCOMC)(CH₂)₃CH₃ | H | H | Bu | O | H |
| CH(OCOMe)(CH₂)₃CH₃ | H | H | Bu | O | OH |
| CMe(OH)(CH₂)₃CH₃ | H | H | Bu | O | H |
| CMe(OH)(CH₂)₃CH₃ | H | H | Bu | O | OH |
| CH(OH)-i-Pr | H | H | Bu | O | H |
| CH(OH)-i-Bu | H | H | Bu | O | H |
| CH(OH)-s-Bu | H | H | Bu | O | H |
| CH(OH)-s-Pen | H | H | Bu | O | H |
| CH(OH)-i-Pr | H | H | Bu | O | OH |
| CH(OH)-i-Bu | H | H | Bu | O | OH |
| CH(OH)-s-Bu | H | H | Bu | O | OH |
| CH(OH)-s-Pen | H | H | Bu | O | OH |
| CH(OH)(CH₂)₃CH₃ | H | H | Bu | NH | H |
| CH(OH)(CH₂)₃CH₃ | H | H | Bu | NMe | H |
| CH(OH)(CH₂)₃CH₃ | H | H | Bu | NPh | H |
| CH(OH)(CH₂)₃CH₃ | H | H | Bu | NPh-4-Cl | H |
| CH(OH)(CH₂)₃CH₃ | H | H | Bu | NPh-4-Br | H |
| CH(OH)(CH₂)₃CH₃ | H | H | Bu | NPh-4-Me | H |
| CH(OH)(CH₂)₃CH₃ | H | H | Bu | NPh-4-OMe | H |
| CH(OH)(CH₂)₃CH₃ | H | H | Bu | NCH₂Ph | H |
| CH(OH)(CH₂)₃CH₃ | H | H | Bu | NCH₂Ph-4-Cl | H |

TABLE 4

| R¹ | R² | R³ | R⁴ | A¹ | A² | A³ | A⁴ |
|---|---|---|---|---|---|---|---|
| Me | H | H | H | COOH | COOH | COOH | COOH |
| Et | H | H | H | COOH | COOH | COOH | COOH |
| Pr | H | H | H | COOH | COOH | COOH | COOH |
| Bu | H | H | H | COOH | COOH | COOH | COOH |
| Pen | H | H | H | COOH | COOH | COOH | COOH |
| Hex | H | H | H | COOH | COOH | COOH | COOH |
| (CH₂)₆CH₃ | H | H | H | COOH | COOH | COOH | COOH |
| (CH₂)₇CH₃ | H | H | H | COOH | COOH | COOH | COOH |
| (CH₂)₈CH₃ | H | H | H | COOH | COOH | COOH | COOH |
| (CH₂)₉CH₃ | H | H | H | COOH | COOH | COOH | COOH |
| Me | H | H | H | COOH | COOMe | COOH | COOMe |
| Et | H | H | H | COOH | COOMe | COOH | COOMe |
| Pr | H | H | H | COOH | COOMe | COOH | COOMe |
| Bu | H | H | H | COOH | COOMe | COOH | COOMe |
| Pen | H | H | H | COOH | COOMe | COOH | COOMe |
| Hex | H | H | H | COOH | COOMe | COOH | COOMe |
| (CH₂)₆CH₃ | H | H | H | COOH | COOMe | COOH | COOMe |
| (CH₂)₇CH₃ | H | H | H | COOH | COOMe | COOH | COOMe |
| (CH₂)₈CH₃ | H | H | H | COOH | COOMe | COOH | COOMe |
| (CH₂)₉CH₃ | H | H | H | COOH | COOMe | COOH | COOMe |
| Me | H | H | H | COOH | CONH₂ | COOH | CONH₂ |
| Et | H | H | H | COOH | CONH₂ | COOH | CONH₂ |
| Pr | H | H | H | COOH | CONH₂ | COOH | CONH₂ |
| Bu | H | H | H | COOH | CONH₂ | COOH | CONH₂ |
| Pen | H | H | H | COOH | CONH₂ | COOH | CONH₂ |

TABLE 4-continued

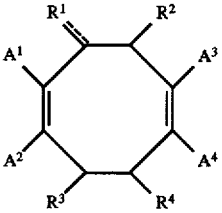

| R¹ | R² | R³ | R⁴ | A¹ | A² | A³ | A⁴ |
|---|---|---|---|---|---|---|---|
| Hex | H | H | H | COOH | CONH₂ | COOH | CONH₂ |
| (CH₂)₆CH₃ | H | H | H | COOH | CONH₂ | COOH | CONH₂ |
| (CH₂)₇CH₃ | H | H | H | COOH | CONH₂ | COOH | CONH₂ |
| (CH₂)₈CH₃ | H | H | H | COOH | CONH₂ | COOH | CONH₂ |
| (CH₂)₉CH₃ | H | H | H | COOH | CONH₂ | COOH | CONH₂ |
| Me | H | H | H | COOMe | COOMe | COOMe | COOMe |
| Et | H | H | H | COOMe | COOMe | COOMe | COOMe |
| Pr | H | H | H | COOMe | COOMe | COOMe | COOMe |
| Bu | H | H | H | COOMe | COOMe | COOMe | COOMe |
| Pen | H | H | H | COOMe | COOMe | COOMe | COOMe |
| Hex | H | H | H | COOMe | COOMe | COOMe | COOMe |
| (CH₂)₆CH₃ | H | H | H | COOMe | COOMe | COOMe | COOMe |
| (CH₂)₇CH₃ | H | H | H | COOMe | COOMe | COOMe | COOMe |
| (CH₂)₈CH₃ | H | H | H | COOMe | COOMe | COOMe | COOMe |
| (CH₂)₉CH₃ | H | H | H | COOMe | COOMe | COOMe | COOMe |
| Me | H | H | H | COOEt | COOEt | COOEt | COOEt |
| Et | H | H | H | COOEt | COOEt | COOEt | COOEt |
| Pr | H | H | H | COOEt | COOEt | CCOEt | COOEt |
| Bu | H | H | H | COOEt | COOEt | COOEt | COOEt |
| Pen | H | H | H | COOEt | COOEt | COOEt | COOEt |
| Hex | H | H | H | COOEt | COOEt | COOEt | COOEt |
| (CH₂)₆CH₃ | H | H | H | COOEt | COOEt | COOEt | COOEt |
| (CH₂)₇CH₃ | H | H | H | COOEt | COOEt | COOEt | COOEt |
| (CH₂)₈CH₃ | H | H | H | COOEt | COOEt | COOEt | COOEt |
| (CH₂)₉CH₃ | H | H | H | COOEt | COOEt | COOEt | COOEt |
| Me | H | H | H | COOH | CONHPh | COOH | CONHPh |
| Et | H | H | H | COOH | CONHPh | COOH | CONHPh |
| Pr | H | H | H | COOH | CONHPh | COOH | CONHPh |
| Bu | H | H | H | COOH | CONHPh | COOH | CONHPh |
| Pen | H | H | H | COOH | CONHPh | COOH | CONHPh |
| Hex | H | H | H | COOH | CONHPh | COOH | CONHPh |
| (CH₂)₆CH₃ | H | H | H | COOH | CONHPh | COOH | CONHPh |
| (CH₂)₇CH₃ | H | H | H | COOH | CONHPh | COOH | CONHPh |
| (CH₂)₈CH₃ | H | H | H | COOH | CONHPh | COOH | CONHPh |
| (CH₂)₉CH₃ | H | H | H | COOH | CONHPh | COOH | CONHPh |
| Me | H | H | H | COOH | COOPh | COOH | COOPh |
| Et | H | H | H | COOH | COOPh | COOH | COOPh |
| Pr | H | H | H | COOH | COOPh | COOH | COOPh |
| Bu | H | H | H | COOH | COOPh | COOH | COOPh |
| Pen | H | H | H | COOH | COOPh | COOH | COOPh |
| Hex | H | H | H | COOH | COOPh | COOH | COOPh |
| (CH₂)₆CH₃ | H | H | H | COOH | COOPh | COOH | COOPh |
| (CH₂)₇CH₃ | H | H | H | COOH | COOPh | COOH | COOPh |
| (CH₂)₈CH₃ | H | H | H | COOH | COOPh | COOH | COOPh |
| (CH₂)₉CH₃ | H | H | H | COOH | COOPh | COOH | COOPh |
| Me | H | H | Me | COOMe | COOMe | COOMe | COOMe |
| Et | H | H | Me | COOMe | COOMe | COOMe | COOMe |
| Pr | H | H | Me | COOMe | COOMe | COOMe | COOMe |
| Bu | H | H | Me | COOMe | COOMe | COOMe | COOMe |
| Pen | H | H | Me | COOMe | COOMe | COOMe | COOMe |
| Hex | H | H | Me | COOMe | COOMe | COOMe | COOMe |
| Et | H | H | Et | COOMe | COOMe | COOMe | COOMe |
| Pr | H | H | Et | COOMe | COOMe | COOMe | COOMe |
| Bu | H | H | Et | COOMe | COOMe | COOMe | COOMe |
| Pen | H | H | Et | COOMe | COOMe | COOMe | COOMe |
| Hex | H | H | Et | COOMe | COOMe | COOMe | COOMe |
| Pr | H | H | Pr | COOMe | COOMe | COOMe | COOMe |
| Bu | H | H | Pr | COOMe | COOMe | COOMe | COOMe |
| Pen | H | H | Pr | COOMe | COOMe | COOMe | COOMe |
| Hex | H | H | Pr | COOMe | COOMe | COOMe | COOMe |
| Bu | H | H | Bu | COOMe | COOMe | COOMe | COOMe |
| Pen | H | H | Bu | COOMe | COOMe | COOMe | COOMe |
| Hex | H | H | Bu | COOMe | COOMe | COOMe | COOMe |
| Pen | H | H | Pen | COOMe | COOMe | COOMe | COOMe |
| Hex | H | H | Pen | COOMe | COOMe | COOMe | COOMe |
| Hex | H | H | Hex | COOMe | COOMe | COOMe | COOMe |

TABLE 4-continued

| R¹ | R² | R³ | R⁴ | A¹ | A² | A³ | A⁴ |
|---|---|---|---|---|---|---|---|
| Pr | Pr | H | H | COOMe | COOMe | COOMe | COOMe |
| Bu | Bu | H | H | COOMe | COOMe | COOMe | COOMe |
| Pen | Pen | H | H | COOMe | COOMe | COOMe | COOMe |
| Hex | Hex | H | H | COOMe | COOMe | COOMe | COOMe |
| Pr | Pr | H | H | COOEt | COOEt | COOEt | COOEt |
| Bu | Bu | H | H | COOEt | COOEt | COOEt | COOEt |
| Pen | Pen | H | H | COOEt | COOEt | COOEt | COOEt |
| Hex | Hex | H | H | COOEt | COOEt | COOEt | COOEt |
| Pr | H | Pr | H | COOMe | COOMe | COOMe | COOMe |
| Bu | H | Bu | H | COoMe | COOMe | COOMe | COOMe |
| Pen | H | Pen | H | COOMe | COOMe | COOMe | COOMe |
| Hex | H | Hex | H | COOMe | COOMe | COOMe | COOMe |
| Pr | H | Pr | H | COOEt | COOEt | COOEt | COOEt |
| Bu | H | Bu | H | COOEt | COOEt | COOEt | COOEt |
| Pen | H | Pen | H | COOEt | COOEt | COOEt | COOEt |
| Hex | H | Hex | H | COOEt | COOEt | COOEt | COOEt |
| Pr | H | Pr | H | COOPh | COOPh | COOPh | COOPh |
| Bu | H | Bu | H | COOPh | COOPh | COOPh | COOPh |
| Pen | H | Pen | H | COOPh | COOPh | COOPh | COOPh |
| Hex | H | Hex | H | COOPh | COOPh | COOPh | COOPh |
| CH=CH₂ | H | H | H | COOH | COOH | COOH | COOH |
| CH=CHCH₃ | H | H | H | COOH | COOH | COOH | COOH |
| CH=CHCH₂CH₃ | H | H | H | COOH | COOH | COOH | COOH |
| CH=CH(CH₂)₂CH₃ | H | H | H | COOH | COOH | COOH | COOH |
| CH=CH(CH₂)₃CH₃ | H | H | H | COOH | COOH | COOH | COOH |
| CH₂CH=CH₂ | H | H | H | COOH | COOH | COOH | COOH |
| CH₂CH=CHCH₃ | H | H | H | COOH | COOH | COOH | COOH |
| CH₂CH=CHCH₂CH₃ | H | H | H | COOH | COOH | COOH | COOH |
| CH₂CH=CH(CH₂)₂CH₃ | H | H | H | COOH | COOH | COOH | COOH |
| CH=CH₂ | H | H | H | COOMe | COOMe | COOMe | COOMe |
| CH=CHCH₃ | H | H | H | COOMe | COOMe | COOMe | COOMe |
| CH=CHCH₂CH₃ | H | H | H | COOMe | COOMe | COOMe | COOMe |
| CH=CH(CH₂)₂CH₃ | H | H | H | COOMe | COOMe | COOMe | COOMe |
| CH=CH(CH₂)₃CH₃ | H | H | H | COOMe | COOMe | COOMe | COOMe |
| CH₂CH=CH₂ | H | H | H | COOMe | COOMe | COOMe | COOMe |
| CH₂CH=CHCH₃ | H | H | H | COOMe | COOMe | COOMe | COOMe |
| CH₂CH=CHCH₂CH₃ | H | H | H | COOMe | COOMe | COOMe | COOMe |
| CH₂CH=CH(CH₂)₂CH₃ | H | H | H | COOMe | COOMe | COOMe | COOMe |
| CH=CH₂ | H | H | H | CONH₂ | CONH₂ | CONH₂ | CONH₂ |
| CH=CHCH₃ | H | H | H | CONH₂ | CONH₂ | CONH₂ | CONH₂ |
| CH=CHCH₂CH₃ | H | H | H | CONH₂ | CONH₂ | CONH₂ | CONH₂ |
| CH=CH(CH₂)₂CH₃ | H | H | H | CONH₂ | CONH₂ | CONH₂ | CONH₂ |
| CH=CH(CH₂)₃CH₃ | H | H | H | CONH₂ | CONH₂ | CONH₂ | CONH₂ |
| CH₂CH=CH₂ | H | H | H | CONH₂ | CONH₂ | CONH₂ | CONH₂ |
| CH₂CH=CHCH₃ | H | H | H | CONH₂ | CONH₂ | CONH₂ | CONH₂ |
| CH₂CH=CHCH₂CH₃ | H | H | H | CONH₂ | CONH₂ | CONH₂ | CONH₂ |
| CH₂CH=CH(CH₂)₂CH₃ | H | H | H | CONH₂ | CONH₂ | CONH₂ | CONH₂ |
| CH=CH₂ | H | H | H | CONHPh | CONHPh | CONHPh | CONHPh |
| CH=CHCH₃ | H | H | H | CONHPh | CONHPh | CONHPh | CONHPh |
| CH=CHCH₂CH₃ | H | H | H | CONHPh | CONHPh | CONHPh | CONHPh |
| CH=CH(CH₂)₂CH₃ | H | H | H | CONHPh | CONHPh | CONHPh | CONHPh |
| CH=CH(CH₂)₃CH₃ | H | H | H | CONHPh | CONHPh | CONHPh | CONHPh |
| CH₂CH=CH₂ | H | H | H | CONHPh | CONHPh | CONHPh | CONHPh |
| CH₂CH=CHCH₃ | H | H | H | CONHPh | CONHPh | CONHPh | CONHPh |
| CH₂CH=CHCH₂CH₃ | H | H | H | CONHPh | CONHPh | CONHPh | CONHPh |
| CH₂CH=CH(CH₂)₂CH₃ | H | H | H | CONHPh | CONHPh | CONHPh | CONHPh |
| CH₂CH=CH₂ | H | H | CH₂CH=CH₂ | COOMe | COOMe | COOMe | COOMe |
| CH₂CH=CHCH₃ | H | H | CH₂CH=CHCH₃ | COOMe | COOMe | COOMe | COOMe |
| CH₂CH=CHCH₂CH₃ | H | H | CH₂CH=CHCH₂CH₃ | COOMe | COOMe | COOMe | COOMe |
| CH₂CH=CH₂ | H | H | CH₂CH=CH₂ | COOEt | COOEt | COOEt | COOEt |
| CH₂CH=CHCH₃ | H | H | CH₂CH=CHCH₃ | COOEt | COOEt | COOEt | COOEt |
| CH₂CH=CHCH₂CH₃ | H | H | CH₂CH=CHCH₂CH₃ | COOEt | COOEt | COOEt | COOEt |
| CH₂CH=CH₂ | H | H | CH₂CH=CH₂ | CONH₂ | CONH₂ | CONH₂ | CONH₂ |
| CH₂CH=CHCH₃ | H | H | CH₂CH=CHCH₃ | CONH₂ | CONH₂ | CONH₂ | CONH₂ |
| CH₂CH=CHCH₂CH₃ | H | H | CH₂CH=CHCH₂CH₃ | CONH₂ | CONH₂ | CONH₂ | CONH₂ |
| CH₂CH=CH₂ | CH₂CH=CH₂ | H | H | COOMe | COOMe | COOMe | COOMe |

TABLE 4-continued

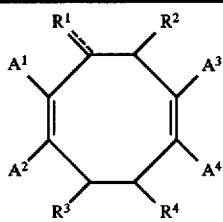

| R¹ | R² | R³ | R⁴ | A¹ | A² | A³ | A⁴ |
|---|---|---|---|---|---|---|---|
| CH₂CH=CH₂ | H | CH₂CH=CH₂ | H | COOMe | COOMe | COOMe | COOMe |
| CH₂CH=CH₂ | CH₂CH=CH₂ | CH₂CH=CH₂ | CH₂CH=CH₂ | COOMe | COOMe | COOMe | COOMe |
| CH₂C≡CH | H | H | H | COOMe | COOMe | COOMe | COOMe |
| CH₂C≡CH | H | H | CH₂C≡CH | COOMe | COOMe | COOMe | COOMe |
| CH₂C≡CH | CH₂C≡CH | H | H | COOMe | COOMe | COOMe | COOMe |
| CH₂C≡CH | H | CH₂C≡CH | H | COOMe | COOMe | COOMe | COOMe |
| CH₂C≡CH | CH₂C≡CH | CH₂C≡CH | CH₂C≡CH | COOMe | COOMe | COOMe | COOMe |
| CH₂C≡CCH₃ | H | H | H | COOMe | COOMe | COOMe | COOMe |
| CH₂C≡CCH₃ | H | H | CH₂C≡CCH₃ | COOMe | COOMe | COOMe | COOMe |
| CH₂C≡CCH₃ | CH₂C≡CCH₃ | H | H | COOMe | COOMe | COOMe | COOMe |
| CH₂C≡CCH₃ | H | CH₂C≡CCH₃ | H | COOMe | COOMe | COOMe | COOMe |
| CH(OH)CH₃ | H | H | H | COOMe | COOMe | COOMe | COOMe |
| CH(OH)CH₂CH₃ | H | H | H | COOMe | COOMe | COOMe | COOMe |
| CH(OH)(CH₂)₂CH₃ | H | H | H | COOMe | COOMe | COOMe | COOMe |
| CH(OH)(CH₂)₃CH₃ | H | H | H | COOMe | COOMe | COOMe | COOMe |
| CH(OH)(CH₂)₄CH₃ | H | H | H | COOMe | COOMe | COOMe | COOMe |
| CH(OH)CH₃ | H | H | Bu | COOMe | COOMe | COOMe | COOMe |
| CH(OH)CH₂CH₃ | H | H | Bu | COOMe | COOMe | COOMe | COOMe |
| CH(OH)(CH₂)₂CH₃ | H | H | Bu | COOMe | COOMe | COOMe | COOMe |
| CH(OH)(CH₂)₃CH₃ | H | H | Bu | COOMe | COOMe | COOMe | COOMe |
| CH(OH)(CH₂)₄CH₃ | H | H | Bu | COOMe | COOMe | COOMe | COOMe |
| CH(OH)CH₃ | H | H | Bu | COOEt | COOEt | COOEt | COOEt |
| CH(OH)CH₂CH₃ | H | H | Bu | COOEt | COOEt | COOEt | COOEt |
| CH(OH)(CH₂)₂CH₃ | H | H | Bu | COOEt | COOEt | COOEt | COOEt |
| CH(OH)(CH₂)₃CH₃ | H | H | Bu | COOEt | COOEt | COOEt | COOEt |
| CH(OH)(CH₂)₄CH₃ | H | H | Bu | COOEt | COOEt | COOEt | COOEt |
| CH(OH)CH₃ | H | H | Bu | CONH₂ | CONH₂ | CONH₂ | CONH₂ |
| CH(OH)CH₂CH₃ | H | H | Bu | CONH₂ | CONH₂ | CONH₂ | CONH₂ |
| CH(OH)(CH₂)₂CH₃ | H | H | Bu | CONH₂ | CONH₂ | CONH₂ | CONH₂ |
| CH(OH)(CH₂)₃CH₃ | H | H | Bu | CONH₂ | CONH₂ | CONH₂ | CONH₂ |
| CH(OH)(CH₂)₄CH₃ | H | H | Bu | CONH₂ | CONH₂ | CONH₂ | CONH₂ |
| CHBr(CH₂)₃CH₃ | H | H | Bu | COOMe | COOMe | COOMe | COOMe |
| CHBr(CH₂)₃CH₃ | H | H | Bu | COOEt | COOEt | COOEt | COOEt |
| CHBr(CH₂)₃CH₃ | H | H | Bu | CONH₂ | CONH₂ | CONH₂ | CONH₂ |
| CHCl(CH₂)₃CH₃ | H | H | Bu | COOMe | COOMe | COOMe | COOMe |
| CHCl(CH₂)₃CH₃ | H | H | Bu | COOEt | COOEt | COOEt | COOEt |
| CHCl(CH₂)₃CH₃ | H | H | Bu | CONH₂ | CONH₂ | CONH₂ | CONH₂ |
| CHF(CH₂)₃CH₃ | H | H | Bu | COOMe | COOMe | COOMe | COOMe |
| CHF(CH₂)₃CH₃ | H | H | Bu | COOEt | COOEt | COOEt | COOEt |
| CHF(CH₂)₃CH₃ | H | H | Bu | CONH₂ | CONH₂ | CONH₂ | CONH₂ |
| CO(CH₂)₃CH₃ | H | H | Bu | COOMe | COOMe | COOMe | COOMe |
| CO(CH₂)₃CH₃ | H | H | Bu | COOEt | COOEt | COOEt | COOEt |
| CO(CH₂)₃CH₃ | H | H | Bu | CONH₂ | CONH₂ | CONH₂ | CONH₂ |
| C(=NOH)(CH₂)₃CH₃ | H | H | Bu | COOMe | COOMe | COOMe | COOMe |
| C(=NOH)(CH₂)₃CH₃ | H | H | Bu | COOEt | COOEt | COOEt | COOEt |
| C(=NOH)(CH₂)₃CH₃ | H | H | Bu | CONH₂ | CONH₂ | CONH₂ | CONH₂ |
| C(OCH₂CH₂O)(CH₂)₃CH₃ | H | H | Bu | COOMe | COOMe | COOMe | COOMe |
| C(OCH₂CH₂O)(CH₂)₃CH₃ | H | H | Bu | COOEt | COOEt | COOEt | COOEt |
| C(OCH₂CH₂O)(CH₂)₃CH₃ | H | H | Bu | CONH₂ | CONH₂ | CONH₂ | CONH₂ |
| =CH(CH₂)₃CH₃ | H | H | Bu | COOMe | COOMe | COOMe | COOMe |
| =CH(CH₂)₃CH₃ | H | H | Bu | COOEt | COOEt | COOEt | COOEt |
| =CH(CH₂)₃CH₃ | H | H | Bu | CONH₂ | CONH₂ | CONH₂ | CONH₂ |
| CF₂(CH₂)₃CH₃ | H | H | Bu | COOMe | COOMe | COOMe | COOMe |
| CF₂(CH₂)₃CH₃ | H | H | Bu | COOEt | COOEt | COOEt | COOEt |
| CF₂(CH₂)₃CH₃ | H | H | Bu | CONH₂ | CONH₂ | CONH₂ | CONH₂ |
| CH(OCOMe)(CH₂)₃CH₃ | H | H | Bu | COOMe | COOMe | COOMe | COOMe |
| CH(OCOMe)(CH₂)₃CH₃ | H | H | Bu | COOEt | COOEt | COOEt | COOEt |
| CH(OCOMe)(CH₂)₃CH₃ | H | H | Bu | CONH₂ | CONH₂ | CONH₂ | CONH₂ |

TABLE 4-continued

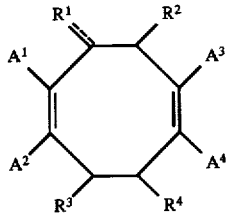

| R¹ | R² | R³ | R⁴ | A¹ | A² | A³ | A⁴ |
|---|---|---|---|---|---|---|---|
| CMe(OH)(CH₂)₃CH₃ | H | H | Bu | COOMe | COOMe | COOMe | COOMe |
| CMe(OH)(CH₂)₃CH₃ | H | H | Bu | COOEt | COOEt | COOEt | COOEt |
| CMe(OH)(CH₂)₃CH₃ | H | H | Bu | CONH₂ | CONH₂ | CONH₂ | CONH₂ |
| CH(OH)-i-Pr | H | H | Bu | COOMe | COOMe | COOMe | COOMe |
| CH(OH)-i-Bu | H | H | Bu | COOMe | COOMe | COOMe | COOMe |
| CH(OH)-s-Bu | H | H | Bu | COOMe | COOMe | COOMe | COOMe |
| CH(OH)-i-Pr | H | H | Bu | COOEt | COOEt | COOEt | COOEt |
| CH(OH)-i-Bu | H | H | Bu | COOEt | COOEt | COOEt | COOEt |
| CH(OH)-s-Bu | H | H | Bu | COOEt | COOEt | COOEt | COOEt |
| CH(OH)-s-Bu | H | H | Bu | CONH₂ | CONH₂ | CONH₂ | CONH₂ |
| CH(OH)-s-Pen | H | H | Bu | CONH₂ | CONH₂ | CONH₂ | CONH₂ |
| CH(OH)(CH₂)₃CH₃ | H | H | Bu | COOPh | COOPh | COOPh | COOPh |
| CH(OH)(CH₂)₃CH₃ | H | H | Bu | CONHPh | CONHPh | CONHPh | CONHPh |
| CH(OH)(CH₂)₃CH₃ | H | H | Bu | COOH | COOMe | COOH | COOMe |
| CH(OH)(CH₂)₃CH₃ | H | H | Bu | COOH | CONH₂ | COOH | CONH₂ |
| CH(OH)(CH₂)₃CH₃ | H | H | Bu | COOH | CONHMe | COOH | CONHMe |
| CH(OH)(CH₂)₃CH₃ | H | H | Bu | COOH | CONMe₂ | COOH | CONMe₂ |
| CH(OH)(CH₂)₃CH₃ | H | H | Bu | COOH | CONHEt | COOH | CONHEt |
| Cl | H | H | H | COOMe | COOMe | COOMe | COOMe |
| Cl | Cl | H | H | COOMe | COOMe | COOMe | COOMe |
| Cl | H | Cl | H | COOMe | COOMe | COOMe | COOMe |
| Cl | H | H | Cl | COOMe | COOMe | COOMe | COOMe |
| Cl | Cl | Cl | H | COOMe | COOMe | COOMe | COOMe |
| Cl | Cl | Cl | Cl | COOMe | COOMe | COOMe | COOMe |
| Br | H | H | H | COOMe | COOMe | COOMe | COOMe |
| Br | Br | H | H | COOMe | COOMe | COOMe | COOMe |
| Br | H | Br | H | COOMe | COOMe | COOMe | COOMe |
| Br | H | H | Br | COOMe | COOMe | COOMe | COOMe |
| Br | Br | Br | H | COOMe | COOMe | COOMe | COOMe |
| Br | Br | Br | Br | COOMe | COOMe | COOMe | COOMe |
| I | H | H | H | COOMe | COOMe | COOMe | COOMe |
| I | I | H | H | COOMe | COOMe | COOMe | COOMe |
| I | H | I | H | COOMe | COOMe | COOMe | COOMe |
| I | H | H | I | COOMe | COOMe | COOMe | COOMe |
| I | I | I | H | COOMe | COOMe | COOMe | COOMe |
| I | I | I | I | COOMe | COOMe | COOMe | COOMe |
| Br | H | H | Me | COOMe | COOMe | COOMe | COOMe |
| Br | H | H | Et | COOMe | COOMe | COOMe | COOMe |
| Br | H | H | Pr | COOMe | COOMe | COOMe | COOMe |
| Br | H | H | Bu | COOMe | COOMe | COOMe | COOMe |
| Br | H | H | Pen | COOMe | COOMe | COOMe | COOMe |
| Br | H | H | Hex | COOMe | COOMe | COOMe | COOMe |
| Br | H | Me | H | COOMe | COOMe | COOMe | COOMe |
| Br | H | Et | H | COOMe | COOMe | COOMe | COOMe |
| Br | H | Pr | H | COOMe | COOMe | COOMe | COOMe |
| Br | H | Bu | H | COOMe | COOMe | COOMe | COOMe |
| Br | H | Pen | H | COOMe | COOMe | COOMe | COOMe |
| Br | H | Hex | H | COOMe | COOMe | COOMe | COOMe |

TABLE 5

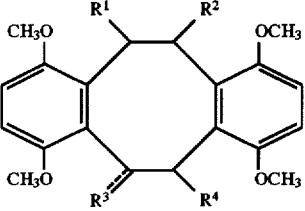

| R¹ | R² | R³ | R⁴ |
|---|---|---|---|
| CH(OH)(CH₂)₃CH₃ | H | OH | H |
| CH(OH)(CH₂)₃CH₃ | H | =O | H |
| CH(OH)(CH₂)₃CH₃ | H | =O | Me |
| CH(OH)(CH₂)₃CH₃ | H | =O | Et |
| CH(OH)(CH₂)₃CH₃ | H | =O | Pr |
| CH(OH)(CH₂)₃CH₃ | H | =O | Bu |
| CH(OH)(CH₂)₃CH₃ | H | =O | Pen |
| CH(OH)(CH₂)₃CH₃ | H | =O | Hex |
| CH(OH)(CH₂)₃CH₃ | H | OH | Me |
| CH(OH)(CH₂)₃CH₃ | H | OH | Et |
| CH(OH)(CH₂)₃CH₃ | H | OH | Pr |
| CH(OH)(CH₂)₃CH₃ | H | OH | Bu |
| CH(OH)(CH₂)₃CH₃ | H | OH | Pen |
| CH(OH)(CH₂)₃CH₃ | H | OH | Hex |
| Pen | H | =O | H |
| Pen | H | =O | Me |
| Pen | H | =O | Et |
| Pen | H | =O | Pr |
| Pen | H | =O | Bu |
| Pen | H | =O | Pen |
| Pen | H | =O | Hex |
| CH(OH)(CH₂)₃CH₃ | H | H | H |
| CH(OH)(CH₂)₃CH₃ | H | H | Me |
| CH(OH)(CH₂)₃CH₃ | H | H | Et |
| CH(OH)(CH₂)₃CH₃ | H | H | Pr |
| CH(OH)(CH₂)₃CH₃ | H | H | Bu |
| CH(OH)(CH₂)₃CH₃ | H | H | Pen |
| CHF(CH₂)₃CH₃ | H | =O | H |
| CHF(CH₂)₃CH₃ | H | =O | Me |
| CHF(CH₂)₃CH₃ | H | =O | Et |
| CHF(CH₂)₃CH₃ | H | =O | Pr |
| CHF(CH₂)₃CH₃ | H | =O | Bu |
| CHF(CH₂)₃CH₃ | H | =O | Pen |
| CHCl(CH₂)₃CH₃ | H | =O | H |
| CHBr(CH₂)₃CH₃ | H | =O | H |
| CH(OCH₃)(CH₂)₃CH₃ | H | =O | H |
| CH(OCH₂Ph)(CH₂)₃CH₃ | H | =O | H |
| CH(OCH₂OCH₃)(CH₂)₃CH₃ | H | =O | H |
| CH(OTHP)(CH₂)₃CH₃ | H | =O | H |
| CH(OSiMe₃)(CH₂)₃CH₃ | H | =O | H |
| CH(OCOPh)(CH₂)₃CH₃ | H | =O | H |
| CHCl(CH₂)₃CH₃ | H | =O | Bu |
| CHBr(CH₂)₃CH₃ | H | =O | Bu |
| CH(OCH₃)(CH₂)₃CH₃ | H | =O | Bu |
| CH(OCH₂Ph)(CH₂)₃CH₃ | H | =O | Bu |
| CH(OCH₂OCH₃)(CH₂)₃CH₃ | H | =O | Bu |
| CH(OTHP)(CH₂)₃CH₃ | H | =O | Bu |
| CH(OSiMe₃)(CH₂)₃CH₃ | H | =O | Bu |
| CH(OCOPh)(CH₂)₃CH₃ | H | =O | Bu |
| CHCl(CH₂)₃CH₃ | H | H | Bu |
| CHBr(CH₂)₃CH₃ | H | H | Bu |
| CH(OCH₃)(CH₂)₃CH₃ | H | H | Bu |
| CH(OCH₂Ph)(CH₂)₃CH₃ | H | H | Bu |
| CH(OCH₂OCH₃)(CH₂)₃CH₃ | H | H | Bu |
| CH(OTHP)(CH₂)₃CH₃ | H | H | Bu |
| CH(OSiMe₃)(CH₂)₃CH₃ | H | H | Bu |
| CH(OCOPh)(CH₂)₃CH₃ | H | H | Bu |

Methods for producing the compounds of the present invention are mentioned below.

Production Method 1

A method is disclosed in Japanese Patent Application Laid-open No. 6-184157, U.S. Pat. No. 5,346,919 and European Patent Application Laid-open No. 582,267, comprising incubating microorganisms of a strain belonging to the genus Zopfiella, preferably those of *Zopfiella curvata* to produce Compound A (Zopfiellin) of the following structural formula (A) in the culture followed by isolating the product from the culture through various means of concentration under reduced pressure, freeze-drying, extraction with an organic solvent such as methanol, ethanol, propanol, butanol, acetone, ethyl acetate, chloroform or benzene, chromatography with an adsorbent such as an ion-exchange resin, a non-ionic adsorbing resin, active charcoal, silica gel or alumina, gelfiltration and crystallization, which can be employed singly or in combination or repetition thereof in any desired order.

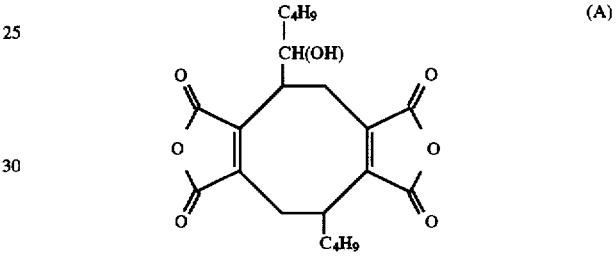

(A)

Starting from Compound A, the compounds of the present invention can be obtained by various chemical reactions of the Compound A.

1. Conversion of acid anhydride moiety 1-(1). Carboxylic acids, esters, amides and imido compounds Compound A can be hydrolyzed under acidic conditions (for example, in the presence of hydrochloric acid or sulfuric acid) or alkaline conditions (for example, in the presence of sodium hydroxide or potassium hydroxide) to produce carboxylic acid derivatives.

The resulting carboxylic acid derivative can be reacted with any of alcohols such as methanol and ethanol, or amines such as ammonia, methylamine, dimethylamine and aniline, in the presence of a condensing agent such as DCC to produce ester derivatives and amide derivatives. When Compound A is reacted with any of such alcohols or amines optionally in the presence of a base such as potassium carbonate or t-BuOK as added thereto, then partial esters, amides and imido derivatives can be produced.

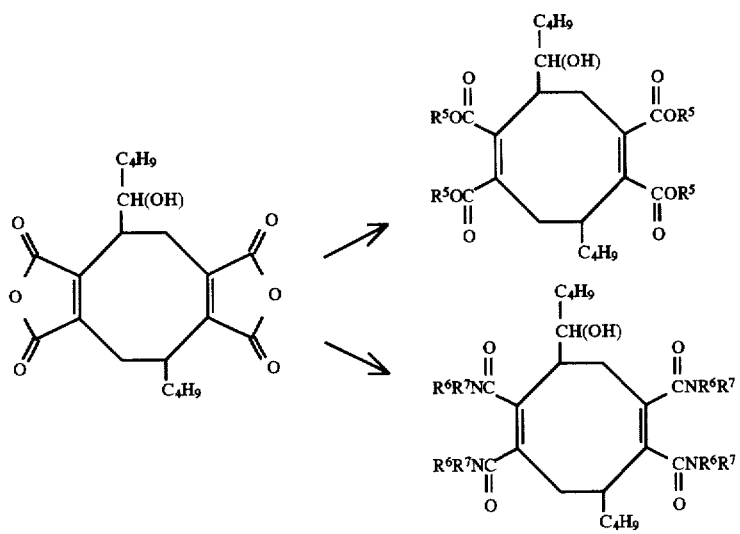

In these formulae, $R^5$, $R^6$ and $R^7$ have the same meanings as defined above.

1-(2). Lactone derivatives

Compound A can be reduced with a reducing agent, such as lithium aluminium hydride ($LiAlH_4$), to produce lactone derivatives.

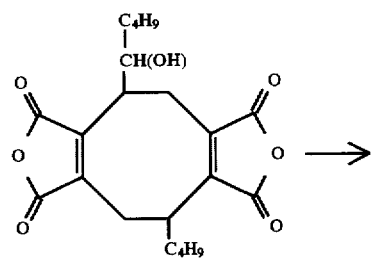

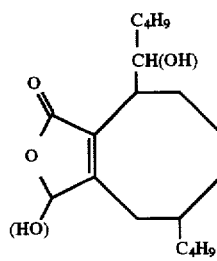

2. Conversion of chain-structured moiety 2-(1). Halide compounds

The hydroxyl group in Compound A and its equivalent analogs (these mean modifications to be derived from Compound A by converting its acid anhydride moiety into dicarboxylic acids, esters, amides and imides) can be converted into a halide by means of conventional methods for converting a hydroxyl group into a halide.

The reactants to be employed herein includes, for example, a fluorinating agent such as diethylaminosulfur trifluoride (DAST), a chlorinating agent such as thionyl chloride ($SOCl_2$) or carbon tetrachloride-triphenylphosphine ($CCl_4$—$PPh_3$), and a brominating agent such as bromine-triphenylphosphine ($Br_2$—$PPh_3$).

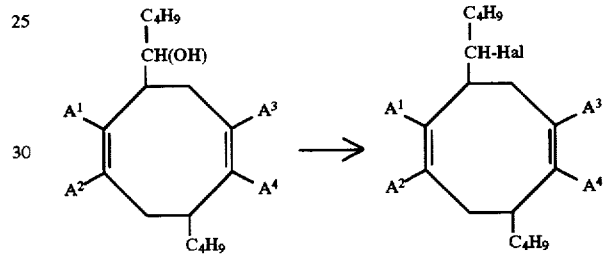

In these formulae, $A^1$, $A^2$, $A^3$ and $A^4$ have the same meanings as defined above; and Hal represents a halogen atom.

2-(2). Sulfonylation of hydroxyl group

Compound A and its equivalent analogs can be reacted with a sulfonylating agent such as methanesulfonyl chloride ($CH_3SO_2Cl$) or ethanesulfonyl chloride ($C_2H_5SO_2Cl$) optionally in the presence of a base such as triethylamine ($Et_3N$), pyridine or potassium carbonate as added thereto to produce sulfonylated derivatives.

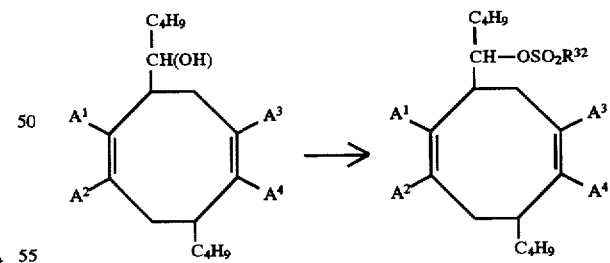

In these formulae, $A^1$, $A^2$, $A^3$ and $A^4$ have the same meanings as defined above, and $R^{32}$ represents a $C_1$–$C_4$ alkyl group.

2-(3). Acylation, carbamoylation and alkoxycarbonylation of hydroxyl group

Compound A and its equivalent analogs can be reacted with acid halides such as acetyl chloride ($CH_3COCl$) or benzoyl chloride (PhCOCl), or acid anhydrides such as acetic anhydride, optionally in the presence of a base such as triethylamine ($Et_3N$), pyridine or potassium carbonate as added thereto to produce acylated derivatives.

Compound A and its equivalent analogs can be reacted with isocyanates such as methyl isocyanate (CH₃NCO) or phenyl isocyanate (PhNCO), or carbamoyl halides such as dimethylaminocarbamoyl chloride ((CH₃)₂NCOCl), optionally in the presence of a base such as triethylamine (Et₃N), pyridine or potassium carbonate as added thereto produce carbamoylated derivatives.

Compound A and its equivalent analogs can be reacted with alkoxycarbonyl halides such as methyl chloroformate (ClCOOCH₃) or ethyl chloroformate (ClCOOC₂H₅), optionally in the presence of a base such as triethylamine (Et₃N), pyridine or potassium carbonate as added thereto to produce alkoxycarbonylated derivatives.

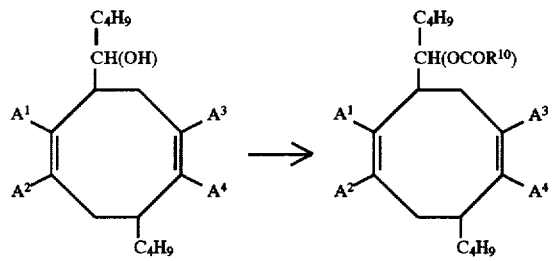

In these formulae, $A^1$, $A^2$, $A^3$, $A^4$ and $R^{10}$ have the same meanings as defined above.

2-(4). Alkylation, alkenylation, alkynylation and aralkylation of hydroxyl group Compound A and its equivalent analogs can be reacted with an alkylating agent such as methyl iodide (CH₃I), ethyl iodide (C₂H₅I) or dimethylsulfate ((CH₃)₂SO₄), an alkenylating agent such as allyl bromide (CH₂=CHCH₂Br), an alkynylating agent such as propargyl chloride (CH≡CCH₂Cl), or an aralkylating agent such as benzyl chloride (PhCH₂Cl) or β-phenylethyl chloride (PhCH₂CH₂Cl) to produce alkylated, alkenylated, alkynylated or aralkylated derivatives.

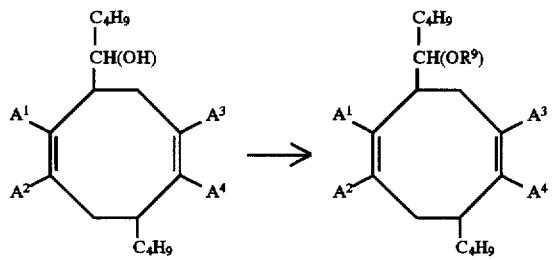

In these formulae, $A^1$, $A^2$, $A^3$, $A^4$ and $R^9$ have the same meanings as defined above.

2-(5). Thiolation of hydroxyl group

The compounds as obtained in 2-(1) or 2-(2) can be reacted with a hydrosulfiding agent such as sodium hydrosulfide (NaSH). The resulting derivatives can be processed in the same manner as in 2-(4) to produce various sulfur-containing derivatives.

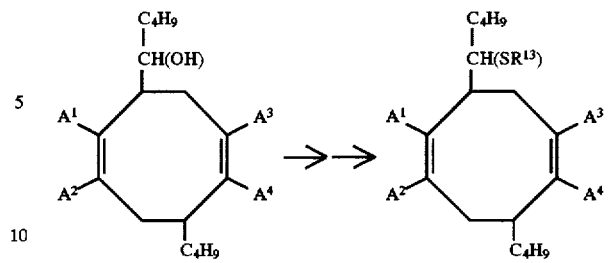

In these formulae, $A^1$, $A^2$, $A^3$, $A^4$ and $R^{13}$ have the same meanings as defined above.

2-(6). Silylation, phosphorylation and alkoxyalkylation of hydroxyl group

Compound A and its equivalent analogs can be reacted with silylated compounds such as trimethylsilyl chloride ((CH₃)₃SiCl), t-butyldimethylsilyl chloride ((t-Bu(CH₃)₂SiCl), optionally in the presence of a base such as triethylamine (Et₃N), pyridine or potassium carbonate to produce silylated derivatives.

Compound A and its equivalent analogs can be reacted with phosphoric esters such as diethylphosphoryl chloride ((EtO)₂POCl) or diphenylphosphoryl chloride ((PhO)₂POCl), optionally in the presence of a base such as triethylamine (Et₃N), pyridine or potassium carbonate to produce phosphorylated derivatives.

Compound A and its equivalent analogs can be reacted with alkoxyalkyl halides such as methoxymethyl chloride (CH₃OCH₂Cl) or ethoxyethyl chloride (C₂H₅OCH₂CH₂Cl) optionally in the presence of a base such as potassium carbonate or sodium hydroxide, or with compounds such as dihydropyran in the presence of an acid catalyst such as p-toluenesulfonic acid (p-TsOH) as added thereto, to produce alkoxyalkylated derivatives.

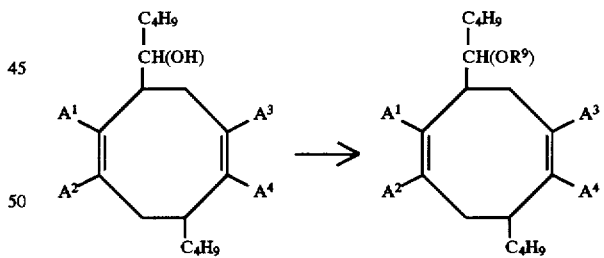

In these formulae, $A^1$, $A^2$, $A^3$, $A^4$ and $R^9$ have the same meanings as defined above.

2-(7). Oxidation of hydroxyl group

Compound A and its equivalent analogs can be oxidized with any ordinary oxidizing agent to produce carbonyl derivatives. Any and every ordinary oxidizing agent capable of oxidizing a secondary hydroxyl group into a carbonyl group can be used. Generally employed herein is oxidation with an inorganic oxidizing agent such as chromic acid and permanganates, an organic oxidizing agent such as DMSO, or oxygen.

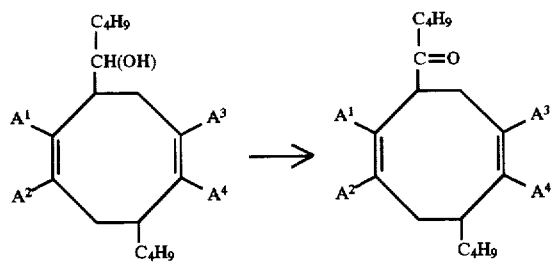

In these formulae, $A^1$, $A^2$, $A^3$ and $A^4$ have the same meanings as defined above.

2-(8). Ketal compounds

The carbonyl compounds as obtained in 2-(7) can be reacted with alcohols such as ethylene glycol, in the presence of an acid catalyst such as p-toluenesulfonic acid (p-TsOH) to produce ketal derivatives.

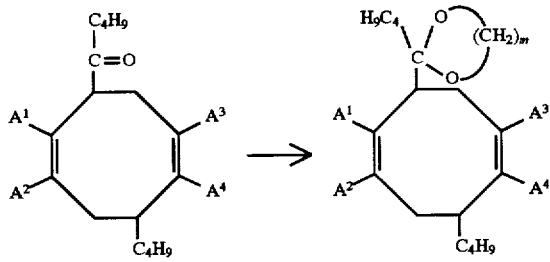

In these formulae, $A^1$, $A^2$, $A^3$, $A^4$ and m have the same meanings as defined above.

2-(9). Oximes, imino compounds

The carbonyl compounds as obtained in 2-(7) can be reacted with amines such as methylamine ($CH_3NH_2$) or aniline ($PhNH2$) under de-watering conditions to produce iminated derivatives. If they are reacted with hydroxyamines under de-watering conditions, oximated derivatives can be produced.

To carry out the reaction under de-watering conditions, the compounds are reacted in an alcohol or in the presence of a molecular sieve in an inert solvent.

The oximes obtained herein can be further processed in the same manner as in the above-mentioned 1-(2) to 1-(4) to produce differently-modified oxime derivatives.

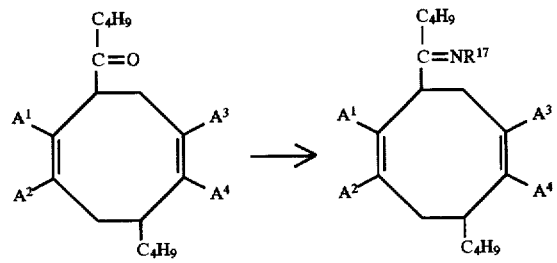

In these formulae, $A^1$, $A^2$, $A^3$, $A^4$ and $R^{17}$ have the same meanings as defined above.

2-(10). Aminated compounds

The compounds as obtained in 2-(1) or 2-(2) can be reacted with amines to produce aminated derivatives.

The amines include, for example, methylamine and dimethylamine.

The oximes obtained in 2-(9) can be reduced through hydrogenation, for example, with a Raney nickel or the like catalyst to produce amine derivatives.

The derivatives obtained herein can be processed in the same manner as in 2-(3) to produce differently-modified amine derivatives.

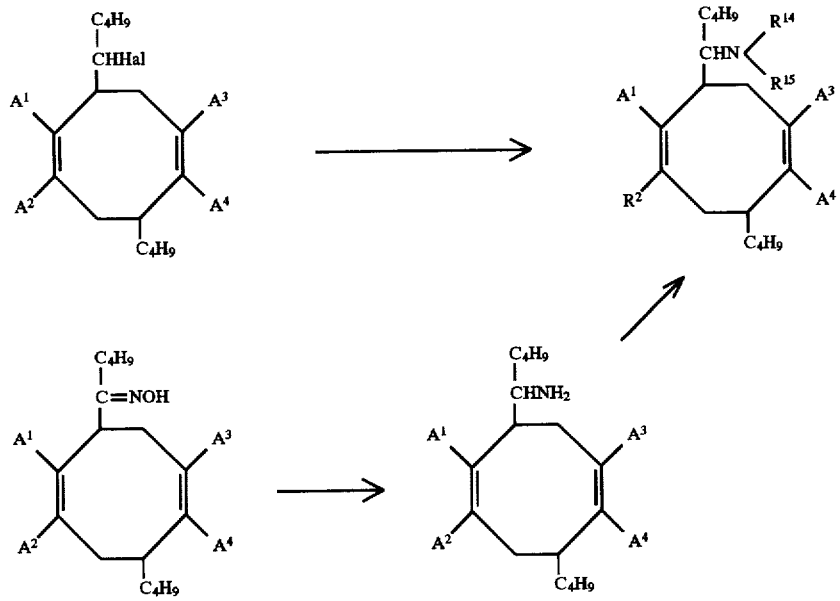

In these formulae, $A^1$, $A^2$, $A^3$, $A^4$, $R^{14}$, $R^{15}$ and Hal have the same meanings as defined above.

2-(11). Hydrogenation of hydroxyl group

The compounds as obtained in 2-(1) can be reduced with a reducing agent such as tributyl tin hydride ($nBu_3SnH$) to produce hydrogenated derivatives.

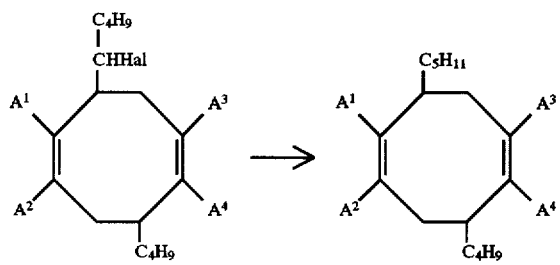

In these formulae, $A^1$, $A^2$, $A^3$, $A^4$ and Hal have the same meanings as defined above.

2-(12). Introduction of double bond

The compounds as obtained in 2-(1) or 2-(2) can be reacted with a base such as DBN, DBU or t-BuOK to thereby introduce a double bond into the compounds through the removal of HHal therefrom. The position into which the double bond is introduced varies, depending on the base used, the type of the solvent used and the reaction temperature. The compounds thus having the double bond as introduced thereinto can be isomerized through reaction with a base.

In these formulae, $A^1$, $A^2$, $A^3$, $A^4$ and Hal have the same meanings as defined above.

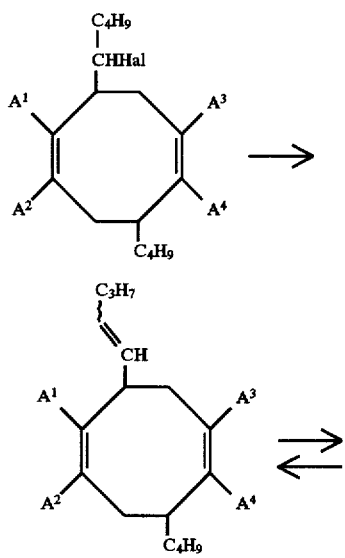

2-(13). Conversion of carbon chain—Part (1)

The compounds as obtained in 2-(12) can be oxidized, for example, through ozonation and then treated with DMS or the like to produce carbonyl derivatives from which the carbon chain has been cleaved at the double bond moiety. The carbonyl compounds obtained herein can be reduced with a reducing agent such as sodium borohydride (NaBH₄) whereby the carbonyl group is converted into a hydroxyl group. The hydroxyl group in the resulting compounds can be modified in the same manner as mentioned hereinabove to give differently-modified derivatives.

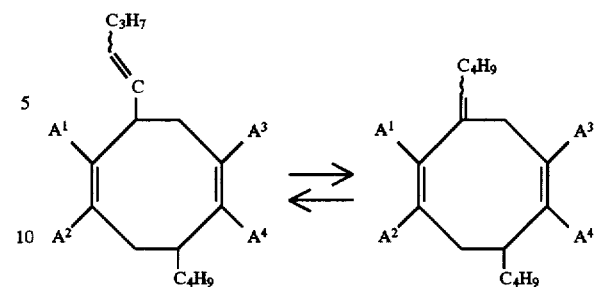

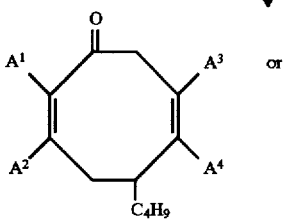

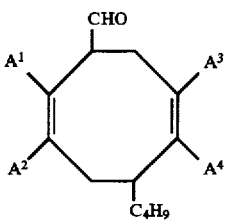

In these formulae, $A^1$, $A^2$, $A^3$ and $A^4$ have the same meanings as defined above.

2-(14). Conversion of carbon chain—Part (2)

The compounds as obtained in 2-(13) can be reacted with an alkyl lithium (RLi) or a Grignard reagent (R—MgHal), or through Reformatsky reaction (with R—Zn—Hal) to thereby introduce different carbon chains into the compounds. The hydroxyl group as produced in the resulting compounds through the reaction can be modified in the same manner as mentioned hereinabove to give differently-modified derivatives.

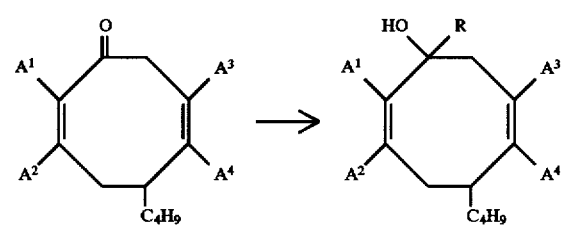

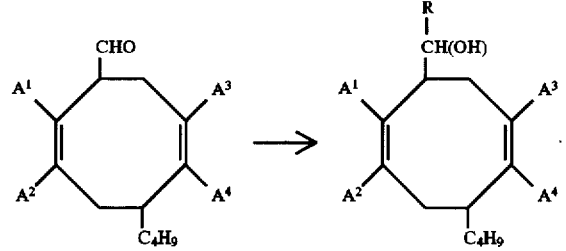

In these formulae, $A^1$, $A^2$, $A^3$ and $A^4$ have the same meanings as defined above; and R has the same meaning as $R^1$.

2-(15). Conversion of carbon chain—Part (3)

The compounds as obtained in 2-(7) can be reacted with R-L (wherein L represents a removable group such as a halogen atom; and R represents an alkyl group, an alkenyl group, an alkynyl group or a haloalkyl group) in the presence of a base such as sodium hydride (NaH) or t-BuOK to thereby introduce different carbon chains into the compounds.

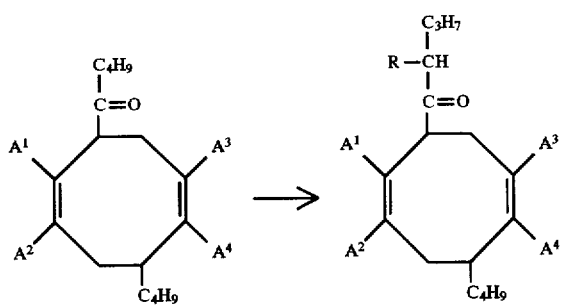

In these formulae, $A^1$, $A^2$, $A^3$ and $A^4$ have the same meanings as defined above.

2-(16). Introduction of oxygen atom—Part (1)

The compounds as obtained in 2-(7) can be reacted with peroxides, such as hydrogen peroxide or m-chloroperbenzoic acid (mCPBA), through Bayer-Villiger reaction to thereby introduce an oxygen atom into the compounds. The resulting compounds can be hydrolyzed to thereby introduce a hydroxyl group thereinto.

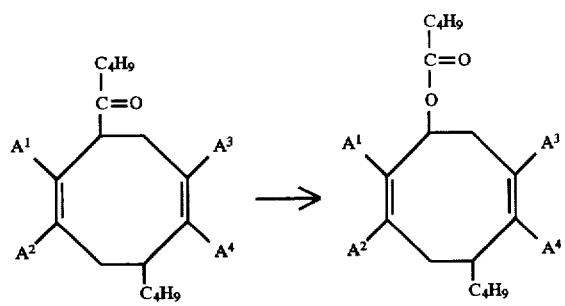

In these formulae, $A^1$, $A^2$, $A^3$ and $A^4$ have the same meanings as mentioned above.

2-(17). Introduction of oxygen atom—Part (2)

The compounds as obtained in 2-(12) can be reacted with peroxides, such as hydrogen peroxide or m-chloroperbenzoic acid (mCPBA), to produce epoxy compounds. The resulting compounds can be reacted alkyl lithium (RLi) compounds such as methyl lithium, or with alkoxide compounds such as sodium methoxide, to thereby introduce an alkyl or alkoxy group into the compounds. The hydroxyl group as produced in the resulting compounds through the reaction can be modified in the same manner as mentioned hereinabove to give differently-modified derivatives.

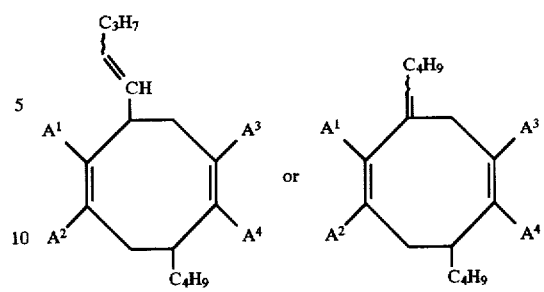

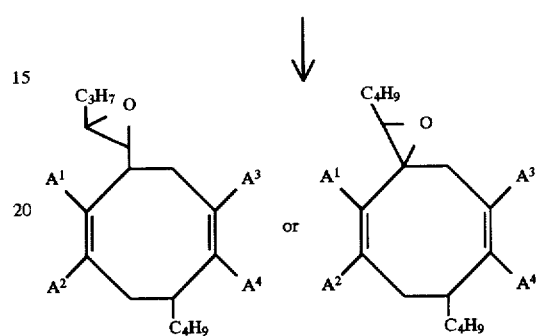

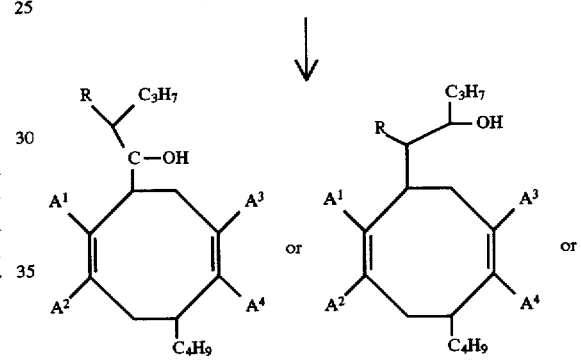

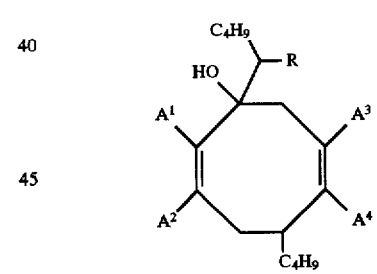

In these formulae, $A^1$, $A^2$, $A^3$ and $A^4$ have the same meanings as defined above; and R has the same meaning as $R^1$.

In addition to the methods mentioned hereinabove, any other ordinary methods capable of being employed in organic synthesis can be naturally employed for differently modifying compound A.

The above-mentioned production methods can be conducted in suitable inert solvents. The solvents employable in these include hydrocarbons such as toluene and xylene; halogenated hydrocarbons such as chlorobenzene and dichloroethane; ethers such as tetrahydrofuran, diisopropyl ether and dioxane; esters such as ethyl acetate; nitriles such as acetonitrile; alcohols such as methyl alcohol and ethyl alcohol; and polar solvents such as dimethylsulfoxide and dimethylformamide.

The reaction temperatures can be freely settled but, in general, should preferably fall between −70° C. and 200° C. or the reflux temperature for the solvent used.

Next, full-synthetic methods for producing the compounds of the present invention are mentioned below.

Production Method 2

A method for producing cyclooctadiene, such as that mentioned below, has been reported in Journal of Chemical Society (B), pp. 1552–1564, 1971; and Journal of Polymer Science: Polymer Chemistry Edition, Vol. 13, pp. 171–187, 1975.

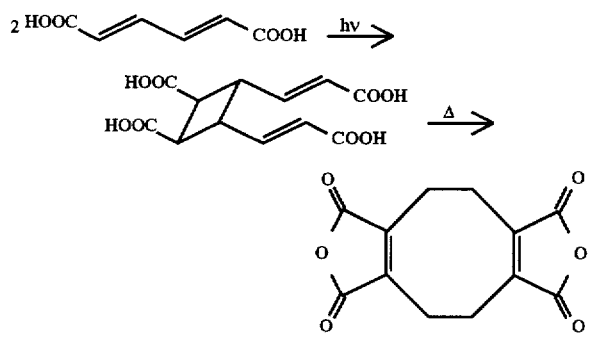

Another method for producing cyclooctadienes, such as that mentioned below, has been reported in Journal of Organic Chemistry, Vol. 42, pp. 2601–2610, 1977.

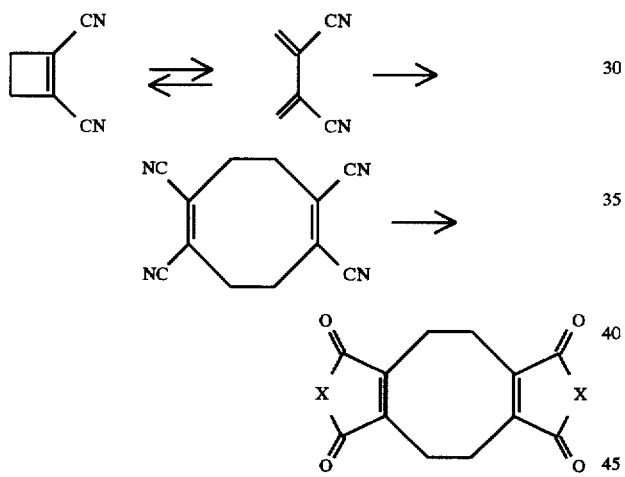

wherein X has the same meaning as defined above.

It is possible to react these cyclooctadienes with a halogenating agent, such as chlorine molecule, bromine molecule or N-bromosuccinimide (NBS), thereby introducing a halogen atom thereinto.

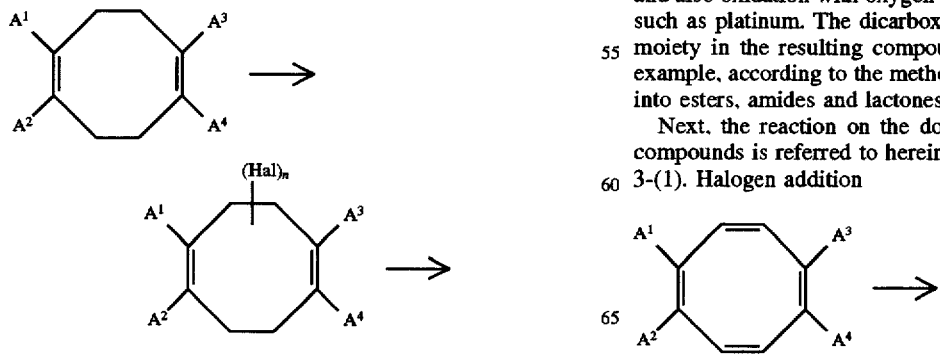

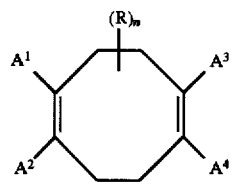

wherein $A^1$, $A^2$, $A^3$, $A^4$ and Hal have the same meanings as defined above; R has the same meaning as $R^1$; and n is an integer of from 1 to 4.

The halogen atom thus introduced into these compounds can be converted into other different substituents in accordance with the methods mentioned hereinabove or with any other ordinary means.

Production Method 3

A process for producing cyclooctadiene, such as that mentioned below, has been reported in Journal of Organic Chemistry, Vol. 58, pp. 2377–2380, 1993.

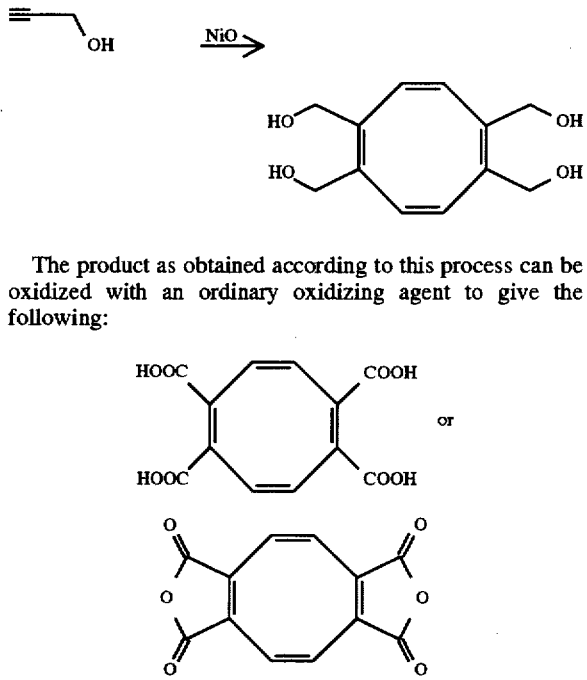

The product as obtained according to this process can be oxidized with an ordinary oxidizing agent to give the following:

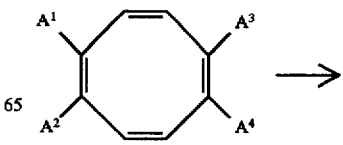

Any ordinary oxidizing agent capable of oxidizing a primary alcohol into a carboxylic acid can be employed for the oxidation. In general, employable are inorganic oxidizing agents such as potassium permanganate and chromic acid and also oxidation with oxygen in the presence of a catalyst such as platinum. The dicarboxylic acid or acid anhydride moiety in the resulting compounds can be converted, for example, according to the methods mentioned hereinabove, into esters, amides and lactones.

Next, the reaction on the double bond moiety in these compounds is referred to hereinunder.

3-(1). Halogen addition

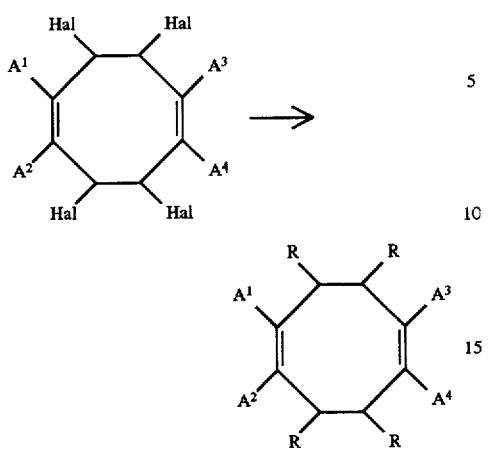

wherein $A^1$, $A^2$, $A^3$, $A^4$ and Hal have the same meanings as defined above; R has the same meaning as $R^1$.

Halogen molecules, such as bromine, can be added to the compounds as obtained in the above, whereby halogen atoms can be introduced thereinto. The resulting halogenated compounds can be processed in the same manner as mentioned hereinabove to thereby introduce different substituents, such as an alkyl group, into the compounds.

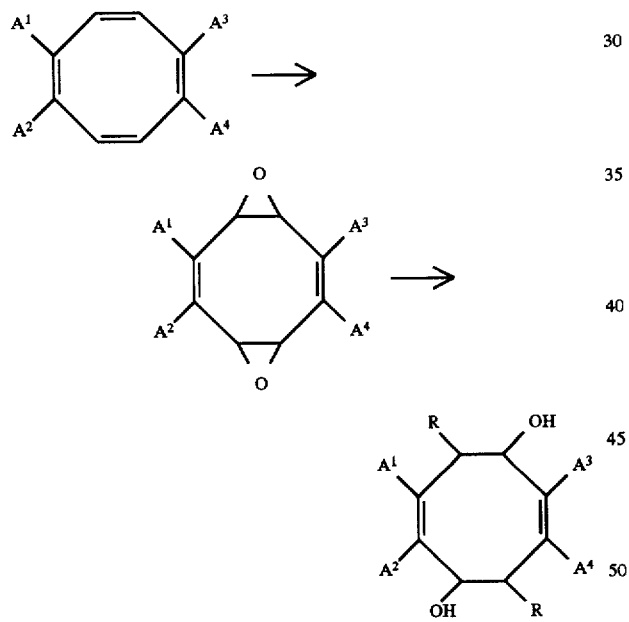

wherein $A^1$, $A^2$, $A^3$ and $A^4$ and Hal have the same meanings as defined above; and R has the same meaning as $R^1$.

The compounds as obtained in the above can be reacted with peroxides such as hydrogen peroxide or m-chloroperbenzoic acid (mCPBA) to produce epoxy compounds. The resulting epoxy compounds can be reacted with alkyl lithium compounds (RLi) such as methyl lithium, to thereby introduce an alkyl group thereinto. The hydroxyl group as produced in the resulting compounds can be modified, according to various methods such as those mentioned hereinabove, into different substituents.

In addition to the methods of 3-(1) and 3-(2), it is naturally possible to modify the double bond in the compounds according to any ordinary methods generally employed in organic synthesis to give differently-modified derivatives.

Production Method 4

A method for producing 9-membered cyclic compounds (nonanolides) has been reported in Journal of the American Chemical Society, Vol. 94, pp. 4735–4737, 1972.

Referring to this method, one can produce the compounds of the present invention according to the following reaction route.

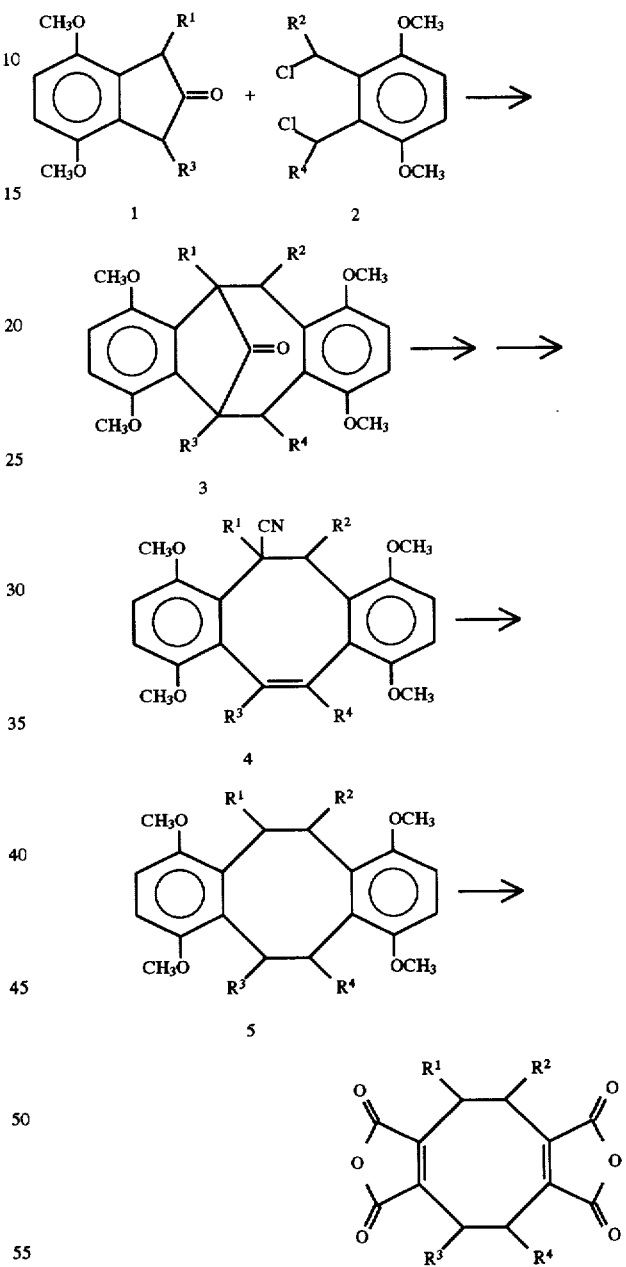

wherein $R^1$, $R^2$, $R^3$ and $R^4$ have the same meanings as defined above.

Briefly, intermediates 1 and 2 are reacted in the presence of a base such as sodium hydride (NaH) or t-BuOK, to give an intermediate 3. The intermediate 3 is reacted with hydroxylamine to give an oxime derivative, which may then be subjected to rearrangement, for example, through reaction with phosphorus oxychloride or the like to thereby construct a 8-membered ring structure (intermediate 4).

The cyano group of the intermediate 4 is removed, for example, through hydrolysis and decarboxylation, or is reacted with an alkyl lithium (R—Li) or the like to thereby introduce an alkyl group into the intermediate 4, and thereafter the double bond is reduced, for example, through hydrogenation to produce a compound 5.

The compound 5 is then reacted with $BBr_3$ to remove the tetramethyl ether moiety therefrom, thereby giving a hydroquinone derivative, which is thereafter oxidized with potassium permanganate or the like and then reacted with lead tetraacetate or the like to produce the intended product. The product can also be produced through oxidation with ozonation.

Starting from an intermediate 3', it is also possible to obtain the compounds of the present invention in accordance with the following reaction route.

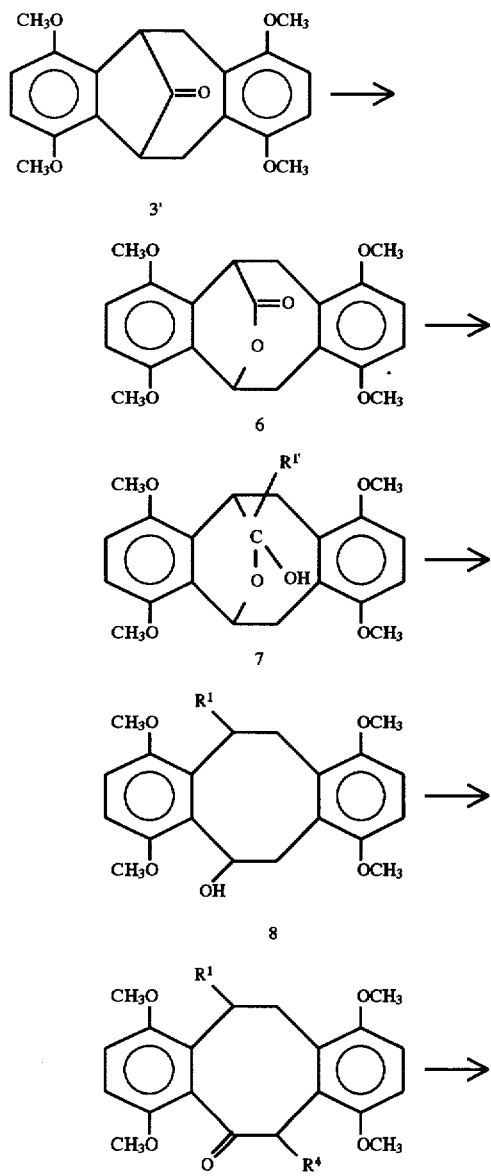

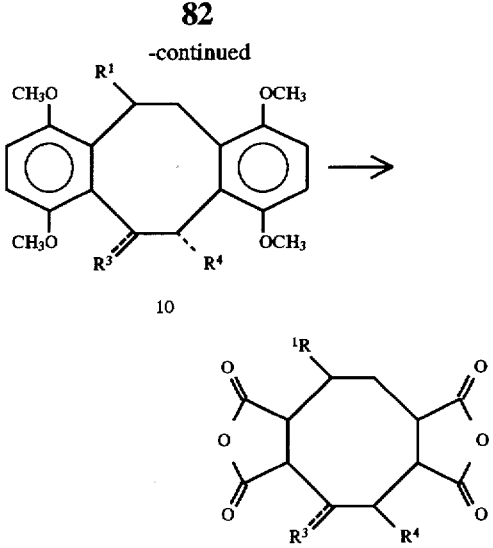

Briefly, an intermediate 3' is reacted with a peroxide, such as hydrogen peroxide or m-chloro-perbenzoic acid (m-CPBA) through Bayer-Villiger reaction to give a lactone derivative 6, which is then reacted with a Grignard reagent or an alkyl lithium reagent to give a compound 7. Next, the compound 7 is reacted with a reducing agent such as lithium aluminium hydride ($LiAlH_4$) to produce a compound 8. The compound 8 is oxidized and then reacted with $R^4$—Hal in the presence of a base such as sodium hydride to give a compound 9. The carbonyl group of the resulting intermediate 9 is processed through Wittig reaction or the like to thereby introduce a carbon chain into the compound, or is treated with a reducing agent such as a Raney nickel to obtain a compound 10. Then, the compound 10 is processed in the same manner as above to produce the intended product.

Production Method 5

Another method for producing 9-membered cyclic compounds (nonanolides) has been reported in Journal of the American Chemical Society, Vol. 114, pp. 9673-9674, 1992.

Referring to this method, one can produce the compounds of the present invention according to the following reaction route.

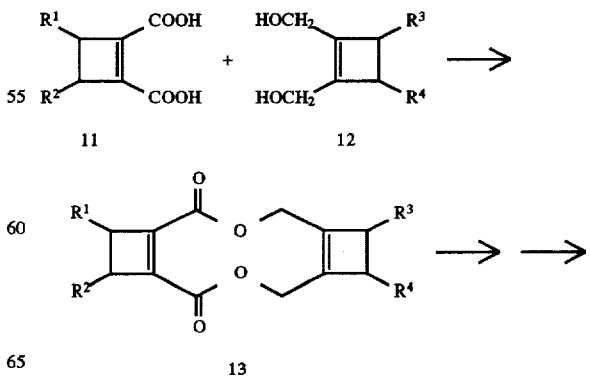

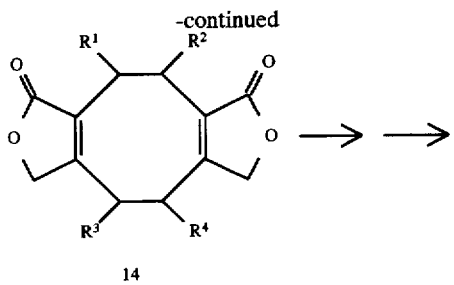

14

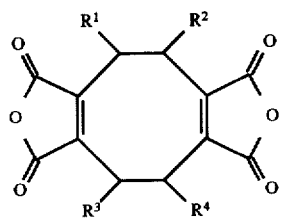

wherein $R^1$, $R^2$, $R^3$ and $R^4$ have the same meanings as defined above.

Briefly, intermediates 11 and 12 are reacted in the presence of a condensing agent such as DCC to give an intermediate 13. The intermediate 13 is subjected to photoreaction and then heated to give a compound 14. The lactone moiety in the compound 14 is hydrolyzed and then oxidized with potassium permanganate or the like to obtain the intended product.

The compounds of the present invention which can be produced in accordance with these production methods 1 to 5 encompass several stereoisomers and optical isomers, which shall naturally be within the scope of the present invention.

The compounds of the present invention thus Produced in the manner as mentioned hereinabove are active against various types of mold and are therefore useful as antimolds in medical use, antimolds for animals, fungicides in agricultural use, antimolds for foods, antimolds in industrial use, and even in antithrombocytic agents.

Concretely, the compounds of the present invention are active against various phytopathogenic fungi that will do serious harm in agriculture, such as Damping-off, Pythium (*Pythium debaryanum*), Late blight (*Phytophthora infestans*), Sclerotinia rot (*Sclerotinia sclerotiorum*), Brown rot (*Sclerotinia cinerea*), Scab (*Venturia inaequalis*), Glume blotch (*Septoria nodorum*), Melanose (*Diaporthe citra*), Net blotch (*Pyrenophora teres*), Gray mold (*Botrytis cinerea*), Blast (*Pyricularia oryzae*), Anthracnose (*Colletotrichum lagenarium*), Eyespot (*Pseudocercosporella herpotrichoides*), Leaf blotch (*Rhynchosporium secalis*), Alternaria leaf spot (*Alternaria mali*), Fusarium wilt (*Fusarium oxysporum*), Sheath blight (*Rhizoctonia solani*) and Damping-off, Rhizoctonia (*Rhizoctonia solani*); and also against various microorganisms that will do serious harm in medicine and industry, such as *Aspergillus nigar*, *Aspergillus fumigatus*, *Trichophyton mentagrophytes*, *Trichophyton rubrum*, *Penicillium citrinum*, *Candida albicans* and *Saccharomyces cerevisiae*.

In addition, as exhibiting an antithrombocytoagglutinative activity, the compounds of the present invention can be used in antithrombocytic agents for curing and preventing various thrombotic disorders, such as cerebral thrombosis, pulmonary thrombosis, myocardial infarction, stenocardia and peripheroarterial obstruction.

Where the compounds of the present invention are used in agrohorticultural fungicides, any carriers that do not detract from the activity of the compounds can be used. Generally usable are solid carriers, such as clay, talc, bentonite and diatomaceous earth, which can be combined with any of suitable liquid carriers, such as water, alcohols (e.g., methanol, ethanol), aromatic hydrocarbons benzene, toluene, xylene), chlorinated hydrocarbons, ethers, ketones, esters (e.g., ethyl acetate) and acid amides (e.g., dimethylformamide). If desired, any of emulsifiers, dispersing agents, suspending agents, penetrants, excipients and stabilizers can be added to the compounds along with the carriers and formulated into any preparations of liquid solutions, oil solutions, emulsifiable concentrates, wettable powders, dusts, granules and flowables for practical use.

The dose of the preparation comprising the compound of the present invention varies, depending on the site to which it is applied, the time when it is applied, the method how it is applied, the disease against which it is applied and the crop for which it is applied, but may be generally from 5 g/ha to 50 kg/ha in terms of the active ingredient or the compound of the invention in the preparation.

If desired, the preparation may be combined with any of various herbicides, fungicides, insecticides, plant growth regulating agents, agonists and fertilizers, while it is formulated or sprayed.

On the other hand, where the compounds of the present invention are used in antimolds in medical use, for example, they can be formulated into liquid liniments, gels or ointments, which can be applied to the affected parts to cure them.

Where the compounds of the present invention are used in antithrombocytic agents, the agents can be formulated for parenteral administration, for example, into injections (for intravenous, intramuscular and intraabdominal administration), ointments, suppositories and aerosols, or for peroral administration, for example, into tablets, capsules, granules, pills, syrups, liquid preparations, emulsions and suspensions.

The above-mentioned pharmaceutical compositions comprising the compound of the present invention contains the compound in an amount of approximately from 0.1 to 99.5% by weight, preferably approximately from 0.5 to 95% by weight, relative to the total weight of the composition.

The compounds of the present invention and the pharmaceutical compositions comprising the compound may additionally contain any other pharmaceutically-active compounds. The pharmaceutical composition may contain a plurality of the compounds of the invention as combined.

The clinical dose of the compound of the present invention varies, depending on the age, the body weight, the sensitivity and the condition of the patient to which it applied, but the effective dose thereof shall be from 0.003 to 1.5 g/day/adult or so, preferably from 0.01 to 0.6 g/day/adult or so. If desired, however, any dose overstepping the above-mentioned range is also applicable.

The compounds of the present invention can be formulated into pharmaceutical preparations for clinical administration according to conventional means.

For example, they can be formulated into tablets, capsules, granules and pills for peroral administration along with vehicles such as white sugar, lactose, glucose, starch and mannitol; binders such as hydroxypropyl cellulose, syrup, arabic gum, gelatin, sorbitol, tragacanth, methyl cellulose and polyvinyl pyrrolidone; disintegrators such as starch, carboxymethyl cellulose and its calcium salt, microcrystalline cellulose and polyethylene glycol; and lubricants such as talc, magnesium or calcium stearate, silica, sodium laurate and glycerol.

They can also be formulated into injections, liquid preparations, emulsifiable concentrates, suspensions, syrups and aerosols along with solvents for the active ingredient, such as water, ethyl alcohol, isopropyl alcohol, propylene glycol, 1,3-butylene glycol and polyethylene glycol, surfactants such as sorbitan fatty acid esters, polyoxyethylene sorbitan fatty acid esters, polyoxyethylene fatty acid esters, polyoxyethylene ether of hydrogenated castor oil and lecithin; suspending agents such as cellulose derivatives (e.g., sodium carboxymethyl cellulose, methyl cellulose) and natural rubbers (e.g., tragacanth, arabic gum); preservatives such as paraoxybenzoates, benzalkonium chloride and sorbates.

To formulate endermic ointments comprising the compound of the present invention, for example, employable are white petrolatum, liquid paraffin, higher alcohols, Macrogol ointment bases, hydrophilic ointment bases and aqueous gel bases.

Suppositories comprising the compound of the present invention can be formulated along with cacao butter, polyethylene glycol, lanolin, fatty acid triglycerides, coconut oil and polysorbates.

BEST MODES OF CARRYING OUT THE INVENTION

The present invention is described in more detail by means of the following examples, which, however, are not whatsoever intended to restrict the scope of the invention.

Reference Example 1

*Zopfiella curvata* No. 37-3 strain was cultured at 25° C. for 5 days in a liquid culture medium (pH 7.0) containing PD (potato dextrose, product of Difco Co.) as the seed culture, and the resulting culture solution was inoculated into a fermentation culture medium, i.e., a medium (pH 7.0) prepared by adding 0.1% polypeptone, 0.1% yeast extract and 10% (v/v %) tomato juice (containing salt, product of Kagome Inc.) to a PD (potato dextrose) culture medium (product of Difco Co.), and the mixture was subjected to rotatory culturing (140 rpm) at 25° C. for 12 days.

The resulting culture solution was filtered to remove the cells, and then the filtrate from the culture was adjusted to pH 3 using 2N hydrochloric acid. To 1.5 liters of the filtrate was added ethyl acetate for extraction, to obtain an ethyl acetate-extracted fraction. The ethyl acetate-extracted fraction was concentrated under reduced pressure, and the solvent was removed, after which the precipitate was dissolved in a small amount of benzene:ethyl acetate:acetic acid (80:1:2), charged into a silica gel column which had been previously equilibrated with the same type of solvent, and then eluted by the same type of solvent. The active fractions were concentrated and, after the solvent was removed, the solution was applied to a Sephadex LH-20 column chromatography which had been previously equilibrated with benzene and eluted by benzene:acetic acid (40:1) to obtain fractions containing the compounds A and B, respectively.

After the fraction containing the compound A was concentrated, a single peak portion was collected by conducting HPLC under the conditions of a device: Shimazu LC-5A manufactured by Shimazu Manufacturing Co., Ltd. in Japan; column: Inertsil ODS-2 φ 4.6 mm×250 mm (manufactured by GL Sciences, Ltd.); developing solvent: acetonitrile-water (80:20, v/v %.), flow rate: 1.0 ml/min.; temperature: 25° C.; and determination: UV 254 nm. to obtain about 40 mg of the compound A. The activities of the compounds in the culture and in the crude fractions was determined by the paper disk method using *Botrytis cinerea*.

The Rf value: Silica gel thin-layer chromatography (Keisel gel 60F$_{254}$, Merck Co.) 0.35 in a solvent system of benzene:ethyl acetate:acetic acid (80:1:2, v/v %)

Production Example 1

Synthesis of 3-(1-acetoxypentyl)-7-butyl-1,5-cyclooctadiene-1,2,5,6-tetracarboxylic acid di-anhydride (Compound No. 1 of the invention)

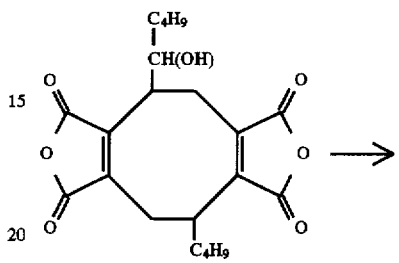

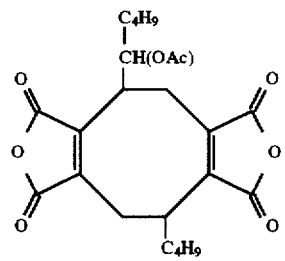

11.5 mg of Compound A was dissolved in 2 ml of dichloromethane and cooled to from 0 to 5° C. 10 mg of pyridine was added to the resulting solution. After 5 minutes, 10 mg of acetyl chloride was added thereto. Then, the solution was stirred for 15 hours at room temperature. 2 ml of chloroform and 2 ml of water were added to the solution, and the organic layer was extracted out. The organic layer was washed with 2 ml of 1-N hydrochloric acid and 2 ml of aqueous, saturated sodium hydrogencarbonate solution in that order, and then dried with anhydrous sodium sulfate. The solvent was removed through distillation under reduced pressure to obtain 11 mg of the intended product as oil.

Production Example 2

Synthesis of 7-butyl-3-(1-methanesulfonyloxypentyl)-1,5-cyclooctadiene-1,2,5,6-tetracarboxylic acid di-anhydride (Compound No. 2 of the invention)

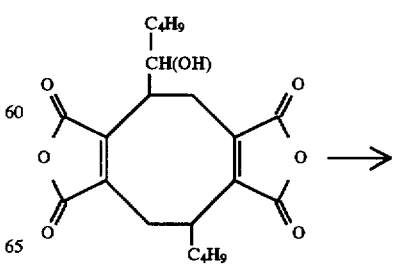

-continued

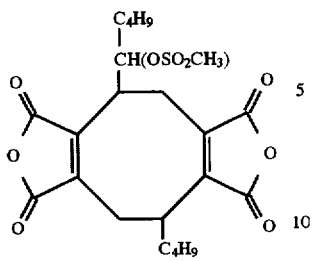

9 mg of Compound A was dissolved in 1 ml of dichloromethane and cooled to from 0 to 5° C. 4 mg of triethylamine was added to the resulting solution, and then 5 mg of methane sulfonyl chloride was added thereto. Then, the solution was stirred for 15 hours at room temperature. 2 ml of chloroform and 2 ml of water were added to the solution, and the organic layer was extracted out. The organic layer was washed with 1 ml of 1-N hydrochloric acid and 1 ml of aqueous, saturated sodium hydrogencarbonate solution in that order, and then dried with anhydrous sodium sulfate. The solvent was removed through distillation under reduced pressure, and 10 mg of a crude product was obtained. Thus obtained crude product was purified through silica gel column chromatography (using an eluent of chloroform) to obtain 7 mg of the intended product as oil.

In the same manner as in Production Examples 1 and 2, Compound No. 3 to Compound No. 5 of the invention were synthesized.

7-Butyl-3-(1-trimethylsilyloxypentyl)-1,5-cyclooctadiene-1,2,5,6-tetracarboxylic acid di-anhydride (Compound No. 3 of the invention):

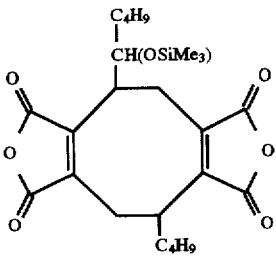

7-Butyl-3-(1-diphenylphosphoryloxypentyl)-1,5-cyclooctadiene-1,2,5,6-tetracarboxylic acid di-anhydride (Compound No. 4 of the invention):

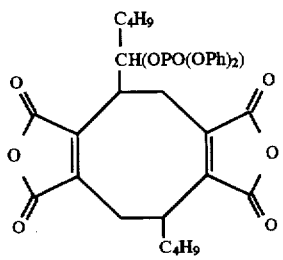

-continued

7-Butyl-3-(1-(4-chlorophenylcarbamoyloxy)pentyl)-1,5-cyclooctadiene-1,2,5,6-tetracarboxylic acid di-anhydride (Compound No. 5 of the invention):

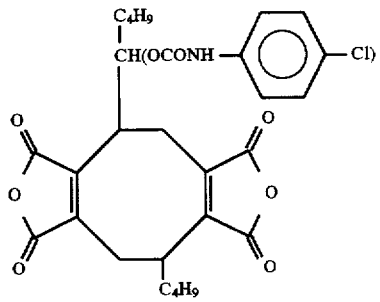

Production Example 3

Synthesis of 7-butyl-3-(1-fluoropentyl)-1,5-cyclooctadiene-1,2,5,6-tetracarboxylic acid di-anhydride (Compound No. 6 of the invention)

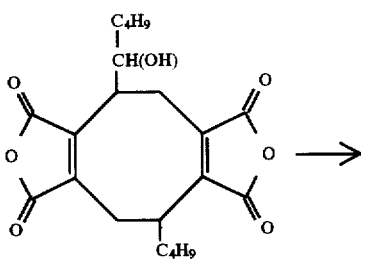

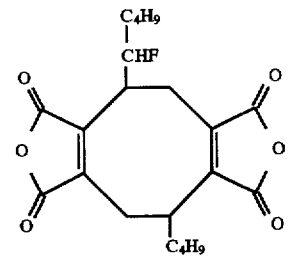

0.034 ml (0.257 mmol) of DAST was dropwise added to 1 ml of a solution of 20 mg (0.051 mmol) of Compound A in dry dichloromethane at −78° C. under the atmosphere of nitrogen. The solution was cooled to 0° C. over a period of 1 hour, while stirring, and 0.2 ml of methanol was added thereto. The solution was extracted with 1 ml of dichloromethane and then washed with water. The organic layer was dried with anhydrous magnesium sulfate and then filtered. The resulting filtrate was concentrated under reduced pressure to obtain a crude product. Thus obtained crude product was purified through partitioning thin-layer chromatography (using an eluent of benzene/acetic acid= 40:1) to obtain 7 mg of the intended product as oil.

Production Example 4

Synthesis of 7-butyl-3-(1-chloropentyl)-1,5-cyclooctadiene-1,2,5,6-tetracarboxylic acid di-anhydride (Compound No. 7 of the invention)

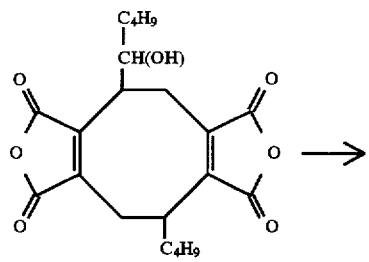

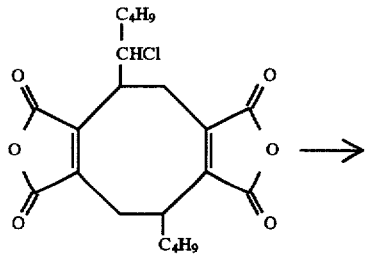

15 mg (0.038 mmol) of Compound A and 210 mg (0.80 mmol) of triphenylphosphine were dissolved in 20 ml of dry carbon tetrachloride and heated under reflux for 2 hours. The solution was cooled to room temperature and then washed with aqueous, saturated sodium hydrogencarbonate solution.

The organic layer was dried with anhydrous sodium sulfate, and the solvent was removed therefrom through distillation under reduced pressure. The resulting residue was passed two times through a short, silica gel column (using an eluent of diethyl ether). The thus obtained crude product was then purified through high-performance liquid chromatography (column: Inertsil ODS-2, eluent: acetonitrile/water=4:1) to obtain 10.6 mg of the intended product as oil.

Production Example 5

Synthesis of 7-butyl-3-(1-pentenyl)-1,5-cyclooctadiene-1,2,5,6-tetracarboxylic acid di-anhydride (Compound No. 8 of the invention)

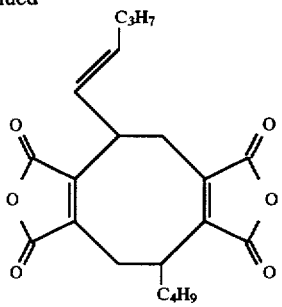

50 mg (0.44 mmol) of t-BuOK was added all at a time to 10 ml of a solution of 17.4 mg (0.045 mmol) of Compound No. 7 in tetrahydrofuran at 0° C., and then gradually heated up to room temperature. After 2 hours, 200 mg (5.0 mmol) of sodium hydroxide and 5 ml of methanol were added thereto and stirred for 30 minutes at room temperature. After the reaction, the solvent was removed through distillation under reduced pressure, and the resulting residue was made acidic by adding hydrochloric acid thereto, and then extracted with 20 ml of ethyl acetate. The resulting extract was dried with anhydrous sodium sulfate, and the solvent was removed therefrom through distillation under reduced pressure. The residue was then purified through high-performance liquid chromatography (column: Inertsil ODS-2, eluent: acetonitrile/water=4:1) to obtain 4 mg of the intended product as oil.

Production Example 6

Synthesis of 7-butyl-3-pentylidene-1,5-cyclooctadiene-1,2,5,6-tetracarboxylic acid di-anhydride (Compound No. 9 of the invention)

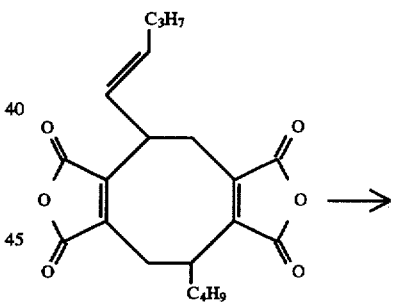

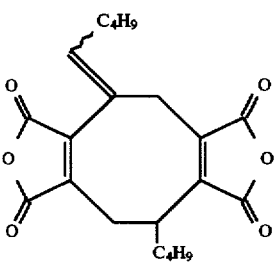

One drop of diazabicycloundecene (DBU) was added to 5 ml of a solution of 38.6 mg (0.95 mmol) of Compound No. 8 in benzene, and heated under reflux for 2 hours. After the solution was cooled to room temperature, 200 mg (5.0 mmol) of sodium hydroxide and 5 ml of methanol were added thereto and stirred for 30 minutes. The solvent was removed through distillation under reduced pressure, and the residue was made acidic by adding hydrochloric acid thereto, and then extracted with 20 ml of ethyl acetate. The extract was dried with anhydrous sodium sulfate, and the solvent was removed therefrom through distillation under reduced pressure. The residue was then purified through high-performance liquid chromatography (column: Inertsil-2, eluent: acetonitrile/water=4:1) to obtain 20 mg of the intended product as oil.

Production Example 7

Synthesis of 7-butyl-3-pentanoyl-1,5-cyclooctadiene-1,2,5,6-tetracarboxylic acid di-anhydride (Compound No. 10 of the invention)

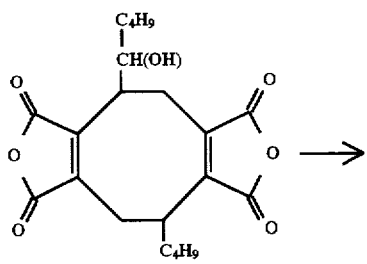

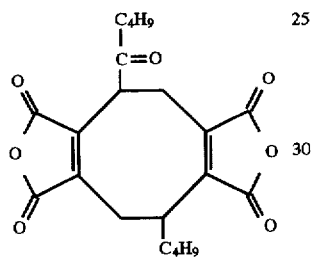

7 mg of Compound A was dissolved in 3 ml of dichloromethane, and 1 mg of sodium acetate was added thereto. Next, 8 mg of pyridinium chlorochromate (PCC) was added to the resulting solution at room temperature and then stirred for 2 hours. 2 ml of diethyl ether was added to this solution, and the insoluble solids were removed through filtration with Celite. The solvent was removed through distillation under reduced pressure, and 7 mg of a crude product was obtained. Thus obtained crude product was purified through silica gel column chromatography (eluent: diethyl ether/dichloromethane=1:1) to obtain 4 mg of the intended product as a white crystal.

melting point: from 203.0° to 204.0° C.

Production Example 8

Synthesis of 7-butyl-3-(2-butyl-1,3-dioxolane-2-yl)-1,5-cyclooctadiene-1,2,5,6-tetracarboxylic acid di-anhydride (Compound No. 11 of the invention)

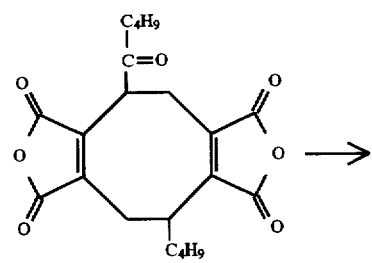

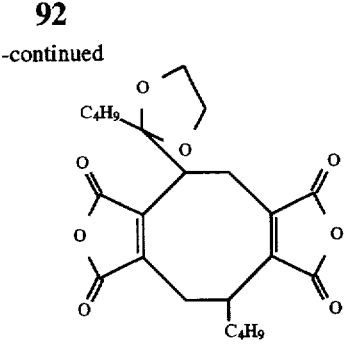

50 mg (0.81 mmol) of ethylene glycol and 5 mg (0.026 mmol) of p-toluenesulfonic acid were added to 30 ml of a solution of 30 mg (0.077 mmol) of Compound No. 10 in toluene, and heated under reflux for 15 hours while de-watering with Dean-Stark. The solvent was removed from the reaction mixture through distillation under reduced pressure, and a crude product was obtained. Thus obtained crude product was purified through high-performance liquid chromatography (column: Inertsil ODS-2, eluent: acetonitrile/water=4:1) to obtain 9 mg of the intended product as oil.

Production Example 9

Synthesis of 7-butyl-3-(1-(tetrahydropyran-2-yloxy) pentyl)-1,5-cyclooctadiene-1,2,5,6-tetracarboxylic acid di-anhydride (Compound No. 12 (epimer 1) of the invention and Compound No. 13 (epimer 2) of the invention)

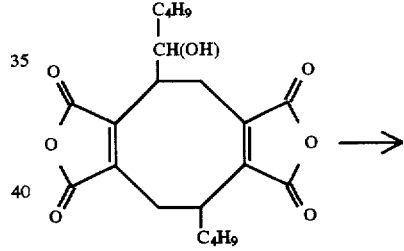

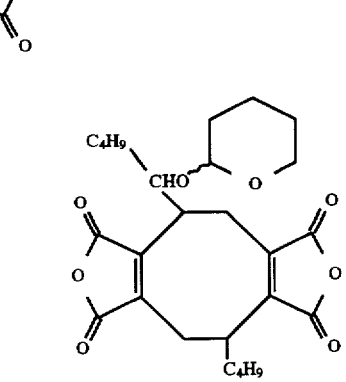

20 mg (0.051 mmol) of Compound A was dissolved in 0.5 ml of dichloromethane, 2 mg (0.012 mmol) of p-toluenesulfonic acid was added thereto, and 0.01 ml (0.11 mmol) of dihydropyran was added thereto at 0° C. Then, the solution was stirred for 30 minutes. One ml of aqueous, saturated sodium hydrogencarbonate solution was added to the solution, which was then extracted two times with 5 ml of dichloromethane. The organic layer was dried with anhydrous magnesium sulfate, and filtered, and the resulting filtrate was concentrated under reduced pressure to obtain a crude product. Thus obtained crude product was purified through high-performance liquid chromatography (column:

Inertsil ODS-2, eluent: acetonitrile/water=4:1) to obtain 6 mg of epimer 1 (polar, oily substance) and 5 mg of epimer 2 (low-polar, crystal).

Production Example 10

Synthesis of 7-butyl-3-(1-hydroxypentyl)-1,5-cyclooctadiene-1,2,5,6-tetracarboxylic acid N,N'-dimethyldiimide (Compound No. 14 of the invention)

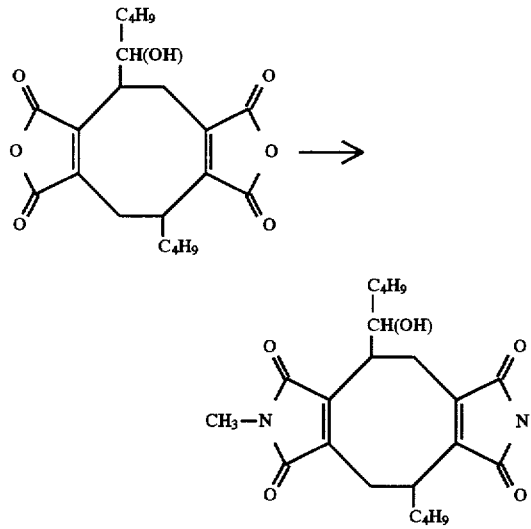

8 mg (0.064 mmol) of aqueous, 25-% methylamine solution was added to 0.5 ml of a solution of 10 mg (0.026 mmol) of Compound A in acetic acid, stirred for 15 hours at room temperature, and then heated under reflux for 8 hours. The solvent was removed through distillation under reduced pressure to obtain a crude product. Thus obtained crude product was purified through silica gel column chromatography (eluent: hexane/ethyl acetate=1:1) to obtain 10 mg of the intended product as oil.

In the same manner as in Procution Example 10, Compound No. 15 to Compound No. 17 of the present invention were synthesized.

7-Butyl-3-(1-hydroxypentyl)-1, 5-cyclooctadiene-1, 2, 5, 6-tetracarboxylic acid diimide
(Compound No. 15 of the invention):

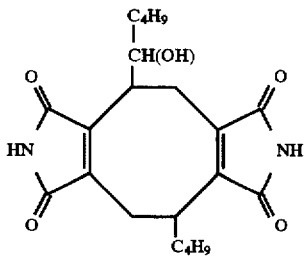

7-Butyl-3-(1-hydroxypentyl)-1, 5-cyclooctadiene-1, 2, 5, 6,-tetracarboxylic acid-N, N'-dibenzyldiimide
(Compound No. 16 of the invention):

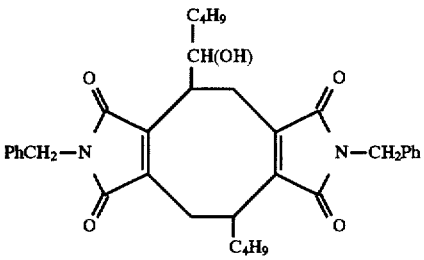

7-Butyl-3-pentanoyl-1, 5-cyclooctadiene-1, 2, 5, 6-tetracarboxylic acid diimide
(Compound No. 17 of the invention):

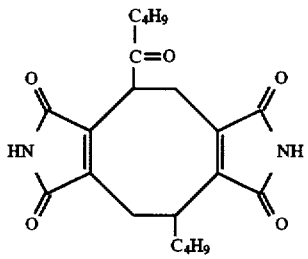

Production Example 11

Synthesis of Compound No. 18 of the invention

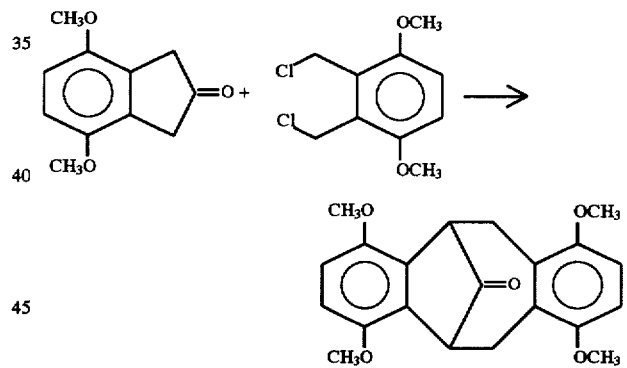

20 ml of a solution of 2.2 g of 1,4-dimethoxy-2,3-bis (chloromethyl)benzene in tetrahydrofuran (THF) was dropwise added to a suspension that had been prepared by suspending 5.4 g of 35-% potassium hydride in 50 ml of THF, at from 0° to 5° C. After the solution was stirred for 10 minutes, 20 ml of a solution of 1.8 g of 4,7-dimethoxyindan-2-one in THF was dropwise added thereto at from 0° to 5° C. Next, the solution was stirred for 4 hours at room temperature. The resulting solution was poured into water with ice and then concentrated under reduced pressure. The solution was made neutral by adding 2-N hydrochloric acid thereto, and then extracted two times with 80 ml of chloroform. The resulting organic layer was dried with anhydrous magnesium sulfate, and the solvent was removed therefrom through distillation under reduced pressure to obtain 6.4 g of a crude product. Thus obtained crude product was purified through silica gel column chromatography, and 2.4 g of a crude crystalline product was obtained. Thus obtained crude

Production Example 12

Synthesis of Compound No. 19 of the invention

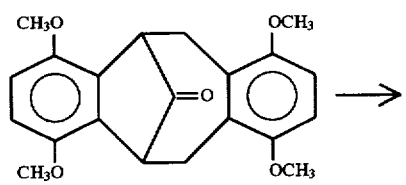

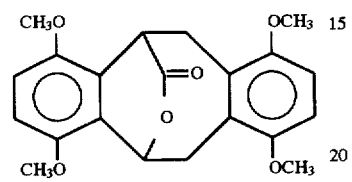

2 g of Compound No. 18 was dissolved in 80 ml of dichloromethane, and 4 g of sodium hydrogencarbonate and 1.34 g of m-chloro-perbenzoic acid (m-CPBA) were added to the resulting solution in that order at room temperature, and then stirred for 15 hours. The solution was extracted with 80 ml of chloroform and 80 ml of water added thereto. The resulting organic layer was washed with an aqueous sodium hydrogencarbonate solution, and then dried with anhydrous magnesium sulfate. The solvent was removed through distillation under reduced pressure to obtain 2.1 g of a crude, crystalline product. Thus obtained crude, crystalline product was washed with 10 ml of diethyl ether, filtered and dried to obtain 1.6 g of the intended product.

melting point: from 184.0° to 186.0° C.

Production Example 13

Synthesis of Compound No. 20 of the invention

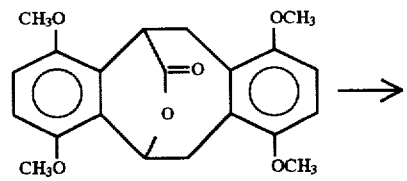

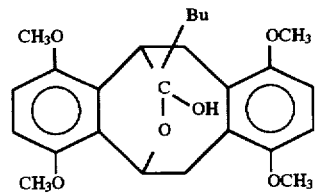

100 mg of Compound No. 19 was dissolved in 20 ml of dry THF, and 1.5 ml of a solution of 1.9M of butyl magnesium chloride in THF was dropwise added to the resulting solution at room temperature and then stirred for 10 minutes. The solution was poured into water, and 2-N hydrochloric acid was added thereto. The solution was then extracted with 50 ml of diethyl ether. The resulting organic layer was dried with anhydrous magnesium sulfate, and the solvent was removed therefrom through distillation under reduced pressure to obtain 110 mg of the intended product as oil.

Production Example 14

Synthesis of Compound No. 21 of the invention

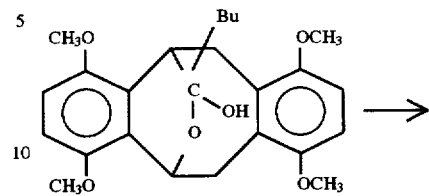

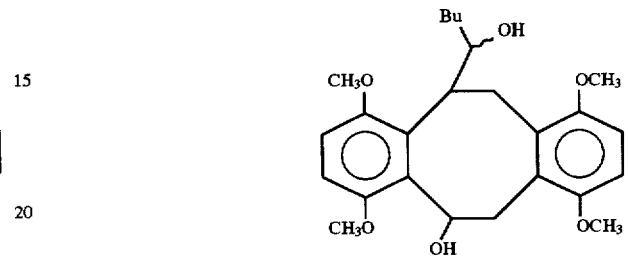

100 mg of Compound No. 20 was dissolved in 20 ml of dry THF. 10 mg of lithium aluminium hydride (LiAlH4) was added to the resulting solution at from 0° to 5° C. and then stirred at room temperature for 1 hour. Water and 2-N hydrochloric acid were added to the solution, which was then extracted with 40 ml of diethyl ether. The resulting organic layer was dried with anhydrous magnesium sulfate, and the solvent was removed therefrom through distillation under reduced pressure to obtain 90 mg of a crude, crystalline product. Thus obtained crude, crystalline product was washed with 2 ml of diethyl ether, filtered and dried to obtain 80 mg of the intended product.

melting point: from 217.0° to 219.0° C.

Production Example 15

Synthesis of Compound No. 22 of the invention

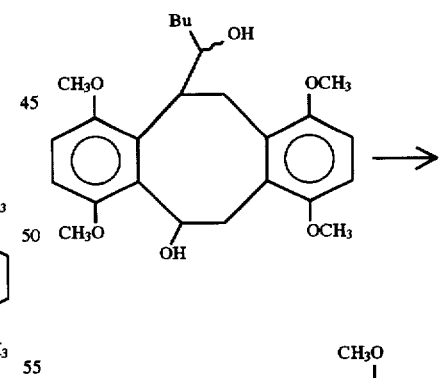

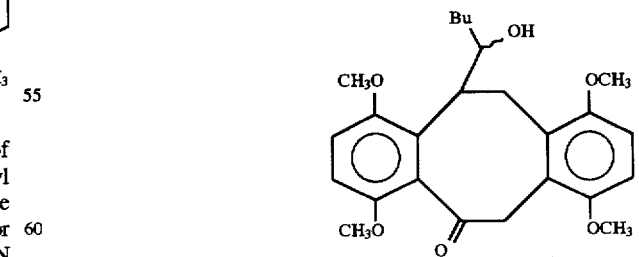

50 mg of Compound No. 21 was dissolved in 5 ml of dichloromethane, and 100 mg of manganese dioxide was added thereto at room temperature and then stirred for 15 hours. The solution was filtered, and the solvent was removed from the resulting filtrate through distillation under reduced pressure to obtain 47 mg of the intended product as a crystal.

melting point: from 185.0° to 188.0° C.

Production Example 16

Synthesis of Compound No. 23 of the invention

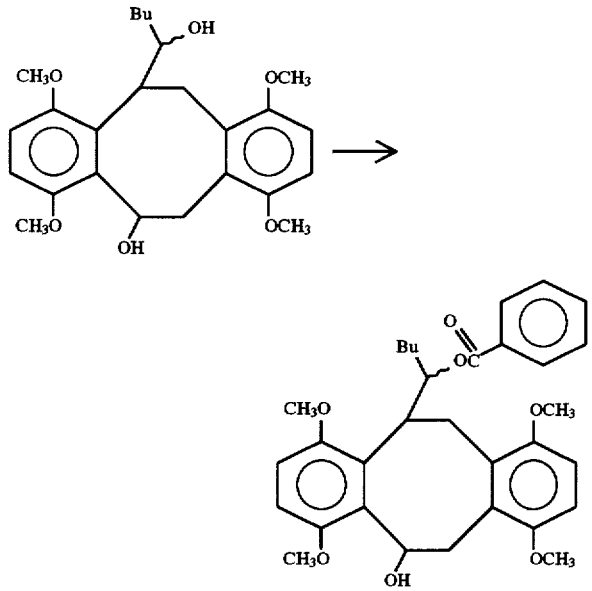

50 mg of Compound No. 21 of was dissolved in 5 ml of dichloromethane. 28 mg of pyridine and 24 mg of benzoyl chloride were dropwise added to the resulting solution at 0° C., and then the solution was stirred at room temperature for 1 hour. Water was added to the solution and then, extracted with 20 ml of ethyl acetate added thereto. The resulting organic layer was washed with 2-N hydrochloric acid and an aqueous sodium hydrogencarbonate solution in that order, and then dried with anhydrous magnesium sulfate. The solvent was removed through distillation under reduced pressure to obtain 62 mg of a crude product. Thus obtained crude product was partitioned through silica gel thin-layer chromatography to obtain 40 mg of the intended product as oil.

Production Example 17

Synthesis of Compound No. 24 of the invention

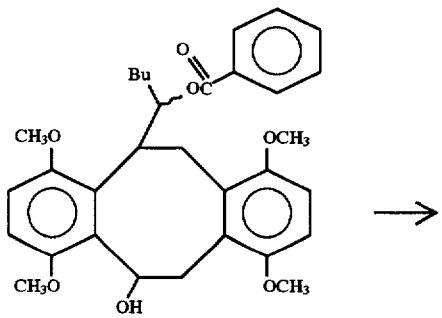

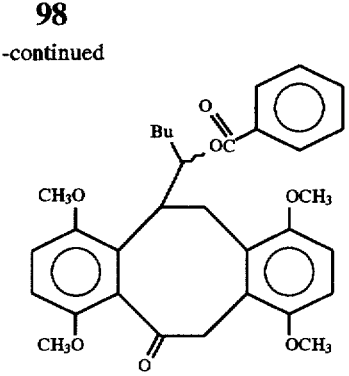

0.5 ml of a solution of 37 mg of dimethylsulfoxide dissolved in dichloromethane was dropwise added to 0.5 ml of dichloromethane containing 0.03 ml of oxalyl chloride as dissolved therein, at −78° C., and then stirred for 5 minutes. Next, 3 ml of a solution of 45 mg of Compound No. 23 as dissolved in dichloromethane was dropwise added thereto at −78° C. and then stirred for 1 hour. Next, 0.2 ml of triethylamine was dropwise added thereto at −40° C., and then stirred at 0° C. for 20 minutes. The resulting solution was extracted with 2 ml of dichloromethane and 2 ml of water added thereto, and the resulting organic layer was washed with 1-N hydrochloric acid and then dried with anhydrous magnesium sulfate. The solvent was removed through distillation under reduced pressure, and 44 mg of the intended product was obtained as a crystal.

melting point: from 178.0° to 180.0° C.

Production Example 18

Synthesis of Compound No. 25 of the invention

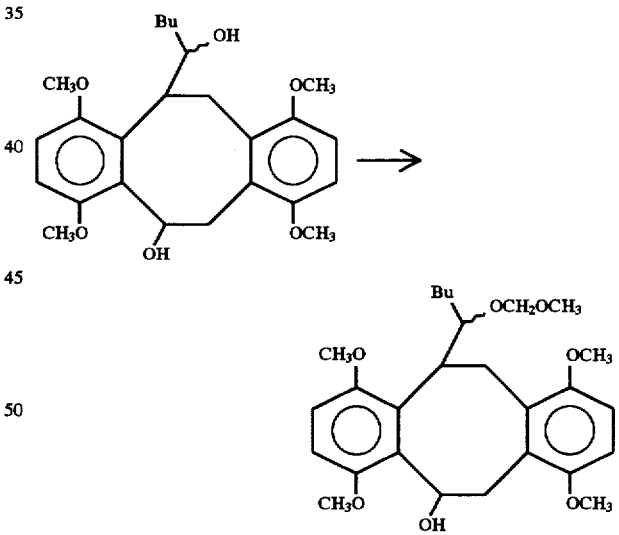

45 mg of Compound No. 21 was dissolved in 10 ml of dichloromethane. 160 mg of triethylamine and 100 mg of chloromethyl methyl ether was added thereto in that order at room temperature, and then stirred for 2 hours. Next, 160 mg of triethylamine and 100 mg of chloromethyl methyl ether were further added thereto, and stirred for 1 hour. This operation was repeated two times, and thereafter the solution was left as it was for 15 hours. Water was added to the solution, which was then extracted with 50 ml of chloroform. The resulting organic layer was washed with 1-N hydrochloric acid and then dried with anhydrous magnesium sulfate. The solvent was removed through distillation under reduced pressure, and 50 mg of a crude product was obtained. Thus obtained crude product was purified through silica gel column chromatography to obtain 35 mg of the intended product as a crystal.

melting point: from 120.0° to 125.0° C.

Production Example 19

Synthesis of Compound No. 26 of the invention

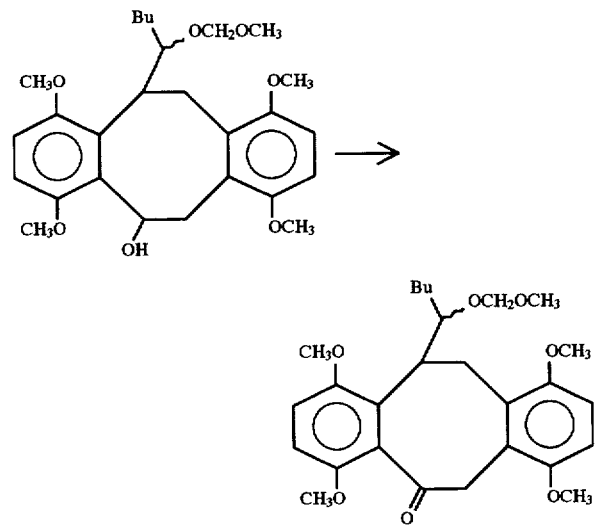

35 mg of Compound No. 25 was dissolved in 10 ml of dichloromethane. 40 mg of sodium acetate and 70 mg of pyridinium chlorocromate (PCC) were added to the solution in that order, and then stirred for 15 hours at room temperature. The solution was extracted with water and diethyl ether added thereto. The resulting organic layer was washed with water and then dried with anhydrous magnesium sulfate. The solvent was removed through distillation under reduced pressure, and 35 mg of a crude product was obtained. Thus obtained crude product was purified through silica gel column chromatography to obtain 31 mg of the intended product as a crystal.

melting point: from 130.0° to 133.0° C.

The physical properties of the compounds of the present invention are shown in Table 6.

TABLE 6

| | Physical property | $^1$H-NMR ($\delta$, CDCl$_3$; TMS) MS |
|---|---|---|
| Compound No. 1 of the present invention | oil | 0.90–0.99(m, 6H), 1.30–1.48(m, 8H), 1.59–1.72(m, 2H), 1.74–1.89(m, 2H) 2.02(s, 3H), 2.86–3.05(m, 4H), 3.10–3.20(m, 2H), 5.20–5.28(m, 1H) |
| Compound No. 2 of the present invention | oil | 0.90–1.00(m, 6H), 1.30–1.98(m, 12H), 2.90–3.14(m, 5H), 3.01(s, 3H), 3.18–3.28(m, 1H), 4.99–5.03(m, 1H) |
| Compound No. 3 of the present invention | oil | 0.02(s, 9H), 0.93–0.98(m, 6H), 1.25–1.64(m, 12H), 2.85–3.05(m, 5H), 3.26(t, J=13.2Hz, 1H), 4.00(m, 1H) MS; 462(M$^+$), 447, 405, 376, 361, 333, 304, 160 |
| Compound No. 4 of the present | oil | 0.93–0.95(m, 6H), 1.26–2.00(m, 12H), 2.56–3.14(m, 6H), 4.99(dt, J=7.5Hz 7.0Hz, 1H) |

TABLE 6-continued

| | Physical property | $^1$H-NMR ($\delta$, CDCl$_3$; TMS) MS |
|---|---|---|
| invention | | 7.13–7.36(m, 10H) MS(FAB); 623(M+1), 251 |
| Compound No. 5 of the prsent invention | oil | 0.88–0.99(m, 6H), 1.26–1.75(m, 12H), 2.93–3.17(m, 6H), 5.12(m, 1H), 6.67(bs, 1H), 7.25 . 7.41(m, 4H) MS(FAB); 544(M+1), 373, 355, 172 |
| Compound No. 6 of the present invention | oil | 0.85–1.00(m, 6H), 1.20–1.89(m, 12H), 2.95–3.10(m, 4H), 3.20–3.31(m, 1H), 3.35–3.42(m, 1H), 4.70(ddt, J=47.9Hz 8.4Hz 7.0Hz, 1H) MS(FAB); 393(M+1), 3.72 |
| Compound No. 6 of the present invention | oil | 0.85–100(m, 6H), 1.20–1.89(m, 12H), 2.95–3.10(m, 4H), 3.20–3.31(m, 1H), 3.35–3.42(m, 1H), 4.70(ddt, J=47.9Hz 8.4Hz 7.0Hz, 1H) MS(FAB); 393(M+1), 372 |
| Compound No. 7 of the present invention | oil | 0.91–1.88(m, 18H), 2.96–3.05(m, 3H), 3.22(t, J=12.7Hz, 1H), 3.49(t, J=12.9Hz, 1H), 4.16–4.20(m, 1H) MS(FAB); 409(M+1), 373, 307 |
| Compound No. 8 of the present invention | oil | 0.85–1.00(m, 6H), 1.25–2.04(m, 10H), 2.99–3.09(m, 5H), 3.59(m, 1H), 5.38(ddt, J=15.4Hz 7.5Hz 1.0Hz, 1H), 5.76(ddt, J=15.4Hz 7.7Hz 1.0Hz, 1H) MS(FAB); 377(M+1), 307, 279 |
| Compound No. 9 of the present invention | oil | 0.89–1.85(m, 16H), 2.45(m, 1H), 2.53(m, H), 3.01–3.10(m, 3H), 3.68(d, J=14.8Hz, 12H), 3.94(d, J=14.8Hz, 1H), 7.33(t, J=6.6Hz, 1H) MS; 372 |
| Compound No. 10 | white crystal | m.p. 203.0–204.0° C. |
| Compound No. 11 of the present invention | oil | 0.98–1.00(m, 6H), 1.20–1.86(m, 12H), 2.96–3.04(m, 3H), 3.10–3.25(m, 2H), 3.47(dd, J=12.8Hz, 6.3Hz, 1H), 3.88–3.96(m, 2H), 3.94–4.06(m, 2H) MS(FAB); 433(M+1) |
| Compound No. 12 of the present invention | oil | 0.91–1.00(m, 6H), 1.25–1.58(m, 18H), 2.88–3.02(m, 3H), 3.03–3.12(m, 2H), 3.25(m, 1H), 3.43–3.49(m, 1H), 3.86–3.94(m, 2H), 4.32–4.36(m, 1H) MS(FAB); 475(M+1), 473 |
| Compound No. 13 | white crystal | m.p. 168–170.0° C. |
| Compound No. 14 of the present invention | oil | 0.88–0.99(m, 6H), 1.24–1.88(m, 13H), 2.80–3.00(m, 5H), 2.97(s, 6H), 3.08–3.13(m, 1H), 3.90–3.94(m, 1H), 3.94(d, J=14.8Hz, 1H), MS(FAB); 417(M+1) |
| Compound No. 15 of the present invention | oil | 0.82–1.00(m, 6H), 1.20–1.80(m, 12H), 2.10(bs, 1H), 2.79–2.89(m, 3H), 2.90–3.00(m, 2H), 3.03–3.12(m, 1H), 3.89–3.92(m, 1H), 7.97(bs, 1H), 8.10(bs, 1H) MS(FAB); 389(M+1) |
| Compound No. 16 of the present invention | oil | 0.90–1.00(m, 6H), 1.20–1.80(m, 13H), 2.80–2.99(m, 5H), 3.06–3.13(m, 1H), 3.90–3.94(m, 1H), 4.52–4.68(m, 4H), 7.25–7.39(m, 10H) MS(FAB); 569(M+1) |
| Compound No. 17 of the present invention | oil | 0.90–1.00(m, 6H), 1.26–1.43(m, 6H), 1.53–1.65(m, 3H), 1.75(m, 1H), 2.73(t, J=7.6Hz, 1H), 2.85–3.00(m, 4H), 3.22(t, J=13.4Hz, 1H), 3.93(dd, J=12.9Hz 5.4Hz, 1H), 7.91–8.09(bs, 2H) MS(FAB); 387(M+1) |
| Compound No. 18 | white crystal | m.p. 232.0–235.0° C. |
| Compound No. 19 | white crystal | m.p. 184.0–186.0° C. |
| Compound No. 20 of the | oil | 0.78–1.08(m, 3H), 1.23–1.75(m, 6H), 1.88–2.20(m, 3H), 3.45–3.80(m, 3H), |

TABLE 6-continued

| | Physical property | $^1$H-NMR ($\delta$, CDCl$_3$; TMS) MS |
|---|---|---|
| present invention | | 3.58(s, 3H), 3.62(s, 3H), 3.67(s, 3H), 3.69(s, 3H), 3.95–4.04(m, 1H), 6.38–6.54(m, 4H), |
| Compound No. 21 | white crystal | m.p. 217.0–219.0° C. |
| Compound No. 22 | white crystal | m.p. 185.0–188.0° C. |
| Compound No. 23 of the present invention | oil | 0.78–0.85(m, 3H), 1.10–1.80(m, 7H), 2.93–3.02(m, 3H), 3.38–3.50(m, 2H), 3.60(s, 3H), 3.68(s, 6H), 3.70(s, 3H), 3.95–4.04(m, 1H), 4.30–4.40(m, 1H), 6.04–6.18(bs, 2H), 6.47(s, 2H), 6.50–6.65(m, 2H), 7.40–7.50(m, 2H), 7.54–7.63(m, 1H), 8.09–8.20(m, 2H) |
| Compound No. 24 | white crystal | m.p. 178.0–180.0° C. |
| Compound No. 25 | white crystal | m.p. 120.0–125.0° C. |
| Compound No. 26 | white crystal | m.p. 130.0–133.0° C. |

Formulation examples of fungicides comprising the compound of the present invention as the active ingredient are mentioned hereinunder, which, however, are not limitative. In the following formulation examples, "parts" are by weight.

Formulation Example 1: Emulsifiable concentrates

| | |
|---|---|
| Compound of the invention | 20 parts |
| Xylene | 55 parts |
| N,N-dimethylformamide | 20 parts |
| Solpol 2680 (trade name, a mixture of a nonionic surface-active agent and an anionic-surface active agent manufactured by Toho Chemical Co., Ltd.) | 5 parts |

The above-mentioned components are homogeneously mixed together to form an emulsifiable concentrate. Upon use, the emulsifiable concentrate is diluted from 50 to 20000 times and applied in an amount of from 5 g/ha to 50 kg/ha in terms of the active ingredient.

Formulation Example 2: Wettable powders

| | |
|---|---|
| Compound of the invention | 25 parts |
| Zeeklite PFP (trade name, a mixture of kaolinite and sericite manufactured by Zeeklite Mining Industries Co., Ltd.) | 66 parts |
| Solpol 5039 (trade name, an anionic-surface active agent manufactured by Toho Chemical Co., Ltd.) | 4 parts |
| Carplex #80 (trade name, white carbon manufactured by Shionogi Pharmaceutical Co., Ltd.) | 3 parts |
| Calcium lignin sulfonate | 2 parts |

The above-mentioned components are homogeneously mixed together and ground to form a wettable powder. Upon use, the wettable powder is diluted with from 50 to 20000 times and applied in an amount of from 5 g/ha to 50 kg/ha in terms of the active ingredient.

Formulation Example 3: Oil solutions

| | |
|---|---|
| Compound of the invention | 10 parts |
| Methyl cellosolve | 90 parts |

The above-mentioned components are homogeneouly mixed together to form an oil solution. Upon use, the oil solution is applied in an amount of from 5 g/ha to 50 kg/ha in terms of the active ingredient.

Formulation Example 4: Dusts

| | |
|---|---|
| Compound of the invention | 3 parts |
| Carplex #80 (trade name, white carbon manufactured by Shionogi Pharmaceutical Co., Ltd.) | 0.5 parts |
| Clay | 95 parts |
| Di-isopropyl phosphate | 1.5 parts |

The above-mentioned components are homogeneously mixed together and ground to form a dust. Upon use, the dust is applied in an amount of from 5 g/ha to 50 kg/ha in terms of the active ingredient.

Formulation Example 5: Granules

| | |
|---|---|
| Compound of the invention | 5 parts |
| Bentonite | 54 parts |
| Talc | 40 parts |
| Calcium ligninsulfonate | 1 part |

The above-mentioned components are mixed homogeneously together and ground, incorporated with a small amount of water and mixed together with stirring. The resulting mixture is granulated by means of extrusion-granulator and dried to form granules. Upon use, the granules are applied in an amount of from 5 g/ha to 50 kg/ha in terms of the active ingredient.

Formulation Example 6: Flowables

| | |
|---|---|
| Compound of the invention | 25 parts |
| Solpol 3358 (trade name, a nonionic surface-active agent manufactured by Toho Chemical Co., Ltd.) | 10 parts |
| Runox 1000C (trade name, an anionic surface-active agent manufactured by Toho Chemical Co., Ltd.) | 0.5 parts |
| 1% aqueous solution Xanthan gum (high molecular compound) | 20 parts |
| Water | 44.5 parts |

The above-mentioned components except the active ingredient are homogeneously melted, and then the compound of the invention is added thereto and well stirred. The resulting mixture is wet-ground in a sand mill to obtain a flowable. Upon use, the flowable is diluted from 50 to 20000 times and applied in an amount of from 5 g/ha to 50 kg/ha in terms of the active ingredient.

Next, formulation examples of medicines comprising the novel compound of the present invention as the active ingredient are mentioned hereinunder, which, however, are not limitative.

Formulation Example 7: Liquid liniment

| Compound of the invention | 3 parts |
|---|---|
| Diethanolamine | 10 parts |
| Ethanol | 87 parts |

Diethanolamine is added to a small amount of ethanol and stirred to prepare a uniform solution. The compound of the invention is added to the resulting solution and dissolved therein by stirring it. Next, the remaining ethanol is added thereto to obtain a liquid liniment.

Formulation Example 8: Ointment

| Compound of the invention | 1 part |
|---|---|
| Diethanolamine | 3 parts |
| White petrolatum | 86 parts |
| Stearic acid | 10 parts |

White petrolatum and stearic acid are heated and melted, and diethanolamine is added thereto to prepare a uniform solution. The compound of the invention is added to the solution and dissolved therein by stirring it. The resulting solution is solidified at room temperature to obtain an ointment.

Formulation Example 9: Tablet

| Compound of the invention | 10 g |
|---|---|
| Lactose | 20 g |
| Starch | 4 g |
| Starch (for paste) | 1 g |
| Magnesium stearate | 100 mg |
| Calcium carboxymethyl cellulose | 7 g |
| Total | 42.1 g |

The above-mentioned components are mixed in an ordinary manner, and then formed into sugar-coated tablets each containing 50 mg/tablet of the active ingredient.

Formulation Example 10: Capsule

| Compound of the invention | 10 g |
|---|---|
| Lactose | 20 g |
| Microcrystalline cellulose | 10 g |
| Magnesium stearate | 1 g |
| Total | 41 g |

The above-mentioned components are mixed in an ordinary manner, and then encapsulated into gelatin capsules. The capsules thus formed contain 50 mg/capsule of the active ingredient.

Formulation Example 11: Soft capsules

| Compound of the invention | 10 g |
|---|---|
| Corn oil | 35 g |
| Total | 45 g |

The above-mentioned components are mixed, and then formed into soft capsules in an ordinary manner.

Formulation Example 12: Ointment

| Compound of the invention | 1.0 g |
|---|---|
| Olive oil | 20 g |
| White petrolatum | 79 g |
| Total | 100 g |

The above-mentioned components are mixed in an ordinary manner to prepare a 1-% ointment.

Formulation Example 13: Aerosol suspension

| (A) | |
|---|---|
| Compound of the invention | 0.25% |
| Isopropyl myristate | 0.10% |
| Ethanol | 26.40% |
| (B) | |
| 60 to % 40 mixture of 1,2-dichlorotetra-fluoroethane and 1-chloro-pentafluoroethane | 73.25% |

The components of (A) are mixed, and the resulting composition (A) is charged into a container provided with a valve. The propellant (B) is jetted into the container through the valve nozzle, at 20° C., up to a gauge pressure of approximately from 2.46 to 2.81 mg/cm$^2$, to prepare an aerosol suspension.

Next, the effectiveness of the compounds of the present invention is demonstrated in the following Test Examples, which, however, are not limitative.

Test Example 1

Test for the fungicidal activity of the compounds of the invention against *Botrytis cinerea*:

Inhibition of Growth of Hyphae

One ml of a chemical liquid to be tested, having a concentration of 10 times of a pre-determined concentration, was put into a laboratory dish, and 9 ml of a potato-sucrose-agar (PSA) medium that had been sterilized and melted was added thereto and solidified to give a plate medium. Cells of *Botrytis cinerea* were grown on a PSA medium, and a disc was stamped out from the medium, using a cork borer having a diameter of 4 mm, and put on the previously-prepared, plate PSA medium containing the chemical. The cells were thus incubated thereon at 25° C. for 3 days, and the diameters of the mycelia thus grown were measured. From the data, calculated was the percentage of inhibition of the growth of hyphae according to the following equation.

Percentage of inhibition of Growth of Hyphae (%)=[(diameter in control area with no chemical added)−(diameter in test area with chemical added)]/(diameter in control area with no chemical added)×100

Inhibition of Germination of Spores

Yeast extract and sucrose were added to a suspension of spores of *Botrytis cinerea* at a final concentration of 3% and 1%, respectively. This was mixed with a chemical liquid to be tested, and the resulting mixture was dropped onto a glass slide. This was incubated at 25° C. and at a high humidity for 20 hours, and then observed with a microscope. The number of the non-germinated spores/50 spores was counted.

Percentage of Inhibition of Germination of Spores=[(non-germinated spores)/50]×100

The results are shown in Table 7.

TABLE 7

| Compound of the Invention | Concentration (ppm) | Inhibition of Growth of Hyphae (%) | Inhibition of Germination of Spores (%) |
|---|---|---|---|
| No. 1 | 100 | 100 | 100 |
| No. 2 | 100 | 88 | 100 |
| No. 3 | 100 | 100 | 100 |
| No. 5 | 100 | 73 | |
| No. 6 | 100 | 100 | 100 |
| No. 7 | 100 | 80 | |
| No. 8 | 100 | 100 | 100 |
| No. 9 | 100 | 100 | 100 |
| No. 10 | 100 | 100 | 76 |
| No. 11 | 100 | 100 | 100 |
| No. 12 | 100 | 100 | 100 |
| No. 13 | 100 | 81 | |
| No. 15 | 100 | 21 | |
| No. 17 | 100 | 61 | |

Test Example 2

Test for disease controlling activity against gray mold:

A chemical liquid as prepared by diluting an emulsifiable concentrate comprising Compound No. 6 of the invention with water to have a concentration of 500 ppm was sprayed through a spray gun over one or two-leaves stage, cucumber seedlings (variety: Sagami-hanjiro) that had grown in pots having a diameter of 7 cm, the amount of the liquid sprayed being 20 ml/pot. On the next day, the leaves were cut out of the seedlings and put onto paper as wetted with water in a vat. A disc (diameter: 4 mm) of the mycelial plexa of *Botrytis cinerea* that had been incubated in a PSA medium was inoculated on the leaves. After the inoculation, the vat was covered with a vinyl cover and put in a thermostat at 18° C. for 5 days. The diameters of the disease lesion formed were measured. The protective value was obtained according to the following equation.

Extermination value=[(diameter (mm) of lesion in non-treated plot)−(diameter (mm) of lesion in treated plot)]/(diameter (mm) of lesion in non-treated plot)×100

The protective value of Compound No. 6 tested herein was 100.

Test Example 3

Test for the anti-thrombocytoagglutination activity of the compounds of the invention in rats:

Test Method

Using a syringe containing therein 1 part by volume of 3.8-% sodium citrate, 9 parts by volume of blood was collected from a male, Wister rat (body weight: 200 to 300 g) through its abdominal aorta. The blood was centrifuged at 200×g for 7 minutes at room temperature to prepare a platelet-rich plasma (PRP) sample. Next, the residue was further centrifuged at 2,000×g for 10 minutes to prepare a platelet-poor plasma (PPP) sample.

PRP and PPP samples were diluted to have a concentration of 300,000 cells/mm³, and these dilutions were used herein. Each sample was put into an agglutination cell. The range for the measurement of the transmittance through the cell was settled at 0% for PRP and at 100% for PPP. A chemical to be tested was dissolved in 100-% dimethylsulfoxide (DMSO), and the resulting chemical solution was added to the cell containing PRP at a final DMSO concentration of 0.25%. The samples were then incubated at 37° C. and at 900 rpm for 2 minutes. After the incubation, an agglutinant was added to these, and the agglutination curves were recorded. The anti-agglutination activity of the chemical tested was represented by the concentration thereof, at which the agglutination was inhibited by 50% of the control, $IC_{50}$ (μM). The concentrations of the agglutinants ADP, collagen and U46619 employed herein were their minimum concentrations at which they induce the highest agglutination (ADP: 5 to 10 μM; collagen: 2.5 to 10 μg/ml; U46619: 0.5 to 1 μM). For the measurement of the thrombocytoagglutination, herein employed was NBS HEMA TRACER 601.

The results are shown in Table 8.

TABLE 8

| | $IC_{50}$ (μM) | | |
|---|---|---|---|
| | ADP | Collagen | U46619 |
| Compound No. 6 | 9 | 158 | 905 |
| Compound No. 9 | 172 | 474 | |
| Compound No. 10 | 67 | 105 | 632 |
| Compound No. 12 | 84 | 194 | 239 |

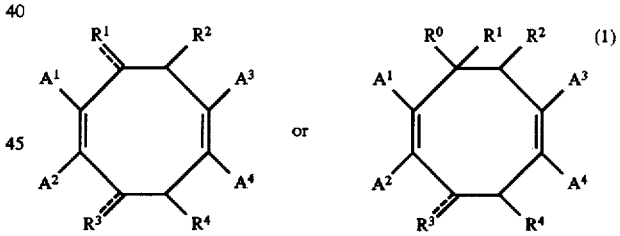

U46619

INDUSTRIAL APPLICABILITY

As has been described hereinabove, the cyclooctadiene derivatives of the present invention have excellent bactericidal activity and antimold activity and also have anti-thrombocytoagglutination activity, and are therefore useful as bactericides, antimolds and antithrombocytic agents.

We claim:

1. A cyclooctadiene derivative of the formula (1):

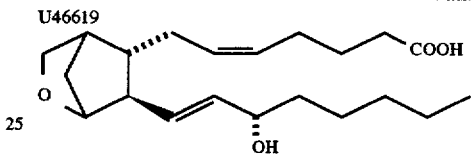

wherein $A^1$, $A^2$, $A^3$ and $A^4$ each independently represent $COOR^5$ (where $R^5$ represents a hydrogen atom, a $C_1$-$C_{10}$ alkyl group, a $C_2$-$C_{10}$ alkenyl group, a $C_2$-$C_{10}$ alkynyl group, a phenyl group (the phenyl group may be optionally substituted by a halogen atom, a $C_1$-$C_6$ alkyl group, a $C_1$-$C_6$ haloalkyl group, a $C_1$-$C_6$ alkoxy group, a cyano group and/or a nitro group), or a $C_7$-$C_{12}$ aralkyl group (the aralkyl group may be optionally substituted by a halogen atom, a $C_1$-$C_6$ alkyl group, a $C_1$-$C_6$ haloalkyl group, a $C_1$-$C_6$ alkoxy group, a cyano group and/or a nitro group)), or $CONR^6R^7$ (where $R^6$ and $R^7$ each independently represent a hydrogen atom, a $C_1$-$C_{10}$ alkyl group or a phenyl group (the phenyl group may be optionally substituted by a halogen atom, a $C_1$-$C_6$ alkyl group, a $C_1$-$C_6$ haloalkyl group, a $C_1$-$C_6$ alkoxy group, a cyano group and/or a nitro group)), or $A^1$ and $A^2$, and/or $A^3$ and $A^4$ may be combined together to represent group(s) of:

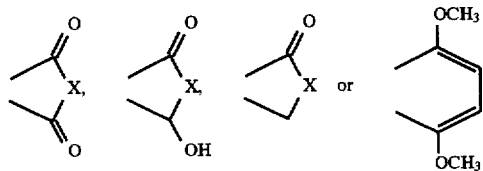

in which X represents an oxygen atom or NR$^8$ {where R$^8$ represents a hydrogen atom, a C$_1$–C$_{10}$ alkyl group, a phenyl group (the phenyl group may be optionally substituted by a halogen atom, a C$_1$–C$_6$ alkyl group, a C$_1$–C$_6$ haloalkyl group, a C$_1$–C$_6$ alkoxy group, a cyano group and/or a nitro group), or a C$_7$–C$_{12}$ aralkyl group (the aralkyl group may be optionally substituted by a halogen atom, a C$_1$–C$_6$ alkyl group, a C$_1$–C$_6$ haloalkyl group, a C$_1$–C$_6$ alkoxy group, a cyano group and/or a nitro group)};

R$^0$, R$^1$, R$^2$, R$^3$ and R$^4$ each independently represent a hydrogen atom, a halogen atom, a hydroxyl group, an optionally-substituted C$_1$–C$_{10}$ alkyl group, an optionally-substituted C$_2$–C$_{10}$ alkenyl group, or an optionally-substituted C$_2$–C$_{10}$ alkynyl group;

the substituent for the optionally-substituted groups can be any one or more selected from the group consisting of a halogen atom, a C$_1$–C$_6$ alkyl group, a C$_2$–C$_6$ alkenyl group, a C$_2$–C$_6$ alkynyl group, a C$_1$–C$_6$ haloalkyl group, OR$^9$ {where R$^9$ represents a hydrogen atom, a C$_1$–C$_6$ alkyl group, a C$_1$–C$_6$ alkenyl group, a C$_2$–C$_6$ alkynyl group, a C$_1$–C$_6$ haloalkyl group, a silyl group, a C$_1$–C$_4$ alkylsulfonyl group, a C$_7$–C$_{12}$ aralkyl group (the aralkyl group may be optionally substituted by a halogen atom, a C$_1$–C$_6$ alkyl group, a C$_1$–C$_6$ haloalkyl group, a C$_1$–C$_6$ alkoxy group, a cyano group and/or a nitro group), a phosphoryl group, a C$_2$–C$_{10}$ alkoxyalkyl group, or COR$^{14}$ where R$^{14}$ represents a C$_1$–C$_6$ alkyl group, a phenyl group (the phenyl group may be optionally substituted by a halogen atom, a C$_1$–C$_6$ alkyl group, a C$_1$–C$_6$ haloalkyl group, a C$_1$–C$_6$ alkoxy group, a cyano group and/or a nitro group), a C$_1$–C$_6$ alkoxy group, or NR$^{15}$R$^{16}$ (where R$^{15}$ and R$^{16}$ each independently represent a hydrogen atom, a C$_1$–C$_6$ alkyl group or a phenyl group (the phenyl group may be optionally substituted by a halogen atom, a C$_1$–C$_6$ alkyl group, a C$_1$–C$_6$ haloalkyl group, a C$_1$–C$_6$ alkoxy group, a cyano group and/or a nitro group)))},
SR$^{10}$ (where R$^{10}$ represents a hydrogen atom, a C$_1$–C$_6$ alkyl group, a C$_2$–C$_6$ alkenyl group, a C$_2$–C$_6$ alkynyl group, a C$_7$–C$_{12}$ aralkyl group (the aralkyl group may be optionally substituted by a halogen atom, a C$_1$–C$_6$ alkyl group, a C$_1$–C$_6$ haloalkyl group, a C$_1$–C$_6$ alkoxy group, a cyano group and/or a nitro group), NR$^{11}$R$^{12}$ {where R$^{11}$ and R$^{12}$ each independently represent a hydrogen atom, a C$_1$–C$_6$ alkyl group, a phenyl group (the phenyl group may be optionally substituted by a halogen atom, a C$_1$–C$_6$ alkyl group, a C$_1$–C$_6$ haloalkyl group, a C$_1$–C$_6$ alkoxy group, a cyano group and/or a nitro group) or COR$^{17}$ (where R$^{17}$ represents a C$_1$–C$_6$ alkyl group, a phenyl group (the phenyl group may be optionally substituted by a halogen atom, a C$_1$–C$_6$ alkyl group, a C$_1$–C$_6$ haloalkyl group, a C$_1$–C$_6$ alkoxy group, a cyano group and/or a nitro group) or C$_1$–C$_6$ alkoxy group)}, =O, =NR$^{13}$ {where R$^{13}$ represents a C$_1$–C$_6$ alkyl group, a phenyl group (the phenyl group may be optionally substituted by a halogen atom, a C$_1$–C$_6$ alkyl group, a C$_1$–C$_6$ haloalkyl group, a C$_1$–C$_6$ alkoxy group, a cyano group and/or a nitro group) or OR$^{18}$ (where R$^{18}$ represents a hydrogen atom, a C$_1$–C$_6$ alkyl group or COR$^{19}$ (where R$^{19}$ represents a C$_1$–C$_6$ alkyl group, a phenyl group (the phenyl group may be optionally substituted by a halogen atom, a C$_1$–C$_6$ alkyl group, a C$_1$–C$_6$ haloalkyl group, a C$_1$–C$_6$ alkoxy group, a cyano group and/or a nitro group) or NR$^{20}$R$^{21}$ (where R$^{20}$ and R$^{21}$ each independently represent a hydrogen atom, a C$_1$–C$_6$ alkyl group, a phenyl group (the phenyl group may be optionally substituted by a halogen atom, a C$_1$–C$_6$ alkyl group, a C$_1$–C$_6$ haloalkyl group, a C$_1$–C$_6$ alkoxy group, a cyano group and/or a nitro group)))}, and

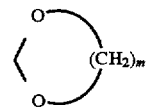

(where m is an integer of from 2 to 4);

the symbol ═══ represents a single or double bond, and when it is a double bond, then R$^1$ and R$^3$ each independently may represent an oxygen atom;

provided that the case where all of R$^0$, R$^1$, R$^2$, R$^3$ and R$^4$ represent hydrogen atoms at the same time is excluded.

2. Cyclooctadiene derivatives as claimed in claim 1, wherein R$^0$, R$^2$ and R$^3$ each independently represent a hydrogen atom, a halogen atom, a hydroxyl group or a C$_1$–C$_{10}$ alkyl group, or R$^3$ represents =O.

3. Cyclooctadiene derivatives as claimed in claim 2, wherein R$^4$ represents a hydrogen atom, a halogen atom or a C$_1$–C$_{10}$ alkyl group.

4. Cyclooctadiene derivatives as claimed in claim 3, wherein A$^1$, A$^2$, A$^3$ and A$^4$ each independently represent COOR$^{22}$ (where R$^{22}$ represents a hydrogen atom or a C$_1$–C$_{10}$ alkyl group), or A$^1$ and A$^2$, and A$^3$ and A$^4$ are combined together to represent a group of:

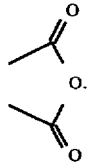

5. Cyclooctadiene derivatives as claimed in claim 4, wherein
R$^0$, R$^2$ and R$^3$ represent hydrogen atoms;
R$^4$ represents —CH$_2$CH$_2$CH$_2$CH$_3$;
R$^1$ represents a group of:

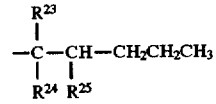

or a group of:

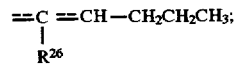

R$^{23}$ represents a hydrogen atom, a halogen atom, a C$_1$–C$_6$ alkyl group or a C$_1$–C$_6$ alkoxy group;
R$^{24}$ represents a hydrogen atom, a halogen atom, a C$_1$–C$_6$ alkyl group, —OR$^{27}$ {where R$^{27}$ represents a hydrogen atom, $C_1$–$C_6$ alkyl group, a $C_1$–$C_6$ haloalkyl group, a $C_7$–$C_{12}$ aralkyl group (the aralkyl group may be optionally substituted by a halogen atom, a $C_1$–$C_6$ alkyl group, a $C_1$–$C_6$ haloalkyl group, a $C_1$–$C_6$ alkoxy group, a cyano group and/or a nitro group), a $C_2$–$C_6$ alkoxyalkyl group or —$COR^{28}$ (where $R^{28}$ represents a $C_1$–$C_6$ alkyl group, a phenyl group (the phenyl group may be optionally substituted by a halogen atom, a $C_1$–$C_6$ alkyl group, a $C_1$–$C_6$ haloalkyl group, a $C_1$–$C_6$ alkoxy group, a cyano group and/or a nitro group), a $C_1$–$C_6$ alkoxy group or $NR^{29}R^{30}$ (where $R^{29}$ and $R^{30}$ each independently represent a hydrogen atom, a $C_1$–$C_6$ alkyl group or a phenyl group (the phenyl group may be optionally substituted by a halogen atom, a $C_1$–$C_6$ alkyl group, a $C_1$–$C_6$ haloalkyl group, a $C_1$–$C_6$ alkoxy group, a cyano group and/or a nitro group)))}, or $R^{23}$ and $R^{24}$ are combined together to represent =O or a group of:

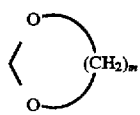

(where m is an integer of from 2 to 4);

$R^{25}$ represents a hydrogen atom, a halogen atom or a $C_1$–$C_6$ alkyl group;

$R^{26}$ represents a hydrogen atom, a halogen atom or a $C_1$–$C_6$ alkyl group; and the symbol ═══ represents a single or double bond.

6. Compound of formula (2):

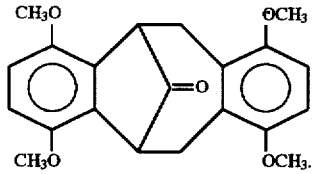

(2)

7. Compound of formula (3):

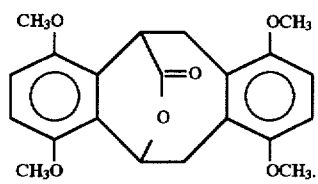

(3)

8. Compounds of formula (4):

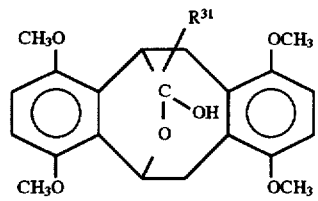

(4)

wherein $R^{31}$ represents a $C_1$–$C_{10}$ alkyl group or a $C_2$–$C_{10}$ alkenyl group.

9. An agrohorticultural fungicide comprising one or more of the cyclooctadiene derivatives as claimed in claim 1 and a carrier.

10. An antimold agent comprising one or more of the cyclooctadiene derivatives as claimed in claim 1 and a diluent.

11. An antithrombocytic agent comprising one or more of the cyclooctadiene derivatives as claimed in claim 1 and a diluent.

* * * * *